US010246457B2

(12) United States Patent
Siu et al.

(10) Patent No.: US 10,246,457 B2
(45) Date of Patent: Apr. 2, 2019

(54) INDAZOLE AND AZAINDAZOLE BTK INHIBITORS

(71) Applicant: MERCK SHARP & DOHME CORP., Rahway, NJ (US)

(72) Inventors: Tony Siu, Brookline, MA (US); Michael D. Altman, Needham, MA (US); Brian M. Andresen, Sharon, MA (US); Jian Liu, Edison, NJ (US); Joseph Kozlowski, Princeton, NJ (US); Sobhana Babu Boga, Scotch Plains, NJ (US); Younong Yu, East Brunswick, NJ (US); Rajan Anand, Fanwood, NJ (US); Jiaqiang Cai, Shanghai (CN); Dahai Wang, Shanghai (CN); Shilan Liu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/564,352

(22) PCT Filed: Apr. 4, 2016

(86) PCT No.: PCT/US2016/025809

§ 371 (c)(1),
(2) Date: Oct. 4, 2017

(87) PCT Pub. No.: WO2016/164285

PCT Pub. Date: Oct. 13, 2016

(65) Prior Publication Data

US 2018/0127411 A1 May 10, 2018

(30) Foreign Application Priority Data

Apr. 8, 2015 (WO) ................ PCT/CN2015/076041

(51) Int. Cl.

| | |
|---|---|
| ***C07D 471/04*** | (2006.01) |
| ***C07D 401/14*** | (2006.01) |
| ***C07D 405/14*** | (2006.01) |
| ***C07D 401/10*** | (2006.01) |
| ***C07D 403/04*** | (2006.01) |
| ***C07D 403/10*** | (2006.01) |
| ***C07D 403/14*** | (2006.01) |
| ***C07D 409/14*** | (2006.01) |
| ***A61P 19/02*** | (2006.01) |
| ***A61K 45/06*** | (2006.01) |
| ***C07D 231/56*** | (2006.01) |
| ***C07D 413/14*** | (2006.01) |

(52) U.S. Cl.

CPC ............ *C07D 471/04* (2013.01); *A61K 45/06* (2013.01); *A61P 19/02* (2018.01); *C07D 231/56* (2013.01); *C07D 401/10* (2013.01); *C07D 401/14* (2013.01); *C07D 403/04* (2013.01); *C07D 403/10* (2013.01); *C07D 403/14* (2013.01); *C07D 405/14* (2013.01); *C07D 409/14* (2013.01); *C07D 413/14* (2013.01)

(58) Field of Classification Search

CPC .. C07D 471/04; C07D 401/14; C07D 401/10; C07D 405/14; C07D 403/04; C07D 403/10; C07D 403/14; C07D 409/14; C07D 231/56; C07D 413/14; A61K 45/06

See application file for complete search history.

(56) References Cited

U.S. PATENT DOCUMENTS

| | | | |
|---|---|---|---|
| 2007/0232620 A1 | 10/2007 | Dorsch et al. | |
| 2009/0286768 A1 | 11/2009 | Crew et al. | |
| 2010/0010008 A1 | 1/2010 | Caruso et al. | |
| 2010/0197688 A1* | 8/2010 | Nantermet | C07C 233/80 514/235.2 |
| 2012/0277255 A1 | 11/2012 | Honigberg et al. | |

FOREIGN PATENT DOCUMENTS

| | | |
|---|---|---|
| WO | WO2011019780 | 2/2011 |
| WO | WO2013010380 A1 | 1/2013 |
| WO | WO2013010868 | 1/2013 |
| WO | WO2013010869 | 1/2013 |

* cited by examiner

*Primary Examiner* — D Margaret M Seaman

(74) *Attorney, Agent, or Firm* — Matthew A. Leff; Laura M. Ginkel

(57) ABSTRACT

The present invention provides Bruton's Tyrosine Kinase (Btk) inhibitor compounds according to Formula (I), or pharmaceutically acceptable salts thereof, wherein $X^1$, $X^2$, $R^1$, $R^7$, $R^8$ and $R^9$ are as herein described. The present invention also provides pharmaceutical compositions comprising these compounds and methods for their use in therapy. In particular, the present invention relates to the use of Btk inhibitor compounds of Formula (I) in the treatment of Btk mediated disorders.

(I)

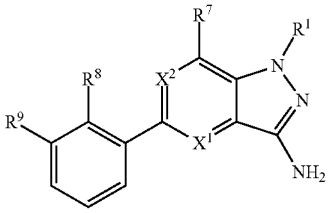

8 Claims, No Drawings

Specification includes a Sequence Listing.

```
SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Glu Gln Glu Asp Glu Pro Glu Gly Asp Tyr Phe Glu Trp Leu Glu
1               5                   10                  15
```

INDAZOLE AND AZAINDAZOLE BTK INHIBITORS

FIELD OF THE INVENTION

The present invention relates to Btk inhibitor compounds, to pharmaceutical compositions comprising these compounds and to their use in therapy. In particular, the present invention relates to the use of Btk inhibitor compounds in the treatment of Bruton's Tyrosine Kinase (Btk) mediated disorders.

BACKGROUND OF THE INVENTION

B lymphocyte activation is important in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll-like receptor signaling was suggested. Functional mutations in Btk in human results in the primary immunodeficiency disease called XLA which is characterized by a defect in B cell development with a block between pro- and pre-B cell stages. This results in an almost complete absence of B lymphocytes in humans causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcεR-mediated mast cell activation, Btk inhibitors may also show potential in the treatment of allergic responses [Gilfillan et al, Immunological Reviews 288 (2009) pp 149-169].

Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-94].

Some classes of Btk inhibitor compounds have been described as kinase inhibitors, e.g., Imidazo[1,5-f][1,2,4]triazine compounds have been described in WO2005097800 and WO2007064993. Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts $Src^{-/-}Fyn^{-/-}$ and $Src^{-/-}Yes^{-/-}$ show a severe phenotype with effects on movement and breathing. The triple knockouts $Src^{-/-}Fyn^{-/-}Yes^{-/-}$ die at day 9.5 [Klinghoffer et al, EMBO J., 18 (1999) pp 2459-2471]. For the double knockout $Src^{-/-}Hck^{-/-}$, two thirds of the mice die at birth, with surviving mice developing osteopetrosis, extramedullary hematopoiseis, anemia, leukopenia [Lowell et al, Blood, 87 (1996) pp 1780-1792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein refers to an amount of the compound of Formula (I) and/or an additional therapeutic agent, or a composition thereof that is effective in producing the desired therapeutic, ameliorative, inhibitory, or preventative effect when administered to a patient suffering from a disease or condition mediated by Btk. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to cancer or an inflammatory disease or disorder, refers to reducing the likelihood of an autoimmune or inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_{1-6}$alkyl) or from 1 to 3 carbon atoms ($C_{1-3}$alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl, and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms ($C_{1-6}$fluoroalkyl). In another embodiment, a fluoroalkyl group has from 1 to 3 carbon atoms ($C_{1-3}$fluoroalkyl). In another embodiment, a fluoroalkyl group is substituted with from 1 to 3 fluorine atoms. Non-limiting examples of fluoroalkyl groups include $—CH_2F$, $—CHF_2$, and $—CF_3$. The term "$C_1$-$C_3$ fluoroalkyl" refers to a fluoroalkyl group having from 1 to 3 carbon atoms.

The term "alkylene," as used herein, refers to an alkyl group, as defined above, wherein one of the alkyl group's hydrogen atoms has been replaced with a bond. Non-limiting examples of alkylene groups include $—CH_2—$, $—CH_2CH_2—$, $—CH_2CH_2CH_2—$, $—CH_2CH_2CH_2CH_2—$, $—CH(CH_3)CH_2CH_2—$, $—CH(CH_3)—$, and $—CH_2CH(CH_3)CH_2—$. In one embodiment, an alkylene group has from 1 to about 6 carbon atoms ($C_{1-6}$alkylene). In another embodiment, an alkylene group has from 1 to 3 carbon atoms ($C_{1-3}$alkylene). In another embodiment, an alkylene group is branched. In another embodiment, an alkylene group is linear. In one embodiment, an alkylene group is $—CH_2—$. Unless otherwise indicated, an alkylene group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to 4 carbon atoms. Non-limiting examples of alkenyl groups include ethenyl, propenyl, n-butenyl, 3-methylbut-2-enyl, n-pentenyl, octenyl, and decenyl. The term "$C_{2-6}$alkenyl" refers to an alkenyl group having from 2 to 6 carbon atoms. The term "$C_{2-4}$alkenyl" refers to an alkenyl group having from 2 to 4 carbon atoms. Unless otherwise indicated, an alkenyl group is unsubstituted.

The term "alkoxy," as used herein, refers to an —O-alkyl group, wherein an alkyl group is as defined above. Non-limiting examples of alkoxy groups include methoxy, ethoxy, n-propoxy, isopropoxy, n-butoxy, and tert-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$aryl). In another embodiment an aryl group is phenyl. Non-limiting examples of aryl groups include phenyl and naphthyl.

The term "cycloalkyl," as used herein, refers to a saturated ring containing the specified number of ring carbon atoms, and no heteroatom. In a like manner the term "$C_{3-6}$cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

The term "heteroaryl," or "heteroaryl ring," as used herein, refers to an aromatic monocyclic or multicyclic ring system comprising about 5 to about 14 ring atoms, wherein from 1 to 3 of the ring atoms is independently N, O, or S and the remaining ring atoms are carbon atoms. In one embodiment, a heteroaryl group has 5 to 10 ring atoms. In another embodiment, a heteroaryl group is monocyclic ring system and has 5 or 6 ring atoms. In another embodiment, a heteroaryl group is a bicyclic ring system. A heteroaryl group is joined via a ring carbon atom. The term "heteroaryl" also includes a heteroaryl as defined above fused to a heterocycle as defined below. The term "heteroaryl" also encompasses a heteroaryl group, as defined above, which is fused to a benzene, a cyclohexadiene or a cyclohexene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and the like. In one embodiment, a heteroaryl group is a 5-membered heteroaryl. In another embodiment, a heteroaryl group is a 6-membered heteroaryl.

The term "heterocyclyl" or "heterocyclic ring"," as used herein, refers to a non-aromatic saturated or partially saturated monocyclic or multicyclic ring system containing 3 to 11 ring atoms, wherein from 1 to 4 of the ring atoms are independently O, S, or N, and the remainder of the ring atoms are carbon atoms. In one embodiment, a heterocyclyl group is monocyclic and has from 3 to 7 ring atoms. In another embodiment, a heterocyclyl group is monocyclic and has from about 4 to 7 ring atoms. In another embodiment, a heterocyclyl group is bicyclic and has from 7 to 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. A heterocyclyl group can be joined to the rest of the molecule via a ring carbon or ring nitrogen atom. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidinyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone, and the like.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation from a reaction mixture to a useful degree of purity, and formulation into an efficacious therapeutic agent.

The term "optionally substituted" means that a compound may or may not be substituted with the specified groups, radicals or moieties.

A "subject" is a human or non-human mammal. In one embodiment, a subject is a human. In another embodiment, the subject is a chimpanzee, dog, or cat.

When any substituent or variable occurs more than one time in any constituent or the compound of Formula (I), its definition on each occurrence is independent of its definition at every other occurrence, unless otherwise indicated. For example, description of radicals which include the expression "$-N(C_{1-3}alkyl)_2$" means $-N(CH_3)(CH_2CH_3)$, $-N(CH_3)(CH_2CH_2CH_3)$, and $-N(CH_2CH_3)(CH_2CH_2CH_3)$, as well as $-N(CH_3)_2$, $-N(CH_2CH_3)_2$, and $-N(CH_2CH_2CH_3)_2$.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), 1-hydroxy-2-naphthoates (also known as xinafoates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference. Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

In the above definitions with multifunctional groups, the attachment point is at the last group, unless otherwise specified on the substituent group by a dash. A dash on the substituent group would then represent the point of attachment.

It should be noted that any carbon as well as heteroatom with unsatisfied valences in the text, schemes, examples and tables herein is assumed to have the sufficient number of hydrogen atom(s) to satisfy the valences.

Compounds of the Invention

In embodiment no. 1, the present invention provides compounds according to Formula (I)

Formula (I)

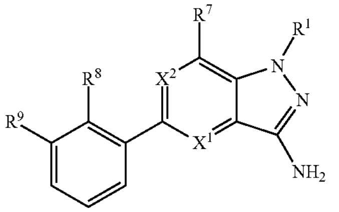

wherein:

$X^1$ is N or C(H);

$X^2$ is N or C($R^6$);

$R^1$ is H, $C_{1-3}$alkyl, or —$CH_2$—$R^{1a}$, wherein $R^{1a}$ is phenyl or pyridyl;

$R^6$ is H or $C_{1-3}$alkyl;

$R^7$ is:

(a.) a group of the formula —C(O)N($R^{7a}$)($R^{7b}$), wherein $R^{7a}$ and $R^{7b}$ are independently H or $C_{1-3}$alkyl; or alternatively, $R^{7a}$ and $R^{7b}$ together with the N to which they are attached form a 5- to 6-membered heterocyclyl optionally containing 1 additional heteroatom selected from N or O;

(b.) Cy, wherein Cy is phenyl or a 5- or 6-membered heteroaryl containing 1 to 3 N ring atoms; wherein Cy is unsubstituted or substituted by 1 to 2 $R^c$ substituents selected from:

(i.) $C_{1-4}$alkyl, (ii.) a group of the formula —C($R^{7d}$)$_2$$CO_2$H, wherein $R^{7d}$ is H or $C_{1-3}$alkyl;

(iii.) —$CH_2CH_2OCH_3$; or (iv.) tetrahydropyranyl;

or alternatively, two $R^c$ substituents, together with the atoms to which they are attached form a 5- to 6-membered heterocyclyl containing 1 N ring atom;

(c.) —C(O)OH;

(d.) H;

(e.) $C_{1-3}$alkyl; or (f.) $C_{1-3}$fluoroalkyl;

$R^8$ is H, $C_{1-3}$alkyl or $C_{1-3}$hydroxyalkyl;

$R^9$ is:

(a.) a group of the formula

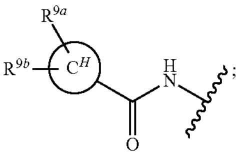;

(b.) a group of the formula

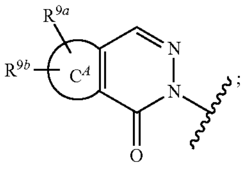

or (c.) a group of the formula

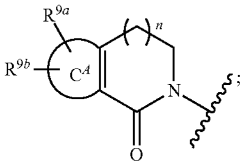

ring $C^H$ is phenyl, thienyl or tetrahydrobenzothienyl;

ring $C^A$ is phenyl or a 5- to 6-membered heteroaryl containing 1 to 3 heteroatoms selected from N, O, or S;

$R^{9a}$ and $R^{9b}$ are each independently H, $C_{1-6}$alkyl, $C_{1-6}$fluoroalkyl, or halo;

the subscript n is 0 or 1; or a pharmaceutically acceptable salt thereof.

In embodiment no. 2, the present invention provides a compound of Formula (I) wherein $X^2$ is $C(R^6)$, and the remaining variables are as set forth in embodiment no. 1.

In embodiment no. 3, the present invention provides a compound of Formula (I) wherein $X^1$ and $X^2$ are both C(H), and the remaining variables are as set forth in embodiment no. 1.

In embodiment no. 4, the present invention provides a compound of Formula (I) wherein $R^1$ is H, and the remaining variables are as set forth in embodiment no. 1.

In embodiment no. 5, the present invention provides a compound of Formula (I) wherein $R^7$ is:

(a.) a group of the formula —$C(O)N(R^{7a})(R^{7b})$, wherein $R^{7a}$ and $R^{7b}$ are independently H or methyl; or alternatively, $R^{7a}$ and $R^{7b}$ together with the N to which they are attached form a morpholinyl ring;

(b.) Cy, wherein Cy is phenyl, pyrazolyl, or pyridinyl; wherein Cy is unsubstituted or substituted by 1 to 2 $R^c$ substituents selected from:

(i.) $C_{1-4}$alkyl, (ii.) a group of the formula —$C(R^{7d})_2CO_2H$, wherein $R^{7d}$ is H or methyl;

(iii.) —$CH_2CH_2OCH_3$; or (iv.) tetrahydropyranyl;

(c.) —C(O)OH;

(d.) H;

(e.) methyl; or (f) trifluoromethyl; and the remaining variables are as set forth in embodiment no. 1.

In embodiment no. 6, the present invention provides a compound of Formula (I) wherein $R^7$ is a group of the formula —$C(O)N(R^{7a})(R^{7b})$, wherein $R^{7a}$ and $R^{7b}$ are independently H or methyl; and the remaining variables are as set forth in embodiment no. 1.

In embodiment no. 7, the present invention provides a compound of Formula (I) wherein $R^7$ is Cy, wherein Cy is phenyl, pyrazolyl, or pyridinyl; wherein Cy is unsubstituted or substituted by 1 to 2 $R^c$ substituents selected from:

(i.) $C_{1-4}$alkyl, (ii.) a group of the formula —$C(R^{7d})_2CO_2H$, wherein $R^{7d}$ is H or methyl;

(iii.) —$CH_2CH_2OCH_3$; or (iv.) tetrahydropyranyl; and the remaining variables are as set forth in embodiment no. 1.

In embodiment no. 8, the present invention provides a compound of Formula (I) wherein $R^7$ is a group of the formula

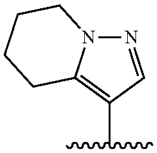

and the remaining variables are as set forth in embodiment no. 1.

In embodiment no. 9, the present invention provides a compound of Formula (I) wherein $R^8$ is hydroxymethyl or methyl, and the remaining variables are as set forth in embodiment no. 1.

In embodiment no. 10, the present invention provides a compound of Formula (I) wherein $R^9$ is

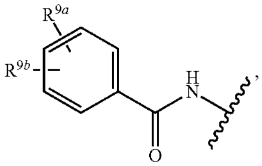,

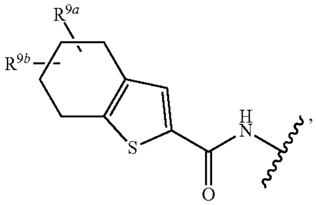,

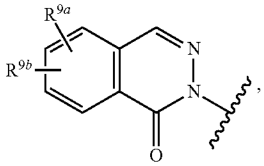, or 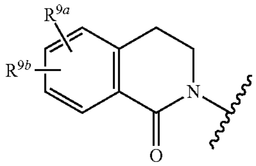;

and $R^{9a}$ and $R^{9b}$ are each independently H, tert-butyl, fluoro or a group of the formula

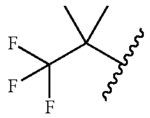;

and the remaining variables are as set forth in embodiment no. 1.

In embodiment no. 11, the present invention provides a compound of Formula (I) wherein $R^9$ is

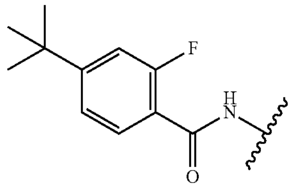

or

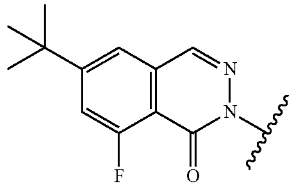

;

and the remaining variables are as set forth in embodiment no. 1.

In embodiment no. 12, the present invention provides a compound of Formula (I) wherein:

$X^1$ is as set forth in embodiment no. 1;

$X^2$ is $C(R^6)$ and $R^6$ is H;

$R^1$ is H;

$R^7$ is as set forth in embodiment nos. 6, 7, or 8;

$R^8$ is hydroxymethyl or methyl; and $R^9$ is as set forth in embodiment no. 10.

In embodiment no. 13, the present invention provides a compound of Formula (I) wherein $X^1$ and $X^2$ are both C(H), and $R^1$, $R^7$, $R^8$, and $R^9$ are as set forth in embodiment no. 12.

In embodiment no. 14, the present invention provides a compound of Formula (I) wherein:

$X^1$ and $X^2$ are both C(H), $R^7$ is as set forth in embodiment no. 6; and $R^1$, $R^8$, and $R^9$ are as set forth in embodiment no. 12.

In embodiment no. 15, the present invention provides a compound of Formula (I) wherein:

$X^1$ and $X^2$ are both C(H), $R^7$ is as set forth in embodiment no. 7; and $R^1$, $R^8$, and $R^9$ are as set forth in embodiment no. 12.

In embodiment no. 16, the present invention provides a compound of Formula (I) wherein:

$X^1$ and $X^2$ are both C(H), $R^7$ is as set forth in embodiment no. 8; and $R^1$, $R^8$, and $R^9$ are as set forth in embodiment no. 12.

In embodiment no. 17, the present invention provides a compound of Formula (I) wherein:

$X^1$ and $X^2$ are both C(H), $R^9$ is as set forth in embodiment no. 11; and $R^1$, $R^7$, and $R^8$ are as set forth in embodiment no. 12.

Non-limiting examples of the compounds of the present invention include:

3-amino-5-[3-(6-tert-butyl-8-fluoro-1-oxophthalazin-2(1H)-yl)-2-(hydroxymethyl)phenyl]-1H-indazole-7-carboxylic acid, 2-[3-(3-amino-6-methyl-1H-indazol-5-yl)-2-(hydroxymethyl)phenyl]-6-tert-butyl-8-fluorophthalazin-1(2H)-one, 3-amino-5-[3-(6-tert-butyl-8-fluoro-1-oxophthalazin-2(1H)-yl)-2-(hydroxymethyl)phenyl]-1H-indazole-7-carboxamide, 2-{3-[3-amino-7-(trifluoromethyl)-1H-indazol-5-yl]-2-(hydroxymethyl)phenyl}-6-tert-butyl-8-fluorophthalazin-1(2H)-one, 3-amino-5-[3-(6-tert-butyl-8-fluoro-1-oxophthalazin-2(1H)-yl)-2-(hydroxymethyl)phenyl]-1-methyl-1H-indazole-7-carboxamide, 2-[3-{3-amino-7-[1-(1-methylethyl)-1H-pyrazol-4-yl]-1H-indazol-5-yl}-2-(hydroxymethyl)phenyl]-6-tert-butyl-8-fluorophthalazin-1(2H)-one, 3-amino-5-(3-{[(4-tert-butyl-2-fluorophenyl)carbonyl]amino}-2-methylphenyl)-1H-indazole-7-carboxamide, 3-amino-5-[3-({[2-fluoro-4-(2,2,2-trifluoro-1,1-dimethylethyl)phenyl]carbonyl}amino)-2-methylphenyl]-1H-indazole-7-carboxamide, 2-{3-[3-amino-7-(1-methyl-1H-pyrazol-4-yl)-1H-indazol-5-yl]-2-(hydroxymethyl)phenyl}-6-tert-butyl-8-fluorophthalazin-1(2H)-one, 2-[3-(3-amino-7-pyridin-3-yl-1H-indazol-5-yl)-2-(hydroxymethyl)phenyl]-6-tert-butyl-8-fluorophthalazin-1(2H)-one, 3-amino-5-[3-(6-tert-butyl-8-fluoro-1-oxophthalazin-2(1H)-yl)-2-(hydroxymethyl)phenyl]-N-methyl-1H-indazole-7-carboxamide, 2-{3-[3-amino-1-(pyridin-4-ylmethyl)-1H-indazol-5-yl]-2-(hydroxymethyl)phenyl}-6-tert-butyl-8-fluorophthalazin-1(2H)-one, N-{3-[3-amino-7-(1-methyl-1H-pyrazol-4-yl)-1H-indazol-5-yl]-2-methylphenyl}-4-tert-butylbenzamide, 2-{3-[3-amino-7-(morpholin-4-ylcarbonyl)-1H-indazol-5-yl]-2-(hydroxymethyl)phenyl}-6-tert-butyl-8-fluorophthalazin-1(2H)-one, N-{3-[3-amino-7-(1-methyl-1H-pyrazol-4-yl)-1H-indazol-5-yl]-2-methylphenyl}-4-tert-butyl-2-fluorobenzamide, 3-amino-5-[3-(6-tert-butyl-8-fluoro-1-oxo-3,4-dihydroisoquinolin-2(1H)-yl)-2-(hydroxymethyl)phenyl]-1H-indazole-7-carboxamide, 2-[3-{3-amino-7-[1-(1-methylethyl)-1H-pyrazol-3-yl]-1H-indazol-5-yl}-2-(hydroxymethyl)phenyl]-6-tert-butyl-8-fluorophthalazin-1(2H)-one, N-{3-[3-amino-7-(1-methyl-1H-pyrazol-4-yl)-1H-indazol-5-yl]-2-(hydroxymethyl)phenyl}-4,5,6,7-tetrahydro-1-benzothiophene-2-carboxamide, 2-[3-(3-amino-7-phenyl-1H-indazol-5-yl)-2-(hydroxymethyl)phenyl]-6-tert-butyl-8-fluorophthalazin-1(2H)-one, 2-[3-(3-amino-1H-pyrazolo[4,3-b]pyridin-5-yl)-2-(hydroxymethyl)phenyl]-6-tert-butyl-8-fluorophthalazin-1(2H)-one, 2-[3-(3-amino-1H-pyrazolo[3,4-c]pyridin-5-yl)-2-(hydroxymethyl)phenyl]-6-tert-butyl-8-fluorophthalazin-1(2H)-one, 2-(3-(3-amino-7-(pyridin-2-yl)-1H-indazol-5-yl)-2-(hydroxymethyl)phenyl)-6-(tert-butyl)-8-fluorophthalazin-1(2H)-one, 2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)acetic acid, 2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)-2-methylpropanoic acid, 2-(3-(3-amino-7-(1-(tetrahydro-2H-pyran-4-yl)-1H-pyrazol-4-yl)-1H-indazol-5-yl)-2-(hydroxymethyl)phenyl)-6-(tert-butyl)-8-fluorophthalazin-1(2H)-one, 2-(3-(3-amino-7-(1-(2-methoxyethyl)-1H-pyrazol-4-yl)-1H-indazol-5-yl)-2-(hydroxymethyl)phenyl)-6-(tert-butyl)-8-fluorophthalazin-1(2H)-one, 2-(3-(3-amino-7-(1,3-dimethyl-1H-pyrazol-4-yl)-1H-indazol-5-yl)-2-(hydroxymethyl)phenyl)-6-(tert-butyl)-8-fluorophthalazin-1(2H)-one, and 2-(3-(3-amino-7-(4,5,6,7-tetrahydropyrazolo[1,5-a]pyridin-3-yl)-1H-indazol-5-yl)-2-(hydroxymethyl)phenyl)-6-(tert-butyl)-8-fluorophthalazin-1(2H)-one, a pharmaceutically acceptable salt thereof.

Utilities

The compounds having Formula (I) and pharmaceutical compositions thereof can be used to treat or prevent a variety of conditions, diseases or disorders mediated by Bruton's Tyrosine kinase (Btk). Such Btk-mediated conditions, diseases or disorders include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; and (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula (I) and salts thereof for use in therapy, and particularly in the treatment of disorders, diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In one embodiment, the present invention provides for the use of a compound of Formula (I), or a pharmaceutically acceptable salt thereof for the manufacture of a medicament for the treatment of a Btk-mediated disorder.

In another embodiment, the present invention provides methods of regulating, modulating, or inhibiting Btk for the prevention and/or treatment of disorders related to unregulated or inappropriate Btk activity.

In a further embodiment, the present invention provides a method for treating a subject suffering from a disorder mediated by Btk, which comprises administering to said subject a compound of Formula (I) or a pharmaceutically acceptable salt thereof in an amount effective to treat the Btk-mediated disorder.

A further aspect of the invention resides in the use of a compound of Formula (I) or a pharmaceutically acceptable salt thereof for the manufacture of a medicament to be used for the treatment of chronic B cell disorders in which T cells play a prominent role.

Thus, the compounds according to the invention may be used in therapies to treat or prevent Bruton's Tyrosine Kinase (Btk) mediated diseases, conditions and disorders. Btk mediated diseases, conditions and disorders as used herein, mean any disease, condition or disorder in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g., rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g., hemolytic anemia, aplasic anemia, idiopathic thrombocytopenia, chronic idiopathic thrombocytopenic purpura (ITP), and neutropenia), autoimmune gastritis, and autoimmune inflammatory bowel diseases (e.g., ulcerative colitis and Crohn's disease), irritable bowel syndrome, host versus graft disease, allograft rejection, chronic thyroiditis, Graves' disease, Sjogren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g., Behcet's disease), ANCA-associated and other vasculitudes, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g., chronic obstructive pulmonary disease) and other inflammatory or obstructive disease on airways.

Allergies that may be treated or prevented include, among others, allergies to foods, food additives, insect poisons, dust mites, pollen, animal materials and contact allergans, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula (I) or pharmaceutically acceptable salts may be used for the treatment of B cell lymphomas resulting from chronic active B cell receptor signaling.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role inimmunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Combination Therapy

Included herein are methods of treatment and/or pharmaceutical compositions in which at least one compound of Formula (I) or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-CS monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing Btk have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

Btk has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving Btk and/or its substrates (Vassilev et al., J. Biol. Chem. 1998, 274, 1646-1656).

It has also been discovered that Btk inhibitors are useful as chemosensitizing agents, and, thus, are useful in combination with other chemotherapeutic agents, in particular, drugs that induce apoptosis. Examples of other chemotherapeutic agents that can be used in combination with chemosensitizing Btk inhibitors include topoisomerase I inhibitors (camptothecin or topotecan), topoisomerase II inhibitors (e.g., daunomycin and etoposide), alkylating agents (e.g., cyclophosphamide, melphalan and BCNU), tubulin directed agents (e.g., taxol and vinblastine), and biological agents (e.g., antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852)

The compound(s) of Formula (I) and the other pharmaceutically active agent(s) may be administered together or separately and, when administered separately this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula (I) may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula (I) or a pharmaceutically acceptable salt thereof together with $beta_2$-adrenoreceptor agonist and an anti-inflammatory corticosteroid. Preferably this combination is for treatment and/or prophylaxis of asthma, COPD or allergic rhinitis. The $beta_2$-adrenoreceptor agonist and/or the anti-inflammatory corticosteroid can be as described above and/or as described in WO 03/030939 A1. Representative examples of such a "triple" combination are a compound of Formula (I) or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer, a compound of Formula (I) may be combined with one or more of an anticancer agents. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such asantisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradeca-dienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinasesand cdk and cdc kinase inhibitors and are specifically exemplified by 7-hydroxystaurosporin, flavopiridol, CYC202 (Cyclacel) and BMS-387032; (15) Btk inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'—O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosphl and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula (I) include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent, carrier or excipient represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Pharmaceutical Compositions

While it is possible that, for use in therapy, a compound of Formula (I), as well as salts, solvates and physiological functional derivatives thereof, may be administered as the raw chemical, it is possible to present the active ingredient as a pharmaceutical composition. Accordingly, the invention further provides a pharmaceutical composition which comprises a compound of Formula (I) and salts, solvates and physiological functional derivatives thereof, and one or more pharmaceutically acceptable carriers, diluents, or excipients. The compounds of the Formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula (I), or salts, solvates and physiological functional derivatives thereof, with one or more pharmaceutically acceptable carriers, diluents or excipients.

Routes of Administration

Pharmaceutical compositions of the present invention may be presented in unit dose forms containing a predetermined amount of active ingredient per unit dose. Such a unit may contain, for example, 5 μg to 1 g, preferably 1 mg to 700 mg, more preferably 5 mg to 100 mg of a compound of the Formula (I), depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g., injection liquids in predetermined amounts, for example in sealed vials and ampoules, and may also be stored in a freeze dried (lyophilized) condition requiring only the addition of sterile liquid carrier, e.g., water, prior to use.

Mixed with such pharmaceutically acceptable auxiliaries, e.g., as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g., as an injection preparation, in the form of a solution, suspension, emulsion, or as a spray, e.g., a nasal spray.

For making solid dosage units, the use of conventional additives such as fillers, colorants, polymeric binders and the like is contemplated. In general, any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula (I), and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula (I) is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula (I) or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula (I) or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device(GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula (I) or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula (I) or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

| Injectable Suspension (I.M.) | mg/mL |
|---|---|
| Compound of Formula (I) | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula (I) | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula (I) | 25 |
| Lactose Powder | 573.5 |
| Magnesium Stearate | 1.5 |
| | 600 |

| Aerosol | Per canister |
|---|---|
| Compound of Formula (I) | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula (I), the nature of the formulation, and the route of administration, and will ultimately be at the discretion of the attendant physician or veterinarian. However, an effective amount of a compound of Formula (I) for the treatment of diseases or conditions associated with inappropriate Btk activity, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula (I) per se.

In general parenteral administration requires lower dosages than other methods of administration which are more dependent upon absorption. However, a dosage for humans preferably contains 0.0001-25 mg of a compound of Formula (I) or pharmaceutically acceptable salts thereof per kg body weight. The desired dose may be presented as one dose or as multiple subdoses administered at appropriate intervals throughout the day. The dosage as well as the regimen of administration may differ between a female and a male recipient.

General Synthesis

The compounds of the present invention can be prepared by methods well known in the art of organic chemistry. See, for example, J. March, '*Advanced Organic Chemistry*' 4th Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' 3rd Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

The compounds of Formula (I) can be prepared by the general synthetic routes shown in the scheme below.

Scheme 1

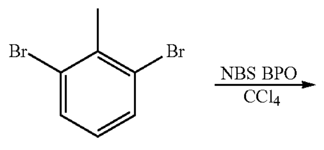

ii

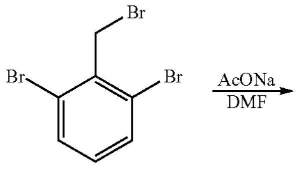

iii

-continued

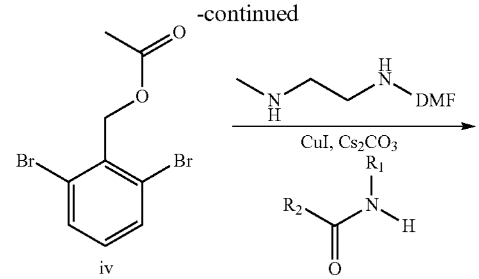

iv v

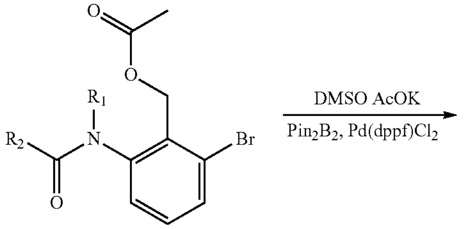

vi

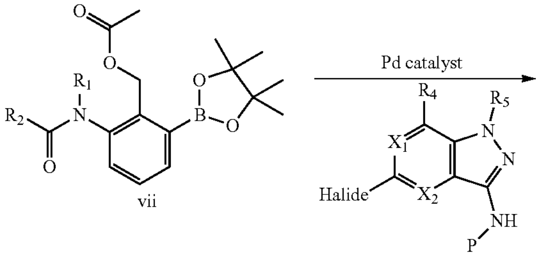

vii

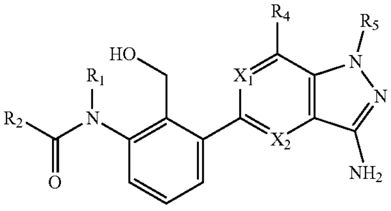

Fromula (I)

2,6-Dibromotoluene ii can be brominated on the benzylic carbon under radical reaction conditions to provide 2,6-dibromobenzyl bromide iii, which is then converted to acetateintermediate iv by reacting with sodium acetate in DMF. One of the bromo moieties in intermediateiv can selectively couple with amide v, which coupling is catalyzed by copper (I) iodide with base to provide intermediate vi. The bromo moiety in intermediate vi is then converted to boronpinacolate intermediate vii. Suzuki coupling of intermediate vii with readily prepared protected aminoindazole analogs viii catalyzed by palladium catalyst, followed by deprotection provide compounds of Formula (I).

The following abbreviations are used throughout the application with respect to chemical terminology:

$Ac_2O$ Acetic anhydride
AcOK Potassium acetate
aq Aqueous
ATP Adenosine triphosphate
Boc tert-butyloxycarbonyl
$Boc_2O$ Di-tert-butyl dicarbonate
BPO Benzoyl peroxide
BSA Bovine serum albumin
2-BuOH 2-Butanol
Cbz Benzyloxycarbonyl
Cbz-Cl Benzylchloroformate Brij-35 2-Dodecoxyethanol
$CDCl_3$ Deuterochloroform
$CD_3OD$ Tetradeuteromethanol
CDI 1,1'-Carbonyl diimidazole
dba Dibenzylideneacetone
DCM Dichloromethane
DIPEA N,N-Diisopropylethylamine
DMAP 4-Dimethylaminopyridine
DMF N,N-Dimethylformamide
DMSO Dimethyl sulfoxide
dppf 1,1'-Bis(diphenylphosphino)ferrocene
DTT Dithiothreitol
EDTA Ethylenediaminetetraacetic acid
EGTA Ethylene glycol tetraacetic acid
$Et_2O$ Diethylether
$Et_3N$ Triethylamine
EtOAc Ethyl acetate
EtOH Ethanol
HATU 1-[Bis(dimethylamino)methylene]-1H-1,2,3-triazolo [4,5-b]pyridinium 3-oxid hexafluorophosphate
Hepes 2-[4-(2-Hydroxyethyl)piperazin-1-yl]ethanesulfonic acid
HOAc Acetic acid
HPLC High Pressure Liquid Chromatography
i-PrOH 2-Propanol
KOAc Potassium acetate
LCMS Liquid Chromatography/Mass Spectrometry
LDA Lithium diisopropylamide
LiHMDS Lithium hexamethyldisilazide
MeCN Acetonitrile
MeI Iodomethane
MeOH Methanol
NBS N-bromosuccinimide
n-BuLi n-Butyllithium
NMP N-Methyl-2-pyrrolidone
Pd/C Palladium-on-carbon
$Pd(dppf)Cl_2$ 1,1'-Bis(diphenylphosphino)ferrocene palladium (II) chloride,
$Pd(OAc)_2$ Palladium(II) acetate
PE Petroleum ether
Ph Phenyl
Pin pinacol
$Pin_2B_2$ Bispinacolatediborone
PPTS Pyridinium p-toluenesulfonate
Prep-HPLC Preparative HPLC
PyBOP O-Benzotriazole-1-yl-oxy-trispyrrolidinophosphonium
rt Room Temperature
Rt Retention time
satd. Saturated
SFC Supercritical fluid chromatography
TBAF Tetrabutylammonium fluoride
TBSCl tert-Butyldimethylsilyl chloride
TEA Triethylamine
TFA Trifluoroacetic acid
THF Tetrahydrofuran
TMEDA Tetramethylethylenediamine
V:V volume/volume
Xantphos 4,5-Bis(diphenylphosphino)-9,9-dimethylxanthene
X-Phos 2-Dicyclohexylphosphino-2',4',6'-triisopropylbiphenyl The invention is illustrated by the following examples.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da. and scanned with a step rate of 0.2 Da., and the capillary voltage was set to 5000 V. $N_2$ gas was used for nebulisation.

LC-MS spectrometer (Waters) Detector: PDA (200-320 nm), Mass detector: ZQ and Eluent: A: acetonitrile with 0.05% trifluoroacetic acid, B: acetronitrile/water=1/9 (v/v) with 0.05% trifluoroacetic acid.

Method A:

Sample Info: Easy-Access Method: '1-Short_TFA_Pos'

Method Info: B222 Column Agilent SBC (3.0×50 mm, 1.8 μm); Flow 1.0 mL/min; solvent A: $H_2O$-0.1% TFA;

solvent B: MeCN-0.1% TFA;

GRADIENT TABLE: 0 min:10% B, 0.3 min:10% B, 1.5 min: 95% B, 2.70 min: 95% B, 2.76 min:10% B stop time 3.60 min, PostTime 0.70 min.

Method B:

Sample Info: Easy-Access Method: '1_Fast'

Method Info: A330 Column Agilent Zorbax SB-C18 (2.1×30 mm, 3.5 μm); Flow 2.0 mL/min;

solvent A: $H_2O$-0.1% TFA;

solvent B: MeCN-0.1% TFA;

GRADIENT TABLE: 0.01 min:10% B, 1.01 min:95% B, 1.37 min:95% B, 1.38 min:10% B, stop time 1.7 min, PostTime=OFF Proton nuclear magnetic resonance ($^1H$ NMR) spectra and carbon-13 nuclear magnetic resonance ($^{13}C$ NMR) spectra were recorded on spectrometersat the frequencies in the solvents indicated and referenced totetramethylsilane (TMS). Chemical shifts (δ) are reported in parts per million (ppm). Coupling constants (J) are reported in Hertz (Hz). The followingabbreviations are used: s (singlet), br s (broad singlet), d (doublet), t(triplet), q (quartet), and m (multiplet).

Intermediate 1

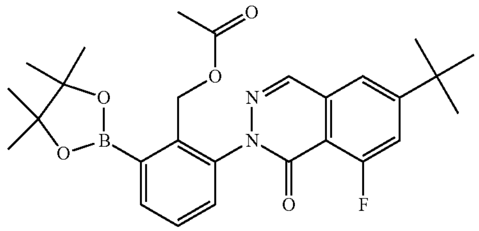 [SMILES: CC(=O)OCc1c(B2OC(C)(C)C(C)(C)O2)cccc1-n1ncc2cc(C(C)(C)C)cc(F)c2c1=O]

2-(6-(tert-butyl)-8-fluoro-1-oxophthalazin-2(1H)-yl)-6-(4,4,5,5-tetramethyl-1,3,2-dioxaborolan-2-yl)benzyl acetate

Step 1: 4-(tert-butyl)-N-(1-hydroxy-2-methylpropan-2-yl)benzamide

Into a 2000-mL round-bottom flask purged and maintained with an inert atmosphere of nitrogen was placed 4-tert-butylbenzoic acid (500 g, 2.81 mol, 1.00 equiv) and thionyl chloride (500 g, 4.20 mol, 1.50 equiv). The reaction mixture was heated to 80° C. for 4 hours. The solution was cooled and concentrated under vacuum. The residue was dissolved in DCM (500 mL) and then added dropwise to a solution of 2-amino-2-methylpropan-1-ol (625 g, 7.01 mol, 2.50 equiv) in dichloromethane (1000 g, 11.77 mol, 4.20 equiv) cooled at 0° C. The resulting solution was stirred for an additional 1 hour at room temperature. The reaction mixture was poured into 1 L of water. The organic phase was separated. The aqueous phase was extracted with 3×1 L of DCM. The organic phase was combined, washed with 1 L of brine, dried over sodium sulfate, filtered and concentrated under vacuum. This resulted in 4-tert-butyl-N-(1-hydroxy-2-methylpropan-2-yl)benzamide as a solid.

Step 2: 2-(4-(tert-butyl)phenyl)-4,4-dimethyl-4,5-dihydrooxazole

Into a 2000-mL round-bottom flask purged and maintained with an inert atmosphere of nitrogen was placed 4-tert-butyl-N-(1-hydroxy-2-methylpropan-2-yl)benzamide (500 g, 2.01 mol, 1.00 equiv), and thionyl chloride (500 mL). The resulting solution was stirred for 10 minutes at 80° C. The resulting mixture was cooled and concentrated under vacuum. The residue was diluted with 2 L of ice water and then 2 L of EtOAc. The pH value of the solution was adjusted to 7 with aq. sodium hydroxide (25%). The organic layer was collected. The aqueous phase was extracted with 2×2 L of ethyl acetate. The organic layers were combined, washed with 1×1 L of brine, dried over anhydrous sodium sulfate and concentrated under vacuum. The residue was applied onto a silica gel column and eluted with ethyl acetate/petroleum ether (1:100-1:10). This resulted in 2-(4-tert-butylphenyl)-4,4-dimethyl-4,5-dihydro-1,3-oxazole as a solid.

Step 3: 5-(tert-butyl)-2-(4,4-dimethyl-4,5-dihydrooxazol-2-yl)benzaldehyde

Into a 20-L 4-necked round-bottom flask purged and maintained with an inert atmosphere of nitrogen was placed a solution of 2-(4-tert-butylphenyl)-4,4-dimethyl-4,5-dihydro-1,3-oxazole (997 g, 4.31 mol, 1.00 equiv) in tetrahydrofuran (5 L). This was followed by the addition of n-BuLi (2.07 L) at −78° C. The resulting solution was stirred for 4 hours at −20° C. To this was added N,N-dimethylformamide (1.5 L) at −78° C. The resulting solution was stirred for an additional 1 hour at −20° C. The reaction was then quenched by pouring into 5 L of a saturated aq. sodium bicarbonate. The organic layer was collected. The aqueous phase was extracted with ethyl acetate. The organic layers were combined, washed with 2×3 L of saturated brine, dried over anhydrous sodium sulfate and concentrated under vacuum. This resulted in 5-tert-butyl-2-(4,4-dimethyl-4,5-dihydro-1,3-oxazol-2-yl)benzaldehyde(crude) as an oil.

Step 4: 2-(4-(tert-butyl)-2-(1,3-dioxan-2-yl)phenyl)-4,4-dimethyl-4,5-dihydrooxazole Into a 3-L 4-necked round-bottom flask was placed 5-tert-butyl-2-(4,4-dimethyl-4,5-dihydro-1,3-oxazol-2-yl)benzaldehyde (300 g, 1.16 mol, 1.00 equiv) at room temperature. This was followed by the addition of propane-1,3-diol (270 g, 3.55 mol, 3.00 equiv), toluene (1.5 L), and PPTS (15 g, 0.05 equiv). The resulting solution was stirred for overnight at 130° C. and the water was separated. The reaction was cooled to room temperature and quenched by the addition of 1 L of aq. sodium bicarbonate. The resulting solution was extracted with 2×2 L of ethyl acetate. The organic layers were combined, dried over anhydrous sodium sulfate and concentrated under vacuum. The crude product was purified with silica gel column eluted with EtOAc/PE (1:100-1:20). This resulted in 2-[4-tert-butyl-2-(1,3-dioxan-2-yl)phenyl]-4,4-dimethyl-4,5-dihydro-1,3-oxazole as a solid.

Step 5: 2-(4-(tert-butyl)-2-(1,3-dioxan-2-yl)-6-fluorophenyl)-4,4-dimethyl-4,5-dihydrooxazole Into a 20-L 4-necked round-bottom flask was placed a solution of 2-[4-tert-butyl-2-(1,3-dioxan-2-yl)phenyl]-4,4-dimethyl-4,5-dihydro-1,3-oxazole (550 g, 1.73 mol, 1.00 equiv) and TMEDA (500 g, 2.50 equiv) in tetrahydrofuran (5 L). This was followed by the addition of n-BuLi (1730 mL, 2.50 equiv) at −78° C. The resulting solution was stirred for 2 hours at −20° C. To this was added a solution of $(PhSO_2)_2$—N—F, (2.50 equiv) in tetrahydrofuran (3 L) at −78° C. The resulting solution was stirred for 1 hour at −20° C. and overnight at room temperature. The reaction was then quenched by the addition of 3 L of aq. $NH_4Cl$. The water layer was extracted with 2×2 L of ethyl acetate. The organic layers were combined, washed with 1×2 L of brine, dried over anhydrous sodium sulfate and concentrated under vacuum. The residue was purified by a silica gel column and eluted with ethyl acetate/petroleum ether (1:100-1:10). This resulted in 2-[4-tert-butyl-2-(1,3-dioxan-2-yl)-6-fluorophenyl]-4,4-dimethyl-4,5-dihydro-1,3-oxazole as a solid.

Step 6: 5-(tert-butyl)-7-fluoro-3-methoxyisobenzofuran-1(3H)-one

Into a 20-L 4-necked round-bottom flask was placed a solution of 2-[4-tert-butyl-2-(1,3-dioxan-2-yl)-6-fluorophenyl]-4,4-dimethyl-4,5-dihydro-1,3-oxazole (275 g, 819.88 mmol, 1.00 equiv) in methanol (4400 mL). This was followed by the addition of $H_2SO_4$ (50%, 3720 mL) dropwise with stirring. The resulting solution was stirred overnight at 85° C. Then it was cooled and concentrated under vacuum. The residual solution was diluted with 2 L of $H_2O$, and then extracted with dichloromethane. The organic layers were combined, washed with 1×1 L of brine, dried over anhydrous sodium sulfate and concentrated under vacuum. This provided 5-tert-butyl-7-fluoro-3-methoxy-1,3-dihydro-2-benzofuran-1-one as an oil.

Step 7: 6-(tert-butyl)-8-fluorophthalazin-1(2H)-one

Into a 10000-mL 4-necked round-bottom flask was placed acetic acid (3200 mL), and 5-tert-butyl-7-fluoro-3-methoxy-1,3-dihydro-2-benzofuran-1-one (300 g, 1.26 mol, 1.00 equiv). This was followed by the addition of hydrazine hydrate (1200 mL) dropwise with stirring at 0° C. The resulting solution was stirred for 2 hours at 50° C. and then cooled to room temperature. The resulting solution was diluted with 2 L of $H_2O$ and extracted with 3×1 L of DCM. The organic layers were combined, washed with 1×1 L of saturated brine, dried over anhydrous sodium sulfate and concentrated under vacuum. The solid was washed with 3×200 mL of EtOAc. This provided 6-tert-butyl-8-fluoro-1,2-dihydrophthalazin-1-one as a solid.

Step 8: 1,3-dibromo-2-(bromomethyl)benzene

Into a 20-L round-bottom flask was placed tetrachloromethane (8000 mL), 1,3-dibromo-2-methylbenzene (1400 g, 5.60 mol, 1.00 equiv), NBS (1100 g, 6.18 mol, 1.10 equiv), and benzoyl peroxide (135 g, 526.83 mmol, 0.09 equiv). The resulting solution was heated to reflux for 24 hours and then cooled to room temperature. The resulting mixture was washed with 3×5 L of water and 1×5 L of saturated brine. The organic phase was dried over anhydrous sodium sulfate and the crude product was purified by distillation. This provided 1,3-dibromo-2-(bromomethyl) benzene as a solid.

Step 9: 2,6-dibromobenzyl acetate

Into a 3000-mL 4-necked round-bottom flask was placed a solution of 1,3-dibromo-2-(bromomethyl)benzene (320 g, 973.16 mmol, 1.00 equiv) in N,N-dimethylformamide (1400 mL). This was followed by the addition of sodium acetate (412 g, 5.02 mol, 5.16 equiv), in portions. The resulting solution was stirred for 6 hours at 105° C. The reaction mixture was cooled to room temperature and diluted with 3000 mL of $H_2O$. The resulting solution was extracted with 2×2000 mL of ethyl acetate. The organic layers were combined, washed with 1×1 L of water and 1×1 L of saturated brine, dried over anhydrous sodium sulfate and concentrated under vacuum. The residue was applied onto a silica gel column and eluted with ethyl acetate/petroleum ether (1:30). This provided (2,6-dibromophenyl)methyl acetate as an solid.

Step 10: 2-bromo-6-(6-(tert-butyl)-8-fluoro-1-oxophthalazin-2(1H)-yl)benzyl acetate Into a 20-L 4-necked round-bottom flask was placed N,N-dimethylformamide (3.6 L), 6-tert-butyl-8-fluoro-1,2-dihydrophthalazin-1-one (180 g, 817.28 mmol, 1.00 equiv), (2,6-dibromophenyl)methyl acetate (1260 g, 4.09 mol, 5.01 equiv), CuI (234 g, 1.23 mol, 1.50 equiv), $Cs_2CO_3$(533 g), and methyl[2-(methylamino)ethyl]amine (72 g, 816.78 mmol, 1.00 equiv). The resulting solution was stirred for 4 hours at 150° C. The reaction mixture was cooled to room temperature and diluted with 10 L of $H_2O$ and 10 L of ethyl acetate. The water phase was extracted with 2×5 L of ethyl acetate. The organic layers were combined, washed with 1×5 L of water and 1×5 L of saturated brine, dried over anhydrous sodium sulfate and concentrated under vacuum. The residue was applied onto a silica gel column and eluted with ethyl acetate/petroleum ether (1:4). This provided [2-bromo-6-(6-tert-butyl-8-fluoro-1-oxo-1,2-dihydrophthalazin-2-yl) phenyl]methyl acetate as a solid.

Step 11: 2-(6-(tert-butyl)-8-fluoro-1-oxophthalazin-2(1H)-yl)-6-(4,4,5,5-tetramethyl-1,3,2-dioxaborolan-2-yl)benzyl acetate Into a 10-L 4-necked round-bottom flask was placed DMSO (4 L), [2-bromo-6-(6-tert-butyl-8-fluoro-1-oxo-1,2-dihydrophthalazin-2-yl)phenyl]methyl acetate (74.8 g, 167.23 mmol, 1.00 equiv), bispinacolatediborone (50.9 g, 200.47 mmol, 1.20 equiv), AcOK (49.8 g, 535.48 mmol, 3.20 equiv), and Pd(dppf)$Cl_2$ (13.9 g, 19.00 mmol, 0.11 equiv). The resulting solution was stirred overnight at 80° C. The solution was cooled and diluted with 6 L of EtOAc, then washed with 2×5000 mL of $H_2O$. The water layer was extracted with 2×3000 mL of ethyl acetate. The organic layers were combined, washed with 2×3000 mL of water and 1×3000 mL of saturated brine, dried over anhydrous sodium sulfate and concentrated under vacuum. The residue was applied onto a silica gel column and eluted with ethyl acetate/petroleum ether (1:2). This provided [2-(6-tert-butyl-8-fluoro-1-oxo-1,2-dihydrophthalazin-2-yl)-6-(tetramethyl-1,3,2-dioxaborolan-2-yl)phenyl]methyl acetate as a solid. LC-MS (ES, m/z): 495 $(M+1)^+$. $^1$H-NMR (300 MHz, $CDCl_3$): δ 1.336 (12H, s), 1.414 (9H, s), 1.899 (3H, s), 5.309 (2H, s), 7.429-7.512 (4H, m), 7.941-7.971 (1H, m), 8.165-8.174 (1H, d, J=2.7 Hz) ppm.

Example 1

3-amino-5-[3-(6-tert-butyl-8-fluoro-1-oxophthalazin-2(1H)-yl)-2-(hydroxymethyl)phenyl]-1H-indazole-7-carboxylic acid

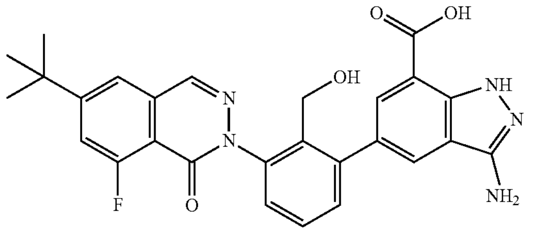 [SMILES: CC(C)(C)c1cc(F)c2c(=O)n(-c3cccc(-c4cc(C(=O)O)c5[nH]nc(N)c5c4)c3CO)ncc2c1]

Step 1: methyl 5-bromo-3-iodo-1H-indazole-7-carboxylate

To a solution of methyl 5-bromo-1H-indazole-7-carboxylate (3.2 g, 12.55 mmol) in DMF (60.0 mL) was added iodine (6.37 g, 25.09 mmol) and potassium hydroxide (2.64 g, 47.0 mmol). The reaction mixture was stirred for 1.5 h at 12° C., then quenched with satd. aq. $Na_2S_2O_3$ (10 mL) and extracted with EtOAc (20 mL×3). The combined organic layers were dried over anhydrous $Na_2SO_4$ and concentrated under vacuum to give methyl 5-bromo-3-iodo-1H-indazole-7-carboxylate as a solid. $^1$H NMR (400 MHz, $CDCl_3$): δ 11.46 (brs, 1H), 8.20 (s, 1H), 7.88 (s, 1H), 4.04 (s, 3H) ppm.

Step 2: 1-tert-butyl 7-methyl 5-bromo-3-iodo-1H-indazole-1,7-dicarboxylate

To a suspension of methyl 5-bromo-3-iodo-1H-indazole-7-carboxylate (5.23 g, 13.73 mmol) in DCM (100 mL) was added $Boc_2O$ (3.51 mL, 15.10 mmol) and DMAP (0.084 g, 0.686 mmol). The reaction mixture was stirred for 1 h at 12° C. (room temperature). The reaction mixture was concentrated under vacuum. The residue was purified by flash columnchromatography (40 g, EtOAc in PE: 0%-10%) to give 1-tert-butyl 7-methyl 5-bromo-3-iodo-1H-indazole-1,7-dicarboxylate as a solid. $^1$H NMR (400 MHz, $CDCl_3$): δ 11.46 (brs, 1H), 7.93 (s, 1H), 7.77 (s, 1H), 3.92 (s, 3H), 1.66 (s, 9H) ppm.

Step 3: 1-tert-butyl 7-methyl 5-bromo-3-((diphenylmethylene)amino)-1H-indazole-1,7-dicarboxylate To a solution of 1-tert-butyl 7-methyl 5-bromo-3-iodo-1H-indazole-1,7-dicarboxylate (2.0 g, 4.16 mmol) in dioxane (40 mL) was added diphenylmethanimine (0.753 g, 4.16 mmol), $Pd_2(dba)_3$ (0.761 g, 0.831 mmol), Xantphos (0.481 g, 0.831 mmol) and $Cs_2CO_3$ (4.06 g, 12.47 mmol). The reaction mixture was stirred for 15 min at 100° C. under microwave irradiation, then concentrated under vacuum. The residue was purified by flash column chromatography (40 g, EtOAc in PE: 0%-7%) to give 1-tert-butyl 7-methyl 5-bromo-3-((diphenylmethylene)amino)-1H-indazole-1,7-dicarboxylate as an oil. $^1$H NMR (400 MHz, $CDCl_3$) δ 7.87

(s, 1H), 7.73 (s, 1H), 7.60-7.43 (m, 5H), 7.31-7.27 (m, 5H), 3.90 (s, 3H), 1.58 (s, 9H) ppm.

Step 4: 1-tert-butyl 7-methyl 5-(2-(acetoxymethyl)-3-(6-(tert-butyl)-8-fluoro-1-oxophthalazin-2(1H)-yl) phenyl)-3-((diphenylmethylene)amino)-1H-indazole-1,7-dicarboxylate To a solution of 1-tert-butyl 7-methyl 5-bromo-3-((diphenylmethylene)amino)-1H-indazole-1,7-dicarboxylate (300 mg, 0.561 mmol) in dioxane (2 mL) and water (0.2 mL) was added 2-(6-(tert-butyl)-8-fluoro-1-oxophthalazin-2(1H)-yl)-6-(4,4,5,5-tetramethyl-1,3,2-dioxaborolan-2-yl)benzyl acetate (416 mg, 0.842 mmol), $Pd_2(dba)_3$ (103 mg, 0.112 mmol), dicyclohexyl(2',4',6'-triisopropyl-[1,1'-biphenyl]-2-yl)phosphine (53.5 mg, 0.112 mmol) and $K_3PO_4$ (357 mg, 1.684 mmol). The reaction mixture was stirred for 30 min at 125° C. under microwaveirradiation. The reaction mixture was poured into water (50 mL) and extracted with EtOAc (20 mL×2). The combined organic layers were dried over anhydrous $Na_2SO_4$ and concentrated in vacuo. The residue was purified by flash column chromatography (EtOAc in DCM: 0-20%) to give 1-tert-butyl 7-methyl 5-(2-(acetoxymethyl)-3-(6-(tert-butyl)-8-fluoro-1-oxophthalazin-2(1H)-yl) phenyl)-3-((diphenylmethylene)amino)-1H-indazole-1,7-dicarboxylate as a solid. $^1H$ NMR (400 MHz, $CDCl_3$) δ 7.56-7.37 (m, 10H), 7.33-7.21 (m, 8H), 4.79 (s, 2H), 3.90 (s, 3H), 1.80 (s, 3H), 1.60 (s, 9H), 1.41 (s, 9H) ppm.

Step 5: methyl 5-(2-(acetoxymethyl)-3-(6-(tert-butyl)-8-fluoro-1-oxophthalazin-2(1H)-yl)phenyl)-3-amino-1H-indazole-7-carboxylate To a solution of 1-tert-butyl 7-methyl 5-(2-(acetoxymethyl)-3-(6-(tert-butyl)-8-fluoro-1-oxophthalazin-2(1H)-yl) phenyl)-3-((diphenylmethylene)amino)-1H-indazole-1,7-dicarboxylate (367 mg, 0.447 mmol) in DCM (40 mL) was added HCl/dioxane (4 M, 40 mL, 160 mmol). The reaction mixture was stirred for 20 h at 20° C.-30° C. The residue was diluted with EtOAc (50 mL) and washed with aq.$NaHCO_3$ (20 mL×3), brine (20 mL×2), dried over anhydrous $Na_2SO_4$ and concentrated under vacuum. The residue was purified by flash column chromatography (20 g, MeOH in DCM: 0%-3%) to give methyl 5-(2-(acetoxymethyl)-3-(6-(tert-butyl)-8-fluoro-1-oxophthalazin-2(1H)-yl)phenyl)-3-amino-1H-indazole-7-carboxylate as an oil. $^1H$ NMR (400 MHz, $CDCl_3$) δ 10.18 (brs, 1H), 8.23-8.11 (m, 2H), 7.84 (s, 1H), 7.61-7.37 (m, 6H), 4.95 (s, 2H), 4.21 (brs, 2H), 3.99 (s, 3H), 1.86 (s, 3H), 1.42 (s, 9H) ppm.

Step 6: 3-amino-5-(3-(6-(tert-butyl)-8-fluoro-1-oxophthalazin-2(1H)-yl)-2-(hydroxymethyl)phenyl)-1H-indazole-7-carboxylic acid To a solution of methyl 5-(2-(acetoxymethyl)-3-(6-(tert-butyl)-8-fluoro-1-oxophthalazin-2(1H)-yl)phenyl)-3-amino-1H-indazole-7-carboxylate (195 mg, 0.350 mmol) in THF (10 mL) was added 2N LiOH (10 mL, 20.00 mmol). Then the reaction mixture was stirred for 4 h at 25° C.-30° C. The mixture was poured into water (20 mL) and acidified with 1N HCl to pH=4-5. Then the aqueous layer was extracted with EtOAc (20 mL×2). The combined organic layers were dried over anhydrous $Na_2SO_4$ and concentrated in vacuo. The residue was purified by Prep-HPLC to give 3-amino-5-(3-(6-(tert-butyl)-8-fluoro-1-oxophthalazin-2(1H)-yl)-2-(hydroxymethyl)phenyl)-1H-indazole-7-carboxylic acid was obtained as a solid. MS-ESI: 502.1 (M+1)+, (method A Rt: 2.753 min). $^1H$ NMR (400 MHz, DMSO-$d_6$) δ 11.78 (brs, 1H), 8.51 (d, J=2.5 Hz, 1H), 8.09 (d, J=1.5 Hz, 1H), 8.00 (d, J=1.5 Hz, 1H), 7.87 (d, J=1.5 Hz, 1H), 7.74 (d, J=13.1 Hz, 1H), 7.56-7.49 (m, 1H), 7.45-7.39 (m, 2H), 4.30 (s, 2H), 1.38 (s, 9H) ppm.

Example 2

2-[3-(3-amino-6-methyl-1H-indazol-5-yl)-2-(hydroxymethyl)phenyl]-6-tert-butyl-8-fluorophthalazin-1(2H)-one

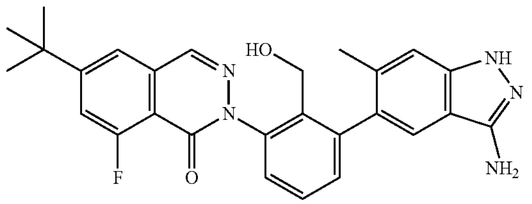 [SMILES: Cc1cc2[nH]nc(N)c2cc1-c1cccc(-n2ncc3cc(C(C)(C)C)cc(F)c3c2=O)c1CO]

Step 1: 5-amino-2-fluoro-4-methylbenzonitrile

To a solution of 5-bromo-4-fluoro-2-methylaniline (1.0 g, 4.90 mmol) in NMP (15 mL) was added copper cyanide (0.878 g, 9.80 mmol) and CuI (0.933 g, 4.90 mmol) under $N_2$. The reaction mixture was stirred for 30 min at 195° C. under microwave irradiation. The reaction mixture was poured into water (100 mL) and extracted with EtOAc (50 mL×2). The combined organic layers were filtered and the filtrate was concentrated to give 5-amino-2-fluoro-4-methylbenzonitrile, which was used to the next step directly. $^1H$ NMR (400 MHz, $CDCl_3$): δ 6.90 (d, J=9.2 Hz, 1H), 6.80 (d, J=5.6 Hz, 1H), 3.69 (brs, 2H), 2.20 (s, 3H) ppm.

Step 2: 5-bromo-2-fluoro-4-methylbenzonitrile

To a suspension of CuBr (1.166 g, 8.13 mmol) in acetonitrile (50 mL) at 0° C. was added tert-butyl nitrite (1.071 g, 10.39 mmol, followed by 5-amino-2-fluoro-4-methylbenzonitrile (1.00 g, 6.66 mmol) (in acetonitrile, 50 mL). After addition, the mixture was stirred at 25° C.-30° C. for 18 h. The above mixture was poured to EtOAc (50 mL). The organic layer was washed with aq. $Na_2CO_3$ (30 mL×3), brine (30 mL×2) and dried over anhydrous $Na_2SO_4$. Then the organic layer was concentrated under vacuum and the residue was purified by flash column chromatography (EtOAc in PE=0-10%) to give 5-bromo-2-fluoro-4-methylbenzonitrile. $^1HNMR$ (400 MHz, $CDCl_3$) δ 7.70 (d, J=5.9 Hz, 1H), 7.06 (d, J=9.4 Hz, 1H), 2.40 (s, 3H) ppm.

Step 3: 5-bromo-6-methyl-1H-indazol-3-amine

To a solution of 5-bromo-2-fluoro-4-methylbenzonitrile (473 mg, 2.210 mmol) in ethanol (25 mL) was added hydrazine (0.408 mL, 11.05 mmol). The mixture was stirred at 120° C. for 2 days in a sealed tube, then poured into water (100 mL) and extracted with EtOAc (50 mL×2). The combined organic layers were dried over anhydrous $Na_2SO_4$ and concentrated in vacuo to give 5-bromo-6-methyl-1H-indazol-3-amine. $^1HNMR$ (400 MHz, DMSO-$d_6$): δ 11.38 (brs, 1H), 7.93 (s, 1H), 7.18 (s, 1H), 5.36 (brs, 2H), 2.36 (s, 3H) ppm.

Step 4: 2-(3-amino-6-methyl-1H-indazol-5-yl)-6-(6-(tert-butyl)-8-fluoro-1-oxophthalazin-2(1H)-yl)benzyl acetate To a solution of 5-bromo-6-methyl-1H-indazol-3-amine (150 mg, 0.664 mmol) in dioxane (1 mL) and water (0.1 mL) was added 2-(6-(tert-butyl)-8-fluoro-1-oxophthalazin-2(1H)-yl)-6-(4,4,5,5-tetramethyl-1,3,2-dioxaborolan-2-yl)benzyl acetate (394 mg, 0.796 mmol), dicyclohexyl(2',4',6'-triisopropyl-[1,1'-biphenyl]-2-yl)phosphine (63.3 mg, 0.133 mmol), $Pd_2(dba)_3$ (122 mg, 0.133 mmol) and $K_3PO_4$ (423 mg, 1.991 mmol) under $N_2$. The reaction mixture was stirred for 30 min at 125° C. in microwave. The reaction mixture was poured into water (50 mL) and extracted with EtOAc (20 mL×2). The combined organic layers were dried over anhydrous $Na_2SO_4$ and concentrated in vacuo. The residue was purified via flash column chromatography (20 g, MeOH in DCM: 0%-5%) to give 2-(3-amino-6-methyl-1H-indazol-5-yl)-6-(6-(tert-butyl)-8-fluoro-1-oxophthalazin-2(1H)-yl) benzyl acetate. $^1$HNMR (400 MHz, $CDCl_3$) δ 9.08 (brs, 1H), 8.21 (d, J=1.6 Hz, 1H), 7.58-7.28 (m, 6H), 7.17 (s, 1H), 4.94 (d, J=12.1 Hz, 1H), 4.76 (d, J=12.1 Hz, 1H), 4.22-4.02 (brs, 2H), 2.19 (s, 3H), 1.71 (s, 3H), 1.41 (s, 9H) ppm.

Step 5: 2-(3-(3-amino-6-methyl-1H-indazol-5-yl)-2-(hydroxymethyl)phenyl)-6-(tert-butyl)-8-fluorophthalazin-1(2H)-one To a solution of 2-(3-amino-6-methyl-1H-indazol-5-yl)-6-(6-(tert-butyl)-8-fluoro-1-oxophthalazin-2(1H)-yl)benzyl acetate (107 mg, 0.208 mmol) in THF (5.0 mL) was added 2N LiOH (5 mL, 10.00 mmol). Then the reaction mixture was stirred for 24 h at rt, then poured into water (50 mL) and extracted with EtOAc (20 mL×2). The combined organic layers were dried over $Na_2SO_4$, filtered and concentrated. The residue was purified by prepHPLC to give 2-(3-(3-amino-6-methyl-1H-indazol-5-yl)-2-(hydroxymethyl)phenyl)-6-(tert-butyl)-8-fluorophthalazin-1(2H)-one. $^1$HNMR (400 MHz, $CD_3OD$) δ 8.46 (s, 1H), 7.82 (s, 1H), 7.77-7.64 (m, 2H), 7.60-7.51 (m, 1H), 7.46 (d, J=7.8 Hz, 1H), 7.37-7.30 (m, 2H), 4.35 (d, J=11.7 Hz, 1H), 4.15 (d, J=12.1 Hz, 1H), 2.23 (s, 3H), 1.43 (s, 9H) ppm.

Example 3

3-amino-5-[3-(6-tert-butyl-8-fluoro-1-oxophthalazin-2(1H)-yl)-2-(hydroxymethyl)phenyl]-1H-indazole-7-carboxamide

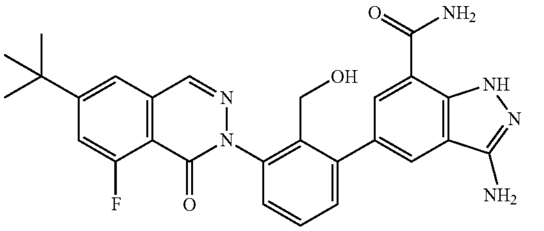 [SMILES: CC(C)(C)c1cc(F)c2c(=O)n(-c3cccc(-c4cc(C(N)=O)c5[nH]nc(N)c5c4)c3CO)ncc2c1]

To a solution of 3-amino-5-(3-(6-(tert-butyl)-8-fluoro-1-oxophthalazin-2(1H)-yl)-2-(hydroxymethyl)phenyl)-1H-indazole-7-carboxylic acid (8.0 mg, 0.016 mmol) in DMF (2.0 mL) was added HATU (12.13 mg, 0.032 mmol), $NH_4Cl$ (2.56 mg, 0.048 mmol) and triethylamine (6.46 mg, 0.064 mmol) under $N_2$. The reaction mixture was stirred at 25° C.-30° C. for 20 h, then purified by prepHPLC directly to give 3-amino-5-(3-(6-(tert-butyl)-8-fluoro-1-oxophthalazin-2(1H)-yl)-2-(hydroxymethyl)phenyl)-1H-indazole-7-carboxamide. $^1$HNMR (400 MHz, $CD_3OD$) δ 8.47 (brs, 1H), 8.14 (d, J=7.8 Hz, 2H), 7.83 (s, 1H), 7.69 (d, J=12.9 Hz, 1H), 7.63-7.50 (m, 2H), 7.46 (d, J=7.0 Hz, 1H), 4.41 (brs, 2H), 1.43 (s, 9H) ppm.

Example 4

2-{3-[3-amino-7-(trifluoromethyl)-1H-indazol-5-yl]-2-(hydroxymethyl)phenyl}-6-tert-butyl-8-fluorophthalazin-1(2H)-one

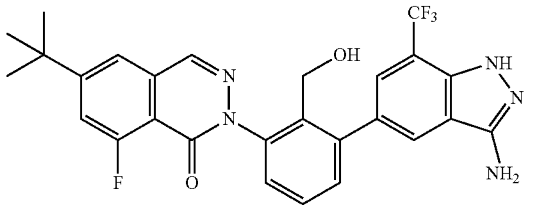 [SMILES: CC(C)(C)c1cc(F)c2c(=O)n(-c3cccc(-c4cc(C(F)(F)F)c5[nH]nc(N)c5c4)c3CO)ncc2c1]

Step 1: 5-bromo-2-fluoro-3-(trifluoromethyl)benzaldehyde

To a solution of diisopropylamine (2.499 g, 24.69 mmol) in THF (100 mL) was added butyllithium (9.88 mL, 24.69 mmol) dropwise at −78° C. under $N_2$. After addition, the reaction mixture was stirred for 30 min. Then 4-bromo-1-fluoro-2-(trifluoromethyl)benzene (5.0 g, 20.58 mmol) and N,N-dimethylformamide (2.256 g, 30.9 mmol) was added. The mixture was stirred for 1 h at −78° C., then quenched with aq. $NH_4Cl$ (300 mL) and extracted with EtOAc (100 mL×2). The combined organic layers were dried over anhydrous $Na_2SO_4$ and concentrated in vacuo to give 5-bromo-2-fluoro-3-(trifluoromethyl)benzaldehyde. $^1$HNMR (400 MHz, $CDCl_3$) δ 10.33 (s, 1H), 8.18 (d, J=3.1 Hz, 1H), 7.97 (d, J=3.9 Hz, 1H) ppm.

Step 2: (E)-5-bromo-2-fluoro-3-(trifluoromethyl) benzaldehyde oxime

To a solution of 5-bromo-2-fluoro-3-(trifluoromethyl) benzaldehyde (5.58 g, 20.59 mmol) in EtOH (60 ml) was added hydroxylamine, HCl (1.717 g, 24.71 mmol) and sodium acetate (2.027 g, 24.71 mmol). Then the mixture was stirred for 18 h at 9° C.-10° C. (room temperature). The reaction mixture was quenched with water (100 mL) and extracted with EtOAc (100 mL×2). The combined organic layers were dried over anhydrous $Na_2SO_4$ and concentrated in vacuo to give crude (E)-5-bromo-2-fluoro-3-(trifluoromethyl)benzaldehyde oxime, which was used to the next step directly. $^1$HNMR (400 MHz, $CDCl_3$) δ 8.67 (brs, 1H), 8.33 (s, 1H), 8.13-8.04 (m, 1H), 7.74 (d, J=3.9 Hz, 1H) ppm.

Step 3: 5-bromo-2-fluoro-3-(trifluoromethyl)benzonitrile

A solution of (E)-5-bromo-2-fluoro-3-(trifluoromethyl) benzaldehyde oxime (3.0 g, 10.49 mmol) in $Ac_2O$ (40 mL) was stirred at 140° C. for 20 h. The reaction mixture was quenched with aq. $Na_2CO_3$ (100 mL) and extracted with EtOAc (20 mL×2). The combined organic layers were dried over anhydrous $Na_2SO_4$ and concentrated in vacuo. The residue was purified by combi flash (EtOAc in PE: 0%-3%) to give 5-bromo-2-fluoro-3-(trifluoromethyl)benzonitrile. $^1$HNMR (400 MHz, $CDCl_3$) δ 7.97 (t, J=6.1 Hz, 2H) ppm.

Step 4:
5-bromo-7-(trifluoromethyl)-1H-indazol-3-amine

To a solution of 5-bromo-2-fluoro-3-(trifluoromethyl) benzonitrile (1.14 g, 4.25 mmol) in ethanol (40 mL) was added hydrazine (0.785 mL, 21.27 mmol). Then the mixture was stirred at 120° C. for 2 days in a sealed tube. The reaction mixture was poured into water (100 mL) and extracted with EtOAc (30 mL×2). The combined organic layers were dried over $Na_2SO_4$, filtered and concentrated to give 5-bromo-7-(trifluoromethyl)-1H-indazol-3-amine. $^1$HNMR (400 MHz, DMSO-$d_6$) δ2.19 (s, 1H), 8.27 (s, 1H), 7.69 (s, 1H), 5.75 (s, 2H) ppm.

Step 5:
5-bromo-7-(trifluoromethyl)-1H-indazol-3-amine

To a solution of 5-bromo-7-(trifluoromethyl)-1H-indazol-3-amine (300 mg, 1.071 mmol) in dioxane (2 mL) and water (0.2 mL) was added 2-(6-(tert-butyl)-8-fluoro-1-oxophthalazin-2(1H)-yl)-6-(4,4,5,5-tetramethyl-1,3,2-dioxaborolan-2-yl)benzyl acetate (636 mg, 1.286 mmol), dicyclohexyl(2',4',6'-triisopropyl-[1,1'-biphenyl]-2-yl)phosphine (102 mg, 0.214 mmol), $Pd_2(dba)_3$ (196 mg, 0.214 mmol) and $K_3PO_4$ (682 mg, 3.21 mmol) under $N_2$. Then the reaction mixture was stirred for 30 min at 125° C. in microwave. The reaction mixture was poured into water (50 mL) and extracted with EtOAc (20 mL×2). The combined organic layers were dried over $Na_2SO_4$ and concentrated. The residue was purified by flash column chromatography (MeOH in DCM: 0%-3%) to give 2-(3-amino-7-(trifluoromethyl)-1H-indazol-5-yl)-6-(6-(tert-butyl)-8-fluoro-1-oxophthalazin-2(1H)-yl)benzyl acetate. $^1$HNMR (400 MHz, $CDCl_3$) δ 9.44 (brs, 1H), 8.21 (d, J=2.0 Hz, 1H), 7.85-7.70 (m, 2H), 7.64-7.41 (m, 5H), 4.92 (s, 2H), 4.26 (brs, 2H), 1.93-1.79 (m, 3H), 1.41 (s, 9H) ppm.

Step 6: 2-(3-(3-amino-7-(trifluoromethyl)-1H-indazol-5-yl)-2-(hydroxymethyl)phenyl)-6-(tert-butyl)-8-fluorophthalazin-1(2H)-one To a solution of 2-(3-amino-7-(trifluoromethyl)-1H-indazol-5-yl)-6-(6-(tert-butyl)-8-fluoro-1-oxophthalazin-2(1H)-yl)benzyl acetate (332 mg, 0.585 mmol) in THF (10 mL) was added 2N LiOH (15 mL, 30.0 mmol). Then the reaction mixture was stirred for 18 h at 25° C.-30° C. The mixture was poured into water (50 mL) and extracted with EtOAc (20 mL×2). The combined organic layers were dried over $Na_2SO_4$, filtered and concentrated. The residue was purified by Prep-HPLC to give 2-(3-(3-amino-7-(trifluoromethyl)-1H-indazol-5-yl)-2-(hydroxymethyl)phenyl)-6-(tert-butyl)-8-fluorophthalazin-1(2H)-one. $^1$HNMR (400 MHz, $CD_3OD$) δ 8.48 (d, J=2.0 Hz, 1H), 8.16 (s, 1H), 7.98 (s, 1H), 7.84 (s, 1H), 7.69 (d, J=12.9 Hz, 1H), 7.64-7.55 (m, 1H), 7.49 (dd, J=7.2, 18.2 Hz, 2H), 4.39 (brs, 2H), 1.44 (s, 9H) ppm.

Example 5

3-amino-5-[3-(6-tert-butyl-8-fluoro-1-oxophthalazin-2 (1H)-yl)-2-(hydroxymethyl)phenyl]-1-methyl-1H-indazole-7-carboxamide

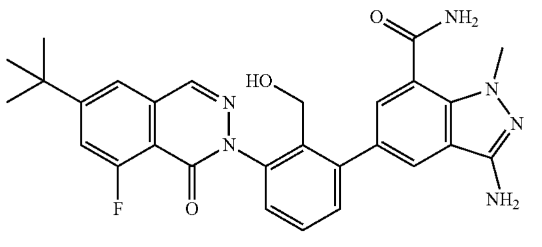 [SMILES: Cn1nc(N)c2cc(-c3cccc(-n4ncc5cc(C(C)(C)C)cc(F)c5c4=O)c3CO)cc(C(N)=O)c21]

Step 1: methyl
5-bromo-3-iodo-1H-indazole-7-carboxylate

To a suspension of 1-tert-butyl 7-methyl 5-bromo-3-iodo-1H-indazole-1,7-dicarboxylate (700 mg, 1.455 mmol) in DCM (10 mL) was added HCl/dioxane (4 M, 10 mL, 40.0 mmol). Then the reaction mixture was stirred for 4 h at 25-30° C. The solvent was removed to give methyl 5-bromo-3-iodo-1H-indazole-7-carboxylate. $^1$HNMR (DMSO-$d_6$, 400 MHz) δ 8.06 (d, J=1.6 Hz, 1H), 7.93 (s, 1H), 3.95-3.95 (s, 3H) ppm.

Step 2: methyl
5-bromo-3-iodo-1-methyl-1H-indazole-7-carboxylate

To a solution of methyl 5-bromo-3-iodo-1H-indazole-7-carboxylate (554 mg, 1.454 mmol) in DMF (15 mL) was added MeI (0.335 mL, 5.35 mmol) and $Cs_2CO_3$ (1895 mg, 5.82 mmol). Then the reaction mixture was stirred for 18 h at 25-30° C., then poured into water (100 mL) and extracted with EtOAc (30 mL×2). The combined organic layers were dried over $Na_2SO_4$ and concentrated to give methyl 5-bromo-3-iodo-1-methyl-1H-indazole-7-carboxylate. MS: 394.9/396.9 $(M+1)^+$. (MethodB, Rt: 1.230 min). $^1$H NMR ($CDCl_3$, 400 MHz) δ 8.09 (d, J=1.2 Hz, 1H), 7.81 (d, J=1.6 Hz, 1H), 4.27 (s, 3H), 3.99 (s, 3H) ppm.

Step 3: methyl 5-bromo-3-((diphenylmethylene) amino)-1-methyl-1H-indazole-7-carboxylate To a solution of methyl 5-bromo-3-iodo-1-methyl-1H-indazole-7-carboxylate (370 mg, 0.937 mmol) in dioxane (3 mL) were added diphenylmethanimine (170 mg, 0.937 mmol), Xantphos (108 mg, 0.187 mmol), $Pd_2(dba)_3$ (172 mg, 0.187 mmol) and $Cs_2CO_3$ (916 mg, 2.81 mmol). The reaction mixture was stirred for 15 min at 100° C. in a microwave reactor, then poured into water (50 mL) and extracted with EtOAc (30 mL×3). The combined organic layers were dried over $Na_2SO_4$ and concentrated. The residue was purified by flash column chromatography (MeOH in DCM: 0%-3%) to give crude methyl 5-bromo-3-((diphenylmethylene)amino)-1-methyl-1H-indazole-7-carboxylate. MSESI: 448.3/450.1 $(M+1)^+$. (Method B; Rt: 1.342 min).

Step 4: methyl 5-(2-(acetoxymethyl)-3-(6-(tert-butyl)-8-fluoro-1-oxophthalazin-2(1H)-yl)phenyl)-3-((diphenylmethylene)amino)-1-methyl-1H-indazole-7-carboxylate To a solution of methyl 5-bromo-3-((diphenylmethylene) amino)-1-methyl-1H-indazole-7-carboxylate (420 mg, 0.937 mmol) in dioxane (3 mL) and water (0.3 mL) were added 2-(6-(tert-butyl)-8-fluoro-1-oxophthalazin-2(1H)-yl)-6-(4,4,5,5-tetramethyl-1,3,2-dioxaborolan-2-yl)benzyl acetate (556 mg, 1.124 mmol), Xantphos (89 mg, 0.187 mmol), $Pd_2(dba)_3$ (172 mg, 0.187 mmol) and $K_3PO_4$ (597 mg, 2.81 mmol) under $N_2$. The reaction mixture was stirred for 30 min at 125° C. in a microwave reactor, then poured into water (50 mL) and extracted with EtOAc (20 mL×2). The combined organic layers were dried over $Na_2SO_4$ and concentrated. The residue was purified by flash column chromatography (MeOH in DCM: 0%-3%) to give methyl 5-(2-(acetoxymethyl)-3-(6-(tert-butyl)-8-fluoro-1-oxophthalazin-2(1H)-yl)phenyl)-3-((diphenylmethylene)amino)-1-methyl-1H-indazole-7-carboxylate. MS-ESI: 736.2 $(M+1)^+$. (Method B; Rt: 1.391 min).

Step 5: methyl 5-(2-(acetoxymethyl)-3-(6-(tert-butyl)-8-fluoro-1-oxophthalazin-2(1H)-yl)phenyl)-3-amino-1-methyl-1H-indazole-7-carboxylate To a solution of methyl 5-(2-(acetoxymethyl)-3-(6-(tert-butyl)-8-fluoro-1-oxophthalazin-2(1H)-yl)phenyl)-3-((diphenylmethylene)amino)-1-methyl-1H-indazole-7-carboxylate (640 mg, 0.870 mmol) in DCM (10 mL) was added HCl/dioxane (4 M, 10 mL, 40.0 mmol). Then the reaction mixture was stirred for 20 h at 20-30° C. The reaction mixture was concentrated, then satd. aq. $NaHCO_3$ (50 mL) was added. Then the mixture was extracted with EtOAc (30 mL×2). The combined organic layers were dried over $Na_2SO_4$ and concentrated. The residue was purified by flash column chromatography (MeOH in DCM: 0%-3%) to give crude methyl 5-(2-(acetoxymethyl)-3-(6-(tert-butyl)-8-fluoro-1-oxophthalazin-2(1H)-yl)phenyl)-3-amino-1-methyl-1H-indazole-7-carboxylate as an oil. MS-ESI: 572.3 $(M+1)^+$. (Method B; Rt: 1.172 min).

Step 6: 3-amino-5-(3-(6-(tert-butyl)-8-fluoro-1-oxophthalazin-2(1H)-yl)-2-(hydroxymethyl)phenyl)-1-methyl-1H-indazole-7-carboxylic acid To a solution of methyl 5-(2-(acetoxymethyl)-3-(6-(tert-butyl)-8-fluoro-1-oxophthalazin-2(1H)-yl)phenyl)-3-amino-1-methyl-1H-indazole-7-carboxylate (293 mg, 0.513 mmol) in THF (10 mL) was added aq.LiOH (2 M, 15 mL, 30.0 mmol). The reaction mixture was stirred for 18 h at 25-30° C. LCMS showed the reaction was complete. The mixture was poured into water (50 mL) and extracted with EtOAc (20 mL×2). The combined organic layers were dried over $Na_2SO_4$, filtered and concentrated to give crude 3-amino-5-(3-(6-(tert-butyl)-8-fluoro-1-oxophthalazin-2(1H)-yl)-2-(hydroxymethyl)phenyl)-1-methyl-1H-indazole-7-carboxylic acid, which was used to the next step directly. MS-ESI: 516.2 $(M+1)^+$. (Method B; Rt: 1.164 min).

Step 7: 3-amino-5-(3-(6-(tert-butyl)-8-fluoro-1-oxophthalazin-2(1H)-yl)-2-(hydroxymethyl)phenyl)-1-methyl-1H-indazole-7-carboxamide To a solution of 3-amino-5-(3-(6-(tert-butyl)-8-fluoro-1-oxophthalazin-2(1H)-yl)-2-(hydroxymethyl)phenyl)-1-methyl-1H-indazole-7-carboxylic acid (264 mg, 0.512 mmol) in DMF (4.0 mL) were added HATU (389 mg, 1.024 mmol), $NH_4Cl$ (82 mg, 1.536 mmol) and triethylamine (207 mg, 2.048 mmol) under $N_2$. Then the reaction mixture was stirred at 25-30° C. for 20 h, then purified by Prep-HPLC directly to give 3-amino-5-(3-(6-(tert-butyl)-8-fluoro-1-oxophthalazin-2(1H)-yl)-2-(hydroxymethyl)phenyl)-1-methyl-1H-indazole-7-carboxamide was obtained as a solid. MS-ESI: 515.1 $(M+1)^+$. (Method A; Rt: 2.614 min). $^1H$ NMR (400 MHz, $CD_3OD$) δ 8.48 (d, J=2.3 Hz, 1H), 7.97 (s, 1H), 7.84 (s, 1H), 7.79 (s, 1H), 7.70 (d, J=13.3 Hz, 1H), 7.62-7.50 (m, 2H), 7.45 (d, J=7.0 Hz, 1H), 4.42 (br. s., 2H), 3.94 (s, 3H), 1.55-1.39 (s, 9H) ppm.

Example 6

2-[3-{3-amino-7-[1-(1-methylethyl)-1H-pyrazol-4-yl]-1H-indazol-5-yl}-2-(hydroxymethyl)phenyl]-6-tert-butyl-8-fluorophthalazin-1(2H)-one

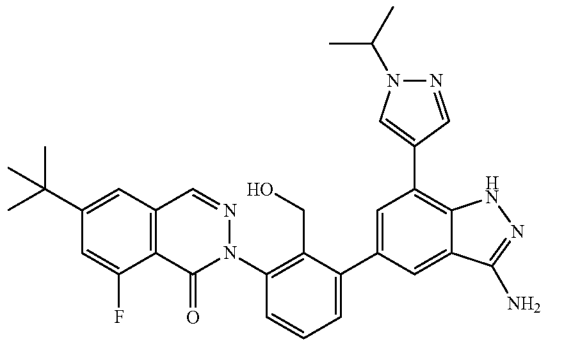 [SMILES: CC(C)n1cc(-c2cc(-c3cccc(-n4ncc5cc(C(C)(C)C)cc(F)c5c4=O)c3CO)cc3c(N)n[nH]c23)cn1]

Step 1: 4-bromo-1-isopropyl-1H-pyrazole

To a solution of 4-bromo-1H-pyrazole (3.5 g, 24.0 mmol) in DMF (10 mL) were added 2-iodopropane (4.89 g, 28.8 mmol), $K_2CO_3$(3.31 g, 24.0 mmol). The mixture was stirred at 80° C. for 16 hours, then cooled to room temperature, diluted with water (20 mL) and extracted with ethyl acetate (20 mL×3). The combined organic layers were washed with 1N $NaHCO_3$ (30 mL), brine (20 mL×2), dried over anhydrous sodium sulfate and concentrated. The residue was purified by column chromatography on silica gel (eluting with petroleum ether/EtOAc=100:1-8:1) to give 4-bromo-1-isopropyl-1H-pyrazole as anoil. MS ESI: 189 and 191 $(M+1)^+$. (Method B; Rt:1.155 min).

Step 2: 1-isopropyl-4-(4,4,5,5-tetramethyl-1,3,2-dioxaborolan-2-yl)-1H-pyrazole

To a solution of 4-bromo-1-isopropyl-1H-pyrazole (1.00 g, 5.29 mmol) in 1,4-dioxane (20 mL) were added $B_2(Pin)_2$(2.69 g, 10.6 mmol), KOAc (1.04 g, 10.6 mmol) and $Pd(dppf)Cl_2$ (345 mg, 0.529 mmol). The mixture was stirred at 100° C. under $N_2$ for 16 hours. The mixture was cooled to room temperature and concentrated. The residue was purified by column chromatography on silica gel (elute by PE/EtOAc=100:1-5:1) to give 1-isopropyl-4-(4,4,5,5-tetramethyl-1,3,2-dioxaborolan-2-yl)-1H-pyrazole as a solid. MS ESI: 237 $(M+1)^+$. (Method B; Rt:1.165 min). H NMR (400 MHz, $CD_3OD$) δ 7.86 (s, 1H), 7.66 (s, 1H), 4.60-4.46 (m, 1H), 1.48 (d, J=6.7 Hz, 6H), 1.31 (s, 12H).

Step 3: 5-bromo-7-(1-isopropyl-1H-pyrazol-4-yl)-1H-indazol-3-amine

To a solution of 5-bromo-7-iodo-1H-indazol-3-amine (250 mg, 0.740 mmol) in 1,4-dioxane (8 mL) and $H_2O$ (2 mL) was added 1-isopropyl-4-(4,4,5,5-tetramethyl-1,3,2-dioxaborolan-2-yl)-1H-pyrazole (262 mg, 1.11 mmol), $K_2CO_3$ (409 mg, 2.96 mmol) and $Pd(dppf)Cl_2$ (48.2 mg, 0.074 mmol) under $N_2$. The mixture was stirred at 40° C. under $N_2$ for 16 hours, then concentrated. The residue was purified by column chromatography on silica gel (eluting with PE/EtOAc=100:1-1:100) to give 5-bromo-7-(1-isopropyl-1H-pyrazol-4-yl)-1H-indazol-3-amine as a solid. MS ESI: 320 and 322 $(M+1)^+$. (Method B; Rt:0.982 min). $^1H$ NMR (400 MHz, DMSO-$d_6$) δ 10.72 (br. s., 1H), 7.57 (s, 1H), 7.22 (s, 1H), 6.95 (s, 1H), 6.76-6.68 (m, 1H), 4.67 (br. s., 2H), 3.67 (td, J=6.7, 13.3 Hz, 1H), 0.62 (d, J=6.7 Hz, 6H) ppm.

Step 4:2-(3-amino-7-(1-isopropyl-1H-pyrazol-4-yl)-1H-indazol-5-yl)-6-(6-(tert-butyl)-8-fluoro-1-oxophthalazin-2(1H)-yl)benzyl acetate To a solution of 5-bromo-7-(1-isopropyl-1H-pyrazol-4-yl)-1H-indazol-3-amine (110 mg, 0.344 mmol) in 1,4-dioxane (5 mL) and $H_2O$ (0.5 mL) was added 2-(6-(tert-butyl)-8-fluoro-1-oxophthalazin-2(1H)-yl)-6-(4,4,5,5-tetramethyl-1,3,2-dioxaborolan-2-yl)benzyl acetate (255 mg, 0.515 mmol), $K_3PO_4$(219 mg, 1.08 mmol), $Pd_2(dba)_3$ (63.2 mg, 0.069 mmol) and X-phos (32.8 mg, 0.069 mmol) under $N_2$ atmosphere. The mixture was stirred at 120° C. under $N_2$ for 30 min in a microwave reactor. The mixture was diluted with water (10 mL) and extracted with ethyl acetate (15 mL×2). The combined organic layers were washed with brine (20 mL×2), dried over anhydrous sodium sulfate and concentrated. The residue was purified by column chromatography on silica gel (elute by petroleum ether/EtOAc=100:1-100:1) to give 2-(3-amino-7-(1-isopropyl-1H-pyrazol-4-yl)-1H-indazol-5-yl)-6-(6-(tert-butyl)-8-fluoro-1-oxophthalazin-2 (1H)-yl)benzyl acetate as a solid. MS ESI: 608 $(M+1)^+$. $^1H$ NMR (400 MHz, $CD_3OD$ δ 8.49-8.32 (m, 1H), 8.20 (s, 1H), 8.01-7.89 (m, 1H), 7.80 (s, 1H), 7.67 (d, J=12.1 Hz, 1H), 7.61 (s, 1H), 7.59-7.55 (m, 2H), 7.45-7.33 (m, 1H), 6.89 (s, 1H), 5.00 (d, J=11.3 Hz, 2H), 4.58 (quin, J=6.6 Hz, 1H), 1.72 (s, 2H), 1.54 (d, J=6.7 Hz, 6H), 1.42 (s, 9H) ppm.

Example 7

3-amino-5-(3-{[(4-tert-butyl-2-fluorophenyl)carbonyl]amino}-2-methylphenyl)-1H-indazole-7-carboxamide

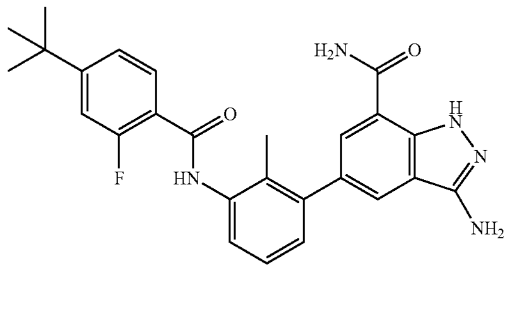 [SMILES: Cc1c(NC(=O)c2ccc(C(C)(C)C)cc2F)cccc1-c1cc(C(N)=O)c2[nH]nc(N)c2c1]

Step 1: 3-amino-5-bromo-1H-indazole-7-carbonitrile

To a suspension of 5-bromo-7-iodo-1H-indazol-3-amine (0.5 g, 1.480 mmol) in DMF (10 mL) were added zinc cyanide (0.090 g, 0.769 mmol) and $Pd(PPh_3)_4$ (0.137 g, 0.118 mmol). The mixture was heated to 110° C. for 18 h, then diluted with DCM (50 mL), and washed with water (15 mL) and brine (10 mL). The organic layer was dried over anhydrous sodium sulfate, purified with silica gel (PE/EtOAc=70/30) to give crude 3-amino-5-bromo-1H-indazole-7-carbonitrile as a solid. MS-ESI (m/z): 327.1/329.1 $(M+1)^+$ (Method B; Rt: 0.822 min).

Step 2:4-(tert-butyl)-2-fluorobenzoyl chloride

To a solution of 4-(tert-butyl)-2-fluorobenzoic acid (841 mg, 4.29 mmol) and DMF (3.32 μl, 0.043 mmol) in DCM (10 mL) was added dropwise oxalyl dichloride (2720 mg, 21.43 mmol), then the mixture was stirred at 18° C. for 3 h. The reaction mixture was concentrated to remove solvent and to give crude 4-(tert-butyl)-2-fluorobenzoyl chloride.

Step 3:4-(tert-butyl)-2-fluoro-N-(2-methyl-3-(4,4,5,5-tetramethyl-1,3,2-dioxaborolan-2-yl)phenyl)benzamide To a solution 4-(tert-butyl)-2-fluorobenzoyl chloride (920 mg, 4.29 mmol) in DCM (20 mL) was added pyridine (1017 mg, 12.86 mmol) and 2-methyl-3-(4,4,5,5-tetramethyl-1,3,2-dioxaborolan-2-yl)aniline (999 mg, 4.29 mmol), then the mixture was stirred at 18° C. for 2 h. The reaction mixture was purified with silica gel column chromatography (20 g, PE/EtOAc 85:15) to give 4-(tert-butyl)-2-fluoro-N-(2-methyl-3-(4,4,5,5-tetramethyl-1,3,2-dioxaborolan-2-yl)phenyl)benzamide. MS-ESI (m/z): 412.2 $(M+1)^+$(Method B; Rt: 1.615 min). $^1H$ NMR (400 MHz, $CDCl_3$) δ 8.45 (d, J=16.6 Hz, 1H), 8.22-8.11 (m, 2H), 7.63 (dd, J=1.1, 7.4 Hz, 1H), 7.35 (dd, J=1.8, 8.3 Hz, 1H), 7.29-7.24 (t, J=8 Hz, 1H), 7.19 (dd, J=1.8, 14.8 Hz, 1H), 2.56 (s, 3H), 1.36 (d, J=2.3 Hz, 21H) ppm.

Step 4: N-(3-(3-amino-7-cyano-1H-indazol-5-yl)-2-methylphenyl)-4-(tert-butyl)-2-fluorobenzamide To a mixture of 4-(tert-butyl)-2-fluoro-N-(2-methyl-3-(4,4,5,5-tetramethyl-1,3,2-dioxaborolan-2-yl)phenyl)benzamide (104 mg, 0.253 mmol) and 3-amino-5-bromo-1H-indazole-7-carbonitrile (40 mg, 0.169 mmol) in 1,4-dioxane (2 mL) and water (0.5 mL) were added potassium phosphate (107 mg, 0.506 mmol), X-Phos (16.09 mg, 0.034 mmol) and $Pd_2(dba)_3$ (15.45 mg, 0.017 mmol) under $N_2$. The suspension was stirred at 125° C. for 1 h in a microwave reactor. The reaction mixture was concentrated and purified by silica gel column chromatography (12 g, PE/THF 70:30~DCM/THF 50:50) to give N-(3-(3-amino-7-cyano-1H-indazol-5-yl)-2-methylphenyl)-4-(tert-butyl)-2-fluorobenzamide. MS-ESI (m/z): 442.2 $(M+1)^+$. Method B; Rt: 1.238 min).

Step 5: (1S,3S)-methyl 3-(8-amino-1-bromoimidazo[1,5-a]pyrazin-3-yl)-1,2,2-trimethylcyclopentanecarboxylate To a solution of N-(3-(3-amino-7-cyano-1H-indazol-5-yl)-2-methylphenyl)-4-(tert-butyl)-2-fluorobenzamide (31 mg, 0.070 mmol) in THF (5 mL) and water (1 mL) was added hydrido(dimethylphosphinous acid-kp)[hydrogen bis (dimethylphosphinito-kp)]platinum(II) (0.600 mg, 1.404 μmol), and then the mixture was stirred at 100° C. for 3 h. The reaction mixture was diluted with EtOAc (15 mL), washed with water (5 mL). The organic layer was separated and concentrated, the residue was purified via prep-HPLC (0.1% TFA) to give 3-amino-5-(3-(4-(tert-butyl)-2-fluorobenzamido)-2-methylphenyl)-1H-indazole-7-carboxamide. MS-ESI (m/z): 460.2 $(M+1)^+$, Method A: Rt: 2.536 min.

$^1H$ NMR (400 MHz, $CD_3OD$) δ=8.06 (d, J=1.3 Hz, 1H), 8.02 (d, J=1.3 Hz, 1H), 7.80 (t, J=8.0 Hz, 1H), 7.51 (d, J=7.5 Hz, 1H), 7.39 (dd, J=1.6, 8.2 Hz, 1H), 7.36-7.24 (m, 3H), 2.22 (s, 3H), 1.35 (s, 9H) ppm.

Example 8

3-amino-5-[3-({[2-fluoro-4-(2,2,2-trifluoro-1,1-dimethylethyl)phenyl]carbonyl}amino)-2-methylphenyl]-1H-indazole-7-carboxamide

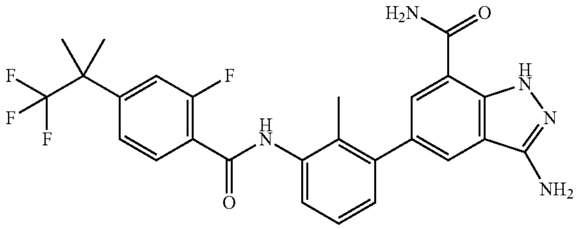 [SMILES: Cc1c(NC(=O)c2ccc(C(C)(C)C(F)(F)F)cc2F)cccc1-c1cc(C(N)=O)c2[nH]nc(N)c2c1]

Step 1:methyl 4-(1,1,1-trifluoro-2-methylpropan-2-yl)benzoate

To a solution of 1-bromo-4-(1,1,1-trifluoro-2-methylpropan-2-yl)benzene (2 g, 7.49 mmol) in MeOH (5 mL) and DMF (15 mL) was added TEA (3.13 mL, 22.46 mmol), DPPF (0.830 g, 1.498 mmol) and $Pd(OAc)_2$ (0.168 g, 0.749 mmol). The suspension was stirred at 80° C. under CO (50 psi) atmosphere for 70 hours. The reaction mixture was filtered and concentrated to remove solvent. The residue was then taken into EtOAc (100 mL), washed with water (20 mL×2) and brine (15 mL). The organic layer was dried over $Na_2SO_4$, filtered and purified with silica gel (PE/THF 90:10) to give methyl 4-(1,1,1-trifluoro-2-methylpropan-2-yl)benzoate. $^1H$ NMR (400 MHz, $CDCl_3$) δ 8.03 (d, J=8.2 Hz, 2H), 7.58 (d, J=8.2 Hz, 2H), 3.93 (s, 3H), 1.61 (s, 6H) ppm.

Step 2: 4-(1,1,1-trifluoro-2-methylpropan-2-yl)benzoic acid

To a solution of methyl 4-(1,1,1-trifluoro-2-methylpropan-2-yl)benzoate (1.25 g, 5.08 mmol) in MeOH (15 mL) was added KOH (0.285 g, 5.08 mmol), and then the mixture was stirred at 20° C. for 18 hours. The reaction mixture was concentrated to remove solvent and diluted with water (10 mL), and then pH adjusted to 2 with the addition of HCl aqueous (4 M), extracted DCM (15 mL×3). The organic layers were combined and dried over anhydrous sodium sulfate, filtered and concentrated to give 4-(1,1,1-trifluoro-2-methylpropan-2-yl)benzoic acid. $^1H$ NMR (400 MHz, $CDCl_3$) δ 8.11 (d, J=8.6 Hz, 2H), 7.58 (d, J=8.2 Hz, 2H), 1.61 (s, 6H) ppm.

Step 3: N-(1-hydroxy-2-methylpropan-2-yl)-4-(1,1,1-trifluoro-2-methylpropan-2-yl)benzamide To a solution of 4-(1,1,1-trifluoro-2-methylpropan-2-yl) benzoic acid (1.24 g, 5.34 mmol) in DCM (15 mL) containing DMF (2.067 μl, 0.027 mmol) was added oxalyl dichloride (2.033 g, 16.02 mmol). The mixture was stirred at 20° C. for 18 hours, then concentrated to give crude 4-(1,1,1-trifluoro-2-methylpropan-2-yl)benzoyl chloride as an oil. The above product in DCM (15 mL) was added to a solution of 2-amino-2-methylpropan-1-ol (0.476 g, 5.34 mmol) in DCM (15 mL) at −78° C. After addition, the mixture was stirred at −78° C. for 2 hours. The reaction suspension was filtered and the filtrate was purified with silica gel column chromatography (PE/THF 70:30) to give N-(1-hydroxy-2-methylpropan-2-yl)-4-(1,1,1-trifluoro-2-methylpropan-2-yl)benzamide as a solid. MS-ESI (m/z): 304.2 $(M+1)^+$(Method B; Rt: 1.078 min). $^1H$ NMR (400 MHz, $CDCl_3$) δ 7.73 (d, J=8.6 Hz, 2H), 7.57 (d, J=8.2 Hz, 2H), 3.71 (s, 2H), 1.60 (s, 6H), 1.42 (s, 6H) ppm.

Step 4:4,4-dimethyl-2-(4-(1,1,1-trifluoro-2-methylpropan-2-yl)phenyl)-4,5-dihydrooxazole A solution of N-(1-hydroxy-2-methylpropan-2-yl)-4-(1,1,1-trifluoro-2-methylpropan-2-yl)benzamide (1.63 g, 5.37 mmol) in $SOCl_2$ (10 mL) was stirred at 20° C. for 18 hours. The reaction mixture was concentrated. The residue was dissolved in water (15 mL), and the pH was adjusted to 10 with the addition of satd. $Na_2CO_3$. The mixture was extracted with t-butyl methyl ether (20 mL×3). The organic layers were combined and dried over anhydrous sodium sulfate, filtered and the filtrate was concentrated to give 4,4-dimethyl-2-(4-(1,1,1-trifluoro-2-methylpropan-2-yl) phenyl)-4,5-dihydrooxazole. MS-ESI (m/z): 286.1 $(M+1)^+$ (Method B; Rt: 1.098 min). $^1H$ NMR (400 MHz, $CDCl_3$) δ 7.93 (d, J=8.6 Hz, 2H), 7.54 (d, J=8.2 Hz, 2H), 4.12 (s, 2H), 1.60 (s, 6H), 1.39 (s, 6H) ppm.

Step 5:2-(2-fluoro-4-(1,1,1-trifluoro-2-methylpropan-2-yl)phenyl)-4,4-dimethyl-4,5-dihydrooxazole In an oven-dried 100 mL of three-necked round-bottomed flask with $N_2$ bubbler, a rubber septum and a magnetic stirring bar was placed 4,4-dimethyl-2-(4-(1,1,1-trifluoro-2-methylpropan-2-yl)phenyl)-4,5-dihydrooxazole (875 mg, 3.07 mmol) in THF (15 mL). To the reaction mixture at −60° C. was added TMEDA (2.78 mL, 18.40 mmol), followed by n-BuLi (7.36 mL, 18.40 mmol). The reaction mixture was then warmed to −20° C. slowly and stirred at this temperature for 2 hours. The mixture then was cooled to −60° C. again and a solution of N-fluoro-N-(phenylsulfonyl)benzenesulfonamide (5803 mg, 18.40 mmol) in THF (15 mL) was added dropwise. Then the mixture was allowed to warm to 20° C. for 15 hours. The reaction was quenched with satd. $NH_4Cl$ aqueous (20 mL). The mixture was extracted with EtOAc (20 mL×3), The organic layers were combined and dried over anhydrous sodium sulfate, purified with silica gel column chromatography (PE: EtOAc 90:10) to give crude 2-(2-fluoro-4-(1,1,1-trifluoro-2-methylpropan-2-yl)phenyl)-4,4-dimethyl-4,5-dihydrooxazole. MS-ESI (m/z):304.2 $(M+1)^+$(Method B; Rt: 0.832 min).

Step 6:2-fluoro-4-(1,1,1-trifluoro-2-methylpropan-2-yl)benzoic acid 2-(2-fluoro-4-(1,1,1-trifluoro-2-methylpropan-2-yl)phenyl)-4,4-dimethyl-4,5-dihydrooxazole (210 mg, 0.692 mmol) in conc. Aq. HCl (15 mL, 90 mmol) was stirred at 100° C. for 20 hours. The reaction mixture was cooled to 20° C. and then extracted with DCM (10 mL×3). The organic layers were combined and dried over anhydrous sodium sulfate, filtered and concentrated to give crude 2-fluoro-4-(1,1,1-trifluoro-2-methylpropan-2-yl)benzoic acid.

Step 7: 2-fluoro-N-(2-methyl-3-(4,4,5,5-tetramethyl-1,3,2-dioxaborolan-2-yl)phenyl)-4-(1,1,1-trifluoro-2-methylpropan-2-yl)benzamide To a solution of 2-fluoro-4-(1,1,1-trifluoro-2-methylpropan-2-yl)benzoic acid (150 mg, 0.600 mmol) in DCM (5 mL) were added DMF (1 drop) and oxalyl dichloride (380 mg, 3.00 mmol). Then the mixture was stirred at 20° C. for 18 hours. The reaction mixture was concentrated to give crude 2-fluoro-4-(1,1,1-trifluoro-2-methylpropan-2-yl)benzoyl chloride. The above product in DCM (15 mL) was then added to a mixture of 2-methyl-3-(4,4,5,5-tetramethyl-1,3,2-dioxaborolan-2-yl)aniline (140 mg, 0.599 mmol) and pyridine (47.4 mg, 0.599 mmol) in DCM (10 mL) at 0° C., then the mixture was stirred at 20° C. for 4 hours. The reaction mixture was diluted with DCM (30 mL) and washed with water (20 mL) and dried over anhydrous sodium sulfate, and purified using silica gel column chromatography (PE/THF 95:5) to give 2-fluoro-N-(2-methyl-3-(4,4,5,5-tetramethyl-1,3,2-dioxaborolan-2-yl)phenyl)-4-(1,1,1-trifluoro-2-methylpropan-2-yl)benzamide as a solid. MS-ESI (m/z): 466.2 $(M+1)^+$.

Step 8: N-(3-(3-amino-7-cyano-1H-indazol-5-yl)-2-methylphenyl)-2-fluoro-4-(1,1,1-trifluoro-2-methylpropan-2-yl)benzamide To a mixture of 2-fluoro-N-(2-methyl-3-(4,4,5,5-tetramethyl-1,3,2-dioxaborolan-2-yl)phenyl)-4-(1,1,1-trifluoro-2-methylpropan-2-yl)benzamide (58.9 mg, 0.127 mmol) and 3-amino-5-bromo-1H-indazole-7-carbonitrile (20 mg, 0.084 mmol) in 1,4-dioxane (2 mL) and water (0.5 mL) were added potassium phosphate (53.7 mg, 0.253 mmol), X-Phos (8.04 mg, 0.017 mmol), $Pd_2(dba)_3$ (7.73 mg, 8.44 μmol) under $N_2$. The suspension was stirred at 125° C. for 1 h in a microwave reactor. The reaction mixture was concentrated and purified with silica gel column chromatography (PE/THF 70:30~DCM/THF 50:50) to give N-(3-(3-amino-7-cyano-1H-indazol-5-yl)-2-methylphenyl)-2-fluoro-4-(1,1,1-trifluoro-2-methylpropan-2-yl)benzamide. MS-ESI (m/z): 496.2 $(M+1)^+$(Method B; Rt: 1.292 min).

Step 9: 3-amino-5-(3-(2-fluoro-4-(1,1,1-trifluoro-2-methylpropan-2-yl)benzamido)-2-methylphenyl)-1H-indazole-7-carboxamide To a solution of N-(3-(3-amino-7-cyano-1H-indazol-5-yl)-2-methylphenyl)-2-fluoro-4-(1,1,1-trifluoro-2-methylpropan-2-yl)benzamide (11.4 mg, 0.023 mmol) in THF (3 mL) and water (1 mL) was added hydrido(dimethylphosphinous acid-kp)[hydrogen bis (dimethylphosphinito-kp)] platinum(II) (0.197 mg, 0.460 μmol), and then the mixture was stirred at 100° C. for 3 hours before diluting with EtOAc (15 mL). The mixture was washed with water (5 mL). The organic layer was separated and concentrated to give a solid which was purified via Prep-HPLC to give 3-amino-5-(3-(2-fluoro-4-(1,1,1-trifluoro-2-methylpropan-2-yl)benzamido)-2-methylphenyl)-1H-indazole-7-carboxamide. MS-ESI (m/z): 514.0 $(M+1)^+$, Method A Rt: 2.835 min. $^1H$ NMR (400 MHz, $CD_3OD$) δ=8.05 (s, 1H), 8.02 (d, J=1.3 Hz, 1H), 7.86 (t, J=8.0 Hz, 1H), 7.55-7.44 (m, 3H), 7.37-7.26 (m, 2H), 2.23 (s, 3H), 1.62 (s, 6H) ppm.

Example 9

2-{3-[3-amino-7-(1-methyl-1H-pyrazol-4-yl)-1H-indazol-5-yl]-2-(hydroxymethyl)phenyl}-6-tert-butyl-8-fluorophthalazin-1(2H)-one

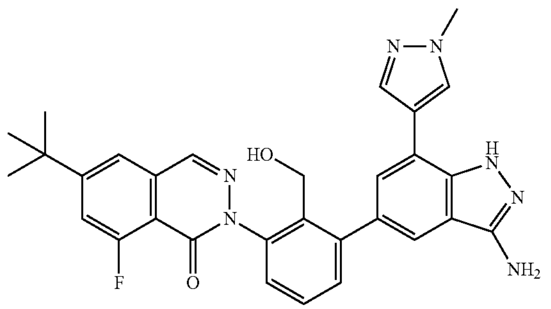 [SMILES: Cn1cc(-c2cc(-c3cccc(-n4ncc5cc(C(C)(C)C)cc(F)c5c4=O)c3CO)cc3c(N)n[nH]c23)cn1]

Step 1: 5-bromo-2-fluoro-3-iodobenzonitrile

To a solution of 2,2,6,6-tetramethylpiperidine (2.72 g, 19.25 mmol) in THF (25 mL) at −20° C. was added n-BuLi (7.70 mL, 19.25 mmol) dropwise over 0.5 h. The reaction was stirred at −10° C. for 1 h, and then was cooled to −70° C. The diethylzinc (21.00 mL, 21.00 mmol) was added, and the resulting solution was warmed to 0° C. over 0.5 h and stirred at this temperature for 1.5 hours. The solution was then recooled to −70° C., 5-bromo-2-fluorobenzonitrile (3.5 g, 17.50 mmol) in THF (10 mL) was added, and the resulting solution was stirred at −70° C. for 0.5 hour and at −30° C. for 3 hours. The solution was then recooled to −70° C. and iodine (13.32 g, 52.5 mmol) in THF (30 mL) was added. The reaction was left to warm to room temperature and stirred for 16 hours. The reaction was quenched with satd. $NaHSO_3$ aq. (3.5 mL) and then filtered. The solvent was removed under vacuum and the resulting residue was re-dissolved with EtOAc (100 mL). The organic layer was washed with satd. $NaHSO_3$ aq. solution (50 mL×2) and brine (50 mL), dried over $Na_2SO_4$, filtered and concentrated in vacuo to give the crude product, which was recrystallized with EtOAc/Pet. ether (50 mL, V/V=1/2) to give 5-bromo-2-fluoro-3-iodobenzonitrile. $^1H$ NMR (400 MHz, $CDCl_3$) δ 8.12 (dd, J=2.3, 5.1 Hz, 1H), 7.72 (dd, J=2.2, 4.9 Hz, 1H) ppm.

Step 2: 5-bromo-7-iodo-1H-indazol-3-amine

To a solution of 5-bromo-2-fluoro-3-iodobenzonitrile (4 g, 12.27 mmol) in THF (50 mL) was added hydrazine hydrate (1.493 mL, 30.7 mmol). The mixture was stirred at 85° C. for 16 hours. The mixture was cooled to room temperature and diluted with EtOAc (100 mL), the mixture was washed with water (30 mL) and brine (30 mL). The organic layer was dried over $Na_2SO_4$, filtered and concentrated in vacuo to give the 5-bromo-7-iodo-1H-indazol-3-amine. $^1H$ NMR (400 MHz, DMSO-$d_6$) δ 11.75 (br. s., 1H), 7.95 (s, 1H), 7.70 (s, 1H), 5.53 (br. s., 2H) ppm.

Step 3: 5-bromo-7-(1-methyl-1H-pyrazol-4-yl)-1H-indazol-3-amine

To a solution of 5-bromo-7-iodo-1H-indazol-3-amine (200 mg, 0.592 mmol) and 1-methyl-4-(4,4,5,5-tetramethyl-1,3,2-dioxaborolan-2-yl)-1H-pyrazole (148 mg, 0.710 mmol) in a mixed solvent of dioxane (6 mL) and water (1.5 mL) were added $K_2CO_3$ (327 mg, 2.367 mmol) and $PdCl_2$ (dppf) (43.3 mg, 0.059 mmol) under $N_2$. The mixture was stirred at 40° C. for 16 hours. The mixture was diluted with EtOAc (20 mL), and then washed with water (10 mL) and brine (10 mL). The organic layer was dried over $Na_2SO_4$, concentrated in vacuo to give the crude product, which was purified by flash column chromatography (MeOH in DCM=0%~5%) to give 5-bromo-7-(1-methyl-1H-pyrazol-4-yl)-1H-indazol-3-amine. $^1$H NMR (400 MHz, DMSO-$d_6$) δ 11.51 (s, 1H), 8.34 (s, 1H), 8.04 (s, 1H), 7.80 (s, 1H), 7.53 (s, 1H), 5.50 (br. s., 2H), 3.88 (s, 3H) ppm.

Step 4: 2-(3-amino-7-(1-methyl-1H-pyrazol-4-yl)-1H-indazol-5-yl)-6-(6-(tert-butyl)-8-fluoro-1-oxophthalazin-2(1H)-yl)benzyl acetate To a solution of 5-bromo-7-(1-methyl-1H-pyrazol-4-yl)-1H-indazol-3-amine (180 mg, 0.616 mmol) in a mixed solvent of dioxane (2.5 mL) and water (0.250 mL) were added 2-(6-(tert-butyl)-8-fluoro-1-oxophthalazin-2(1H)-yl)-6-(4,4,5,5-tetramethyl-1,3,2-dioxaborolan-2-yl)benzyl acetate (457 mg, 0.924 mmol), X-Phos (58.7 mg, 0.123 mmol), $Pd_2(dba)_3$ (113 mg, 0.123 mmol) and $K_3PO_4$ (392 mg, 1.848 mmol) under $N_2$. Then the reaction mixture was stirred for 30 min at 125° C. in a microwave reactor. The reaction mixture was poured into water (50 mL) and extracted with EtOAc (20 mL×2). The combined organic layers were dried over $Na_2SO_4$, filtered and concentrated. The residue was purified via flash column chromatography (MeOH in DCM: 0%-10%) to give 2-(3-amino-7-(1-methyl-1H-pyrazol-4-yl)-1H-indazol-5-yl)-6-(6-(tert-butyl)-8-fluoro-1-oxophthalazin-2(1H)-yl)benzyl acetate. $^1$H NMR (400 MHz, $CDCl_3$) □ 9.32 (s, 1H), 8.20 (s, 1H), 7.87 (s, 1H), 7.75 (s, 1H), 7.56-7.38 (m, 7H), 5.03 (br. s., 2H), 4.20 (br. s., 2H), 4.00 (s, 3H), 1.80 (s, 3H), 1.41 (s, 9H) ppm.

Step 5: 2-(3-(3-amino-7-(1-methyl-1H-pyrazol-4-yl)-1H-indazol-5-yl)-2-(hydroxymethyl)phenyl)-6-(tert-butyl)-8-fluorophthalazin-1(2H)-one To a solution of 2-(3-amino-7-(1-methyl-1H-pyrazol-4-yl)-1H-indazol-5-yl)-6-(6-(tert-butyl)-8-fluoro-1-oxophthalazin-2(1H)-yl)benzyl acetate (160 mg, 0.276 mmol) in THF (10 mL) was added aqueous LiOH (1.4 mL, 2M, 2.76 mmol). The mixture was stirred at 50° C. for 16 hours. LCMS showed the material was consumed, then the reaction mixture was purified by prep-HPLC (ACN/water with 0.1% TFA modifier) to give 2-(3-(3-amino-7-(1-methyl-1H-pyrazol-4-yl)-1H-indazol-5-yl)-2-(hydroxymethyl)phenyl)-6-(tert-butyl)-8-fluorophthalazin-1(2H)-one. $^1$H NMR (400 MHz, $CD_3OD$) δ 8.47 (d, J=2.3 Hz, 1H), 8.14 (s, 1H), 7.98 (s, 1H), 7.89 (s, 1H), 7.84 (d, J=7.0 Hz, 2H), 7.69 (d, J=12.9 Hz, 1H), 7.60-7.52 (m, 2H), 7.45 (d, J=7.0 Hz, 1H), 4.43 (br. s., 2H), 3.97 (s, 3H), 1.43 (s, 9H) ppm.

Example 10

2-[3-(3-amino-7-pyridin-3-yl-1H-indazol-5-yl)-2-(hydroxymethyl)phenyl]-6-tert-butyl-8-fluorophthalazin-1(2H)-one

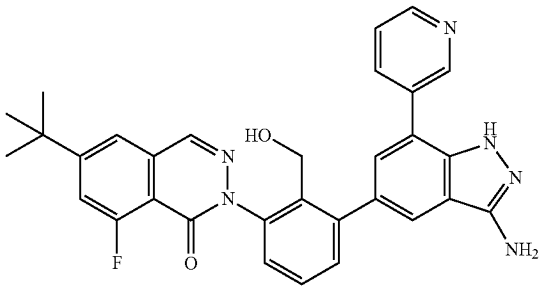 [SMILES: CC(C)(C)c1cc(F)c2c(=O)n(-c3cccc(-c4cc(-c5cccnc5)c5[nH]nc(N)c5c4)c3CO)ncc2c1]

Step 1: 5-bromo-7-(pyridin-3-yl)-1H-indazol-3-amine

To a solution of 5-bromo-7-iodo-1H-indazol-3-amine (200 mg, 0.592 mmol) and pyridin-3-ylboronic acid (87 mg, 0.710 mmol) in a mixed solvent of dioxane (6 mL) and water (1.500 mL) were added $K_2CO_3$ (327 mg, 2.367 mmol) and $PdCl_2$ (dppf) (43.3 mg, 0.059 mmol) under $N_2$. The mixture was stirred at 40° C. for 16 hours. The LC-MS showed the start material was consumed, and the desired product was formed. The mixture was diluted with EtOAc (20 mL), washed with water (10 mL) and brine (10 mL). The organic layer was dried over $Na_2SO_4$, filtered and concentrated in vacuo to give the crude product, which was purified by flash column chromatography (12 g silica gel, MeOH in DCM=0%-10%) to give 5-bromo-7-(pyridin-3-yl)-1H-indazol-3-amine. $^1$H NMR (400 MHz, DMSO-$d_6$) δ 11.86 (br. s., 1H), 8.85 (br. s., 1H), 8.61 (d, J=3.9 Hz, 1H), 8.05 (br. s., 1H), 7.99 (s, 1H), 7.53-7.48 (m, 1H), 7.44 (s, 1H), 5.55 (br. s., 2H) ppm.

Step 2: 2-(3-amino-7-(pyridin-3-yl)-1H-indazol-5-yl)-6-(6-(tert-butyl)-8-fluoro-1-oxophthalazin-2(1H)-yl)benzyl acetate To a solution of 5-bromo-7-(pyridin-3-yl)-1H-indazol-3-amine (180 mg, 0.623 mmol) in a mixed solvent of dioxane (2.5 mL) and water (0.250 mL) were added 2-(6-(tert-butyl)-8-fluoro-1-oxophthalazin-2(1H)-yl)-6-(4,4,5,5-tetramethyl-1,3,2-dioxaborolan-2-yl)benzyl acetate (462 mg, 0.934 mmol), X-Phos (59.4 mg, 0.125 mmol), $Pd_2(dba)_3$ (114 mg, 0.125 mmol) and $K_3PO_4$ (396 mg, 1.868 mmol) under $N_2$. Then the reaction mixture was stirred at 125° C. for 30 min under microwave. The reaction mixture was poured into water (50 mL) and extracted with EtOAc (20 mL×2). The combined organic layers were dried over $Na_2SO_4$, filtered and concentrated in vacuo to give the crude product, which was purified by flash column chromatography (12 g silica gel, MeOH in DCM: 0%-10%) to give 2-(3-amino-7-(pyridin-3-yl)-1H-indazol-5-yl)-6-(6-(tert-butyl)-8-fluoro-1-oxophthalazin-2(1H)-yl)benzyl acetate. $^1$H NMR (400 MHz, $CDCl_3$) δ 10.40 (s, 1H), 9.07 (s, 1H), 8.66 (d, J=3.9 Hz, 1H), 8.21 (s, 1H), 8.00 (d, J=7.4 Hz, 1H), 7.65 (s, 1H), 7.56-7.42 (m, 6H), 5.05 (s, 2H), 4.33 (s, 2H), 1.80 (s, 3H), 1.41 (s, 9H) ppm.

Step 3:2-(3-(3-amino-7-(pyridin-3-yl)-1H-indazol-5-yl)-2-(hydroxymethyl)phenyl)-6-(tert-butyl)-8-fluorophthalazin-1(2H)-one To a solution of 2-(3-amino-7-(pyridin-3-yl)-1H-indazol-5-yl)-6-(6-(tert-butyl)-8-fluoro-1-oxophthalazin-2(1H)-yl) benzyl acetate (160 mg, 0.277 mmol) in THF (10 mL) was added LiOH aqueous (1.4 mL, 2M, 2.77 mmol). The mixture was stirred at 50° C. for 16 hours. LCMS showed the material was consumed, then the reaction mixture was purified by Prep-HPLC (ACN/water with 0.1% TFA modifier) to give 2-(3-(3-amino-7-(pyridin-3-yl)-1H-indazol-5-yl)-2-(hydroxymethyl)phenyl)-6-(tert-butyl)-8-fluorophthalazin-1(2H)-one. $^1$H NMR (400 MHz, $CD_3OD$) δ9.10 (br. s., 1H), 8.76 (d, J=4.7 Hz, 1H), 8.63 (d, J=7.4 Hz, 1H), 8.48 (d, J=2.0 Hz, 1H), 8.03 (s, 1H), 7.94 (d, J=5.5 Hz, 1H), 7.88 (s, 1H), 7.83 (s, 1H), 7.69 (d, J=12.9 Hz, 1H), 7.60-7.55 (m, 2H), 7.46 (dd, J=2.3, 6.3 Hz, 1H), 4.43 (br. s., 2H), 1.43 (s, 9H) ppm.

Example 11

3-amino-5-[3-(6-tert-butyl-8-fluoro-1-oxophthalazin-2(1H)-yl)-2-(hydroxymethyl)phenyl]-N-methyl-1H-indazole-7-carboxamide

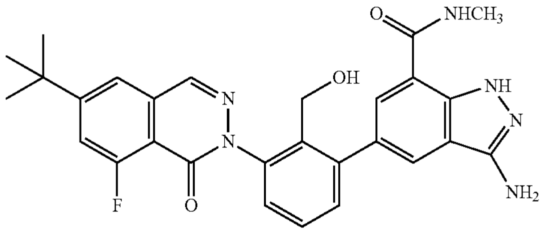 [SMILES: CNC(=O)c1cc(-c2cccc(-n3ncc4cc(C(C)(C)C)cc(F)c4c3=O)c2CO)cc2c(N)n[nH]c12]

To a solution of 3-amino-5-(3-(6-(tert-butyl)-8-fluoro-1-oxophthalazin-2(1H)-yl)-2-(hydroxymethyl)phenyl)-1H-indazole-7-carboxylic acid (20 mg, 0.040 mmol) in DMF (5 mL) was added methanamine (1.362 mg, 0.044 mmol), DIPEA (8.36 μL, 0.048 mmol) and HATU (18.20 mg, 0.048 mmol) and the resulting mixture was stirred for 2 h at 16° C., then purified by prep-HPLC to give 3-amino-5-(3-(6-(tert-butyl)-8-fluoro-1-oxophthalazin-2(1H)-yl)-2-(hydroxymethyl)phenyl)-N-methyl-1H-indazole-7-carboxamide. MS-ESI(m/z): 515 $(M+H)^+$(Method A, Rt: 2.715 min). $^1$H NMR (400 MHz, $CD_3OD$) δ 8.51 (d, J=2.51 Hz, 1H), 8.13 (s, 1H), 8.08 (d, J=1.00 Hz, 1H), 7.87 (s, 1H), 7.75 (d, J=1.51 Hz, 1H), 7.54-7.65 (m, 2H), 7.50 (d, J=7.53 Hz, 1H), 4.44 (br. s., 2H), 2.99 (s, 3H), 1.47 (s, 9H) ppm.

Example 12

2-{3-[3-amino-1-(pyridin-4-ylmethyl)-1H-indazol-5-yl]-2-(hydroxymethyl)phenyl}-6-tert-butyl-8-fluorophthalazin-1(2H)-one

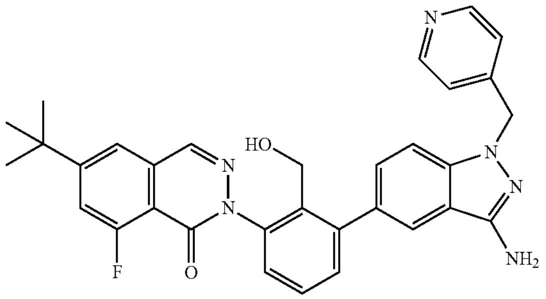 [SMILES: CC(C)(C)c1cc(F)c2c(=O)n(-c3cccc(-c4ccc5c(c4)c(N)nn5Cc4ccncc4)c3CO)ncc2c1]

Step 1: 5-bromo-1-(pyridin-4-ylmethyl)-1H-indazol-3-amine

To a solution of 5-bromo-1H-indazol-3-amine (100 mg, 0.472 mmol) in DMF (5 mL) was added NaH (22.63 mg, 0.566 mmol) at 0° C., the mixture was stirred for 5 min, 4-(bromomethyl)pyridine.HBr (143 mg, 0.566 mmol) was added, then the reaction mixture was stirred for 16 hours at 13° C. The resulting mixture was quenched with water (20 mL), extracted with EtOAc (20 mL×3), dried over $Na_2SO_4$, and concentrated and purified by flash column chromatography (Per.ether: EtOAc=2:3) to give 5-bromo-1-(pyridin-4-ylmethyl)-1H-indazol-3-amine. MS-ESI(m/z): 304 $(M+H)^+$(Method B; Rt: 0.823 min).

Step 2: 2-(3-amino-1-(pyridin-4-ylmethyl)-1H-indazol-5-yl)-6-(6-(tert-butyl)-8-fluoro-1-oxophthalazin-2(1H)-yl)benzyl acetate To a solution of 2-(6-(tert-butyl)-8-fluoro-1-oxophthalazin-2(1H)-yl)-6-(4,4,5,5-tetramethyl-1,3,2-dioxaborolan-2-yl)benzyl acetate (245 mg, 0.495 mmol) in dioxane (2 mL) and water (0.2 mL) was added 5-bromo-1-(pyridin-4-ylmethyl)-1H-indazol-3-amine (100 mg, 0.330 mmol), 2-(dicyclohexylphosphino)-2',4',6'-triisopropylbiphenyl (31.5 mg, 0.066 mmol), $Pd_2(dba)_3$ (60.4 mg, 0.066 mmol) and potassium phosphate (210 mg, 0.990 mmol). Then the reaction mixture was stirred for 30 min at 125° C. in a microwave. The reaction mixture was poured into water and extracted with EtOAc (20 mL×2). The combined organic layers were dried and concentrated. The residue was purified by flash column chromatography (MeOH in DCM: 0-10%) to give 2-(3-amino-1-(pyridin-4-ylmethyl)-1H-indazol-5-yl)-6-(6-(tert-butyl)-8-fluoro-1-oxophthalazin-2(1H)-yl)benzyl acetate as a solid. MS-ESI(m/z): 591 (M+H)+ (Method B; Rt: 1.083 min).

Step 3: 2-(3-(3-amino-1-(pyridin-4-ylmethyl)-1H-indazol-5-yl)-2-(hydroxymethyl)phenyl)-6-(tert-butyl)-8-fluorophthalazin-1(2H)-one To a solution of 2-(3-amino-1-(pyridin-4-ylmethyl)-1H-indazol-5-yl)-6-(6-(tert-butyl)-8-fluoro-1-oxophthalazin-2 (1H)-yl)benzyl acetate (120 mg, 0.203 mmol) in THF (5 mL) was added lithium hydroxide aqueous (5 mL, 2M, 10 mmol). Then the reaction mixture was stirred for 18 hours at 15° C. The mixture was poured into water (50 mL) and extracted with EtOAc (20 mL×2). The combined organic layers were dried over $Na_2SO_4$, filtered, concentrated and purified by Prep-HPLC to give 2-(3-(3-amino-1-(pyridin-4-ylmethyl)-1H-indazol-5-yl)-2-(hydroxymethyl)phenyl)-6-(tert-butyl)-8-fluorophthalazin-1(2H)-one as a solid. MS-ESI(m/z): 549 (M+H)+(Method A, Rt: 2.314 min). $^1$H NMR (400 MHz, $CD_3OD$) δ=8.76 (d, J=6.53 Hz, 2H), 8.50 (d, J=2.26 Hz, 1H), 7.84-7.90 (m, 2H), 7.68-7.79 (m, 3H), 7.58 (t, J=7.78 Hz, 2H), 7.42-7.52 (m, 3H), 5.77 (s, 2H), 4.45 (br. s., 2H), 1.47 (s, 9H) ppm.

Example 13

N-{3-[3-amino-7-(1-methyl-1H-pyrazol-4-yl)-1H-indazol-5-yl]-2-methylphenyl}-4-tert-butylbenzamide

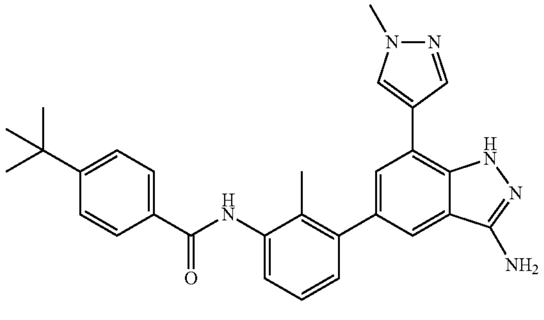 [SMILES: Cc1c(NC(=O)c2ccc(C(C)(C)C)cc2)cccc1-c1cc(-c2cnn(C)c2)c2[nH]nc(N)c2c1]

Step 1: 4-(tert-butyl)-N-(2-methyl-3-(4,4,5,5-tetramethyl-1,3,2-dioxaborolan-2-yl)phenyl)benzamide To a solution of 4-(tert-butyl)benzoic acid (200 mg, 1.122 mmol) in DCM (3 mL) was added DMF (1 μL, 0.013 Mmol) and oxalyl dichloride (712 mg, 5.61 mmol), and then the mixture was stirred at 20° C. for 3 hours. The reaction mixture was concentrated to give crude 4-(tert-butyl)benzoyl chloride. Above acyl chloride in DCM (5 mL) was added to a solution of 2-methyl-3-(4,4,5,5-tetramethyl-1,3,2-dioxaborolan-2-yl)aniline (262 mg, 1.124 mmol) and pyridine (267 mg, 3.37 mmol) in DCM (5 mL) dropwise and then the mixture was stirred at 20° C. for 18 h. The reaction mixture was diluted with DCM (20 mL), and then washed with water (15 mL). The organic layer was separated and dried over anhydrous sodium sulfate, filtered and purified via silica gel column chromatography (PE/EtOAc 90:10) to give 4-(tert-butyl)-N-(2-methyl-3-(4,4,5,5-tetramethyl-1,3,2-dioxaborolan-2-yl)phenyl)benzamide. MS-ESI (m/z): 394.3 $(M+1)^+$(Method B; Rt: 1.532 min). $^1$H NMR (400 MHz, $CDCl_3$) δ 8.08-8.02 (m, 1H), 7.85 (d, J=8.2 Hz, 2H), 7.65 (d, J=7.4 Hz, 1H), 7.53 (d, J=8.6 Hz, 2H), 7.27 (m, 1H), 2.55 (s, 3H), 1.37 (d, J=3.1 Hz, 21H) ppm.

Step 2: 5-bromo-7-(1-methyl-1H-pyrazol-4-yl)-1H-indazol-3-amine

To a solution of 5-bromo-7-iodo-1H-indazol-3-amine (800 mg, 2.367 mmol) and 1-methyl-4-(4,4,5,5-tetramethyl-1,3,2-dioxaborolan-2-yl)-1H-pyrazole (591 mg, 2.84 mmol) in a mixed solvent of dioxane (10 mL) and water (2.5 mL) was added $K_2CO_3$ (1309 mg, 9.47 mmol) and $PdCl_2$(dppf) (173 mg, 0.237 mmol) under $N_2$. The mixture was stirred at 40° C. for 16 hours. The LC-MS showed the start material was consumed, and the desired product was formed. The mixture was diluted with EtOAc (20 mL), and then the mixture was washed with water (10 mL) and brine (10 mL). The organic layer was dried over $Na_2SO_4$, concentrated in vacuo to give the crude product, which was purified by flash column chromatography (MeOH in DCM=0%~5%) to give 5-bromo-7-(1-methyl-1H-pyrazol-4-yl)-1H-indazol-3-amine. MS-ESI (m/z): 292.1/294.1 $(M+1)^+$(Method B; Rt: 0.965 min). $^1$H NMR (400 MHz, $CDCl_3$) δ 7.85 (s, 1H), 7.73 (s, 1H), 7.61 (br. s., 1H), 7.46 (s, 1H), 4.03 (s, 3H) ppm.

Step 3: N-(3-(3-amino-7-(1-methyl-1H-pyrazol-4-yl)-1H-indazol-5-yl)-2-methylphenyl)-4-(tert-butyl)benzamide To a suspension of 5-bromo-7-(1-methyl-1H-pyrazol-4-yl)-1H-indazol-3-amine (60 mg, 0.205 mmol), 4-(tert-butyl)-N-(2-methyl-3-(4,4,5,5-tetramethyl-1,3,2-dioxaborolan-2-yl)phenyl)benzamide (89 mg, 0.226 mmol) and $K_3PO_4$ (131 mg, 0.616 mmol) in 1,4-dioxane (4 mL) and water (1 mL) were added X-Phos (19.58 mg, 0.041 mmol) and $Pd_2(dba)_3$ (18.81 mg, 0.021 mmol) under $N_2$. Then the suspension was stirred at 125° C. for 1 h in a microwave reactor. Then the reaction mixture was concentrated to give crude product which was purified via Prep-HPLC (0.1% TFA) to give N-(3-(3-amino-7-(1-methyl-1H-pyrazol-4-yl)-1H-indazol-5-yl)-2-methylphenyl)-4-(tert-butyl)benzamide. MS-ESI (m/z): 479.3 (M+1)+, Method A, Rt: 2.564 min. $^1$H NMR (400 MHz, $CD_3OD$) δ=8.16 (s, 1H), 7.99 (s, 1H), 7.95 (d, J=8.2 Hz, 2H), 7.79 (d, J=9.8 Hz, 2H), 7.58 (d, J=8.6 Hz, 2H), 7.40-7.26 (m, 3H), 4.00 (s, 3H), 2.21 (s, 3H), 1.38 (s, 9H) ppm.

Example 14

2-{3-[3-amino-7-(morpholin-4-ylcarbonyl)-1H-indazol-5-yl]-2-(hydroxymethyl)phenyl}-6-tert-butyl-8-fluorophthalazin-1(2H)-one

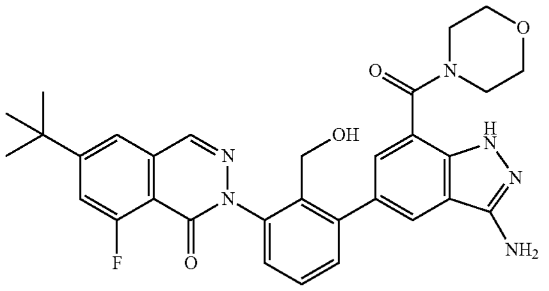 [SMILES: CC(C)(C)c1cc(F)c2c(=O)n(-c3cccc(-c4cc(C(=O)N5CCOCC5)c5[nH]nc(N)c5c4)c3CO)ncc2c1]

To a solution of 3-amino-5-(3-(6-(tert-butyl)-8-fluoro-1-oxophthalazin-2(1H)-yl)-2-(hydroxymethyl)phenyl)-1H-indazole-7-carboxylic acid (20 mg, 0.040 mmol) in DMF (5 mL) was added morpholine (3.82 mg, 0.044 mmol), DIPEA (8.36 μL, 0.048 mmol) and HATU (18.20 mg, 0.048 mmol) and the resulting mixture was stirred for 2 h at 16° C. The reaction mixture was purified by Prep-HPLC to give 2-(3-(3-amino-7-(morpholine-4-carbonyl)-1H-indazol-5-yl)-2-(hydroxymethyl)phenyl)-6-(tert-butyl)-8-fluorophthalazin-1(2H)-one. MS-ESI(m/z):571 $(M+H)^+$(Method A, Rt: 2.729 min). $^1$H NMR (400 MHz, $CD_3OD$) δ 8.46 (d, J=1.96 Hz, 1H), 7.90 (s, 1H), 7.82 (s, 1H), 7.68 (d, J=13.30 Hz, 1H), 7.48-7.59 (m, 3H), 7.42 (d, J=7.43 Hz, 1H), 4.41 (br. s., 2H), 3.69 (br. s., 8H), 1.43 (s, 9H) ppm.

Example 15

N-{3-[3-amino-7-(1-methyl-1H-pyrazol-4-yl)-1H-indazol-5-yl]-2-methylphenyl}-4-tert-butyl-2-fluorobenzamide

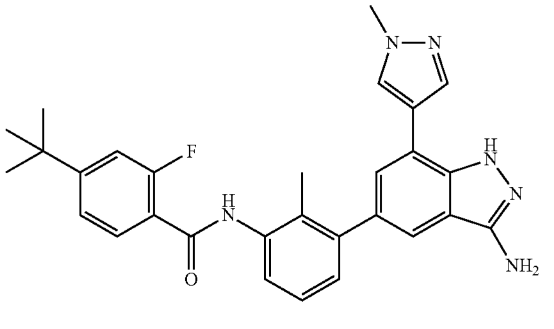 [SMILES: Cc1c(NC(=O)c2ccc(C(C)(C)C)cc2F)cccc1-c1cc(-c2cnn(C)c2)c2[nH]nc(N)c2c1]

Starting from 4-(tert-butyl)-2-fluorobenzoic acid, N-{3-[3-amino-7-(1-methyl-1H-pyrazol-4-yl)-1H-indazol-5-yl]-2-methylphenyl}-4-tert-butyl-2-fluorobenzamide was obtained followed a similar procedure as described in Example 13. MS-ESI (m/z): 460.2 $(M+1)^+$, Method A, Rt: 2.536 min. $^1H$ NMR (400 MHz, $CD_3OD$) δ 8.06 (d, J=1.3 Hz, 1H), 8.02 (d, J=1.3 Hz, 1H), 7.80 (t, J=8.0 Hz, 1H), 7.51 (d, J=7.5 Hz, 1H), 7.39 (dd, J=1.6, 8.2 Hz, 1H), 7.36-7.24 (m, 3H), 2.22 (s, 3H), 1.35 (s, 9H) ppm.

Example 16

3-amino-5-[3-(6-tert-butyl-8-fluoro-1-oxo-3,4-dihydroisoquinolin-2(1H)-yl)-2-(hydroxymethyl)phenyl]-1H-indazole-7-carboxamide

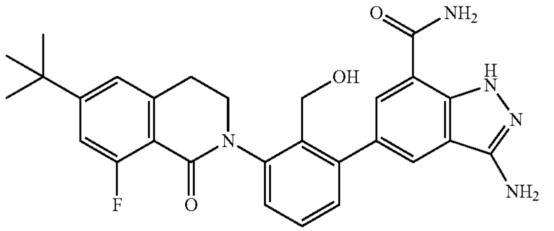 [SMILES: CC(C)(C)c1cc(F)c2c(c1)CCN(c1cccc(-c3cc(C(N)=O)c4[nH]nc(N)c4c3)c1CO)C2=O]

Step 1: 2-bromo-4-(tert-butyl)-6-fluorobenzoic acid

To a solution of 1-bromo-3-(tert-butyl)-5-fluorobenzene (3 g, 12.98 mmol) in THF (150 mL) was added LDA (7.14 mL, 14.28 mmol) at −78° C. dropwise and the resulting mixture was stirred at −78° C. for 120 minutes. The solution was poured onto dry ice (50 g) and stirred for 1 hour. The mixture was concentrated in vacuo and residue dissolved in EtOAc (100 mL) and 1 N HCl (50 mL). The organic layer was dried over $Na_2SO_4$ and concentrated in vacuo to give 2-bromo-4-(tert-butyl)-6-fluorobenzoic acid. $^1H$ NMR (400 MHz, $CDCl_3$) δ 11.45 (br. s., 1H), 7.45 (s, 1H), 7.14 (dd, J=1.2, 11.3 Hz, 1H), 1.37-1.30 (m, 9H) ppm.

Step 2: methyl 2-bromo-4-(tert-butyl)-6-fluorobenzoate

To a solution of 2-bromo-4-(tert-butyl)-6-fluorobenzoic acid (3.2 g, 11.63 mmol) and DMF (0.1 mL, 1.291 mmol) in DCM (40 mL) was added $(COCl)_2$ (3.45 mL, 39.4 mmol) and stirred at 13° C. for 16 hours. The solution was concentrated in vacuo to give the compound 2-bromo-4-(tert-butyl)-6-fluorobenzoyl chloride as an oil. MeOH (30 mL) was added and the mixture was stirred at 13° C. for 1 hours. The solution was concentrated in vacuo and purified by chromatography on silica gel (24 g) (PE) to give methyl 2-bromo-4-(tert-butyl)-6-fluorobenzoate. $^1H$ NMR (400 MHz, $CDCl_3$) δ 7.39 (s, 1H), 7.09 (d, J=11.0 Hz, 1H), 3.97 (s, 3H), 1.30 (s, 9H) ppm.

Step 3: methyl 4-(tert-butyl)-2-fluoro-6-methylbenzoate

A mixture of 2,4,6-trimethyl-1,3,5,2,4,6-trioxatriborinane (1.806 g, 14.39 mmol), methyl 2-bromo-4-(tert-butyl)-6-fluorobenzoate (3.2 g, 11.07 mmol), $PdCl_2$(dppf) (700 mg, 0.957 mmol) and $Cs_2CO_3$ (10.82 g, 33.2 mmol) in 1,4-dioxane (40 mL) was stirred at 120° C. for 3 hours under $N_2$ protection. The mixture was concentrated in vacuo, and the residue diluted with water (30 mL) and extracted with EtOAc (100 mL×3). The combined organic layers were dried over $Na_2SO_4$ and concentrated in vacuo. The black mixture was suspended in petroleum ether, filtered through silica gel (50 g) and washed with PE (300 mL). The filtrate was concentrated in vacuo to give methyl 4-(tert-butyl)-2-fluoro-6-methylbenzoate. $^1H$ NMR (400 MHz, $CDCl_3$) δ 7.01 (s, 1H), 6.96 (d, J=12.1 Hz, 1H), 3.93 (s, 3H), 2.41 (s, 3H), 1.30 (s, 9H). MS-ESI (m/z): 225 $(M+1)^+$(Method B; Rt: 1.232 min).

Step 4: 4-(tert-butyl)-2-fluoro-6-methylbenzoic acid

A solution of KOH (1 g, 17.82 mmol) and methyl 4-(tert-butyl)-2-fluoro-6-methylbenzoate (2.2 g, 9.81 mmol) in water (15.00 mL) and MeOH (15 mL) was stirred at 80° C. for 16 hours. The solution was concentrated in vacuo and the residue partitioned between 1 N HCl (20 mL) and EtOAc (50 mL). The organic layer was dried over $Na_2SO_4$ and concentrated in vacuo to give 4-(tert-butyl)-2-fluoro-6-methylbenzoic acid as a solid. $^1H$ NMR (400 MHz, $CDCl_3$) δ 7.04 (s, 1H), 6.99 (d, J=12.1 Hz, 1H), 2.58-2.47 (m, 3H), 1.31 (s, 9H) ppm.

Step 5: 4-(tert-butyl)-2-fluoro-6-methylbenzamide

To a mixture of 2-bromo-4-(tert-butyl)-6-fluorobenzoic acid (1 g, 3.63 mmol), ammonium chloride (500 mg, 9.35 mmol) and TEA (2.53 mL, 18.17 mmol) in THF (30 mL) was added HATU (1.658 g, 4.36 mmol) and the mixture was stirred at 15° C. for 16 hours. The mixture was concentrated in vacuo and the residue partioned between water (100 mL) and EtOAc (200 mL). The organic layer was washed with 1 N HCl (50 mL) and brine (50 mL), dried over $Na_2SO_4$ and purified by chromatography on silica gel (PE: EtOAc=30:70) to give the compound 2-bromo-4-(tert-butyl)-6-fluorobenzamide as a solid. $^1H$ NMR (400 MHz, $CDCl_3$) δ 7.04 (s, 1H), 6.95 (d, J=12.0 Hz, 1H), 6.08-5.80 (m, 2H), 2.47 (s, 3H), 1.30 (s, 9H) ppm.

Step 6:(E)-4-(tert-butyl)-N-((dimethylamino)methylene)-2-fluoro-6-methylbenzamide A solution of 4-(tert-butyl)-2-fluoro-6-methylbenzamide (900 mg, 4.30 mmol) in 1,1-dimethoxy-N,N-dimethylmethanamine (5 mL, 37.5 mmol) was stirred at 95° C. for 2 hours. The solution was concentrated in vacuo to give the compound (E)-4-(tert-butyl)-N-((dimethylamino)methylene)-2-fluoro-6-methylbenzamide as an oil without further purification.

Step 7: 6-(tert-butyl)-8-fluoroisoquinolin-1(2H)-one

To a solution of (E)-4-(tert-butyl)-N-((dimethylamino)methylene)-2-fluoro-6-methylbenzamide (1.1 g, 4.16 mmol) in THF (25 mL) was added potassium tert-butoxide, THF (10 mL, 10.00 mmol) and the mixture was stirred at 70° C. for 2 hours. The solution was poured into water (20 mL) and extracted with EtOAc (50 mL×2). The combined organic layers were dried over $Na_2SO_4$ and purified by chromatography on silica gel (12 g) (PE: THF=70:30 to 50:50) to give 6-(tert-butyl)-8-fluoroisoquinolin-1(2H)-one. $^1$H NMR (400 MHz, $CDCl_3$) δ 11.08 (br. s., 1H), 7.29 (s, 1H), 7.22-7.14 (m, 2H), 6.53-6.47 (m, 1H), 1.37 (s, 9H). MS-ESI (m/z): 220 $(M+1)^+$(Method B; Rt: 1.088 min).

Step 8: 6-(tert-butyl)-8-fluoro-3,4-dihydroisoquinolin-1(2H)-one

To a solution of 6-(tert-butyl)-8-fluoroisoquinolin-1(2H)-one (550 mg, 2.508 mmol) in MeOH (100 mL) was added Pd/C (2670 mg, 2.508 mmol) and the mixture was stirred for 2 days under $H_2$. The mixture was filtered and the filtrate was concentrated in vacuo to give the compound 6-(tert-butyl)-8-fluoro-3,4-dihydroisoquinolin-1(2H)-one as a solid without purification. $^1$H NMR (400 MHz, $CDCl_3$) δ 7.38 (d, J=7.8 Hz, 1H), 7.22 (s, 1H), 7.05 (d, J=13.3 Hz, 1H), 7.01 (s, 1H), 6.74 (br. s., 1H), 3.58-3.47 (m, 2H), 3.01-2.93 (m, 2H), 1.34 (br. s., 1H), 1.33-1.26 (m, 9H) ppm. MS-ESI (m/z): 222 $(M+1)^+$(Method B; Rt: 1.132 min).

Step 9: 2-bromo-6-(6-(tert-butyl)-8-fluoro-1-oxo-3,4-dihydroisoquinolin-2(1H)-yl)benzyl acetate To a solution of N1,N2-dimethylcyclohexane-1,2-diamine(trans) (193 mg, 1.356 mmol), 2,6-dibromobenzyl acetate (3 g, 9.74 mmol), 6-(tert-butyl)-8-fluoro-3,4-dihydroisoquinolin-1(2H)-one (300 mg, 1.356 mmol) and $Cs_2CO_3$ (1325 mg, 4.07 mmol) in DMF (20 mL) was added copper(I) iodide (646 mg, 3.39 mmol). The mixture was stirred at 150° C. for 3 hours. The solution was concentrated in vacuo. The residue was partitioned between water (100 mL) and EtOAc (200 mL). The organic layer was washed with 10 mL 1 N HCl and brine (20 mL), dried over $Na_2SO_4$, concentrated in vacuo and purified by chromatography on silica gel (PE: THF=25:75 to 35:65) to give a mixture of 2-bromo-6-(6-(tert-butyl)-8-fluoro-1-oxo-3,4-dihydroisoquinolin-2(1H)-yl)benzyl acetate and 2-(6-(tert-butyl)-8-fluoro-1-oxo-3,4-dihydroisoquinolin-2(1H)-yl)-6-iodobenzyl acetate as a solid. $^1$H NMR (400 MHz, $CDCl_3$) δ 7.90 (d, J=8.2 Hz, 1H), 7.62 (d, J=7.8 Hz, 1H), 7.33-7.28 (m, 1H), 7.26-7.22 (m, 1H), 7.15-7.03 (m, 2H), 5.30-5.13 (m, 2H), 3.96 (dt, J=3.7, 11.2 Hz, 1H), 3.82-3.70 (m, 1H), 3.31 (ddd, J=4.9, 10.5, 15.6 Hz, 1H), 3.09-2.98 (m, 1H), 2.08-2.05 (m, 3H), 1.37-1.31 (m, 9H) ppm.

Step 10: 2-(6-(tert-butyl)-8-fluoro-1-oxo-3,4-dihydroisoquinolin-2(1H)-yl)-6-(4,4,5,5-tetramethyl-1,3,2-dioxaborolan-2-yl)benzyl acetate A solution of 2-(6-(tert-butyl)-8-fluoro-1-oxo-3,4-dihydroisoquinolin-2(1H)-yl)-6-iodobenzyl acetate (400 mg, 0.266 mmol), 2-bromo-6-(6-(tert-butyl)-8-fluoro-1-oxo-3,4-dihydroisoquinolin-2(1H)-yl)benzyl acetate (400 mg, 0.589 mmol), $(BPin)_2$ (120 mg, 0.473 mmol), $PdCl_2$(dppf) (20 mg, 0.027 mmol) and KOAc (200 mg, 2.038 mmol) in 1,4-dioxane (15 mL) was stirred at 130° C. for 16 hours under $N_2$ protection. The solution was poured into water (80 mL). The mixture was extracted with DCM (100 mL×3) and the combined organic layers were dried over $Na_2SO_4$ and concentrated. The residue purified by chromatography on silica gel (4 g) (PE: THF=80:20) to give 2-(6-(tert-butyl)-8-fluoro-1-oxo-3,4-dihydroisoquinolin-2(1H)-yl)-6-(4,4,5,5-tetramethyl-1,3,2-dioxaborolan-2-yl)benzyl acetate as an oil. $^1$H NMR (400 MHz, $CDCl_3$) δ 7.81 (d, J=7.0 Hz, 1H), 7.44-7.30 (m, 2H), 7.08-6.99 (m, 2H), 5.51 (d, J=11.7 Hz, 1H), 5.21 (d, J=11.3 Hz, 1H), 4.03-3.87 (m, 1H), 3.75 (br. s., 1H), 3.77-3.71 (m, 1H), 3.36-3.20 (m, 1H), 3.01 (d, J=16.0 Hz, 1H), 2.00 (s, 3H), 1.27 (s, 9H), 1.24 (s, 12H). MS-ESI (m/z): 496 $(M+1)^+$(Method B; Rt: 1.496 min).

Step 11: 2-(3-amino-7-cyano-1H-indazol-5-yl)-6-(6-(tert-butyl)-8-fluoro-1-oxo-3,4-dihydroisoquinolin-2(1H)-yl)benzyl acetate A solution of 2-(6-(tert-butyl)-8-fluoro-1-oxo-3,4-dihydroisoquinolin-2(1H)-yl)-6-(4,4,5,5-tetramethyl-1,3,2-dioxaborolan-2-yl)benzyl acetate (120 mg, 0.242 mmol), 3-amino-5-bromo-1H-indole-7-carbonitrile (40 mg, 0.169 mmol), X-Phos (20 mg, 0.042 mmol), $Pd_2(dba)_3$ (20 mg, 0.022 mmol) and $K_3PO_4$ (200 mg, 0.942 mmol) in water (1 mL) and 1,4-dioxane (3 mL) was stirred at 125° C. under microwave irradiation for 1 hour under $N_2$ protection. The solution was poured into water (10 mL), extracted with DCM (20 mL×3) and the combined organic layers were dried over $Na_2SO_4$ and concentrated in vacuo to give 2-(3-amino-7-cyano-1H-indol-5-yl)-6-(6-(tert-butyl)-8-fluoro-1-oxo-3,4-dihydroisoquinolin-2(1H)-yl)benzyl acetate. MS-ESI (m/z): 526 $(M+1)^+$(Method B; Rt: 1.239 min).

Step 12:3-amino-5-(3-(6-(tert-butyl)-8-fluoro-1-oxo-3,4-dihydroisoquinolin-2(1H)-yl)-2-(hydroxymethyl)phenyl)-1H-indazole-7-carboxamide To a mixture of 2-(3-amino-7-cyano-1H-indol-5-yl)-6-(6-(tert-butyl)-8-fluoro-1-oxo-3,4-dihydroisoquinolin-2(1H)-yl)benzyl acetate (89 mg, 0.170 mmol) in water (5 mL) and THF (5 mL) was added hydrido(dimethylphosphinous acid-kp)[hydrogen bis (dimethylphosphinito-kp)]platinum(II) (1 mg, 2.341 μmol). The mixture was stirred at 80° C. for 4 hours under $N_2$ protection. To the mixture was then added lithium hydroxide. $H_2O$ (100 mg, 2.383 mmol) and stirred at 80° C. for 16 hours. The mixture was concentrated in vacuo and purified via Prep-HPLC to give 2-(3-amino-7-carbamoyl-1H-indol-5-yl)-6-(6-(tert-butyl)-8-fluoro-1-oxo-3,4-dihydroisoquinolin-2(1H)-yl)benzyl acetate. $^1$H NMR (400 MHz, $CD_3OD$) δ8.14 (d, J=9.4 Hz, 2H), 7.57-7.50 (m, 1H), 7.47-7.36 (m, 2H), 7.24 (s, 1H), 7.15 (d, J=12.9 Hz, 1H), 4.53-4.42 (m, 2H), 4.09-3.99 (m, 1H), 3.95-3.85 (m, 1H), 3.41-3.34 (m, 1H), 3.19-3.07 (m, 1H), 1.34 (s, 9H) ppm. MS-ESI (m/z): 502 $(M+1)^+$(Method A; Rt: 2.712 min).

Example 17

2-[3-{3-amino-7-[1(1-methylethyl)-1H-pyrazol-3-yl]-1H-indazol-5-yl}-2-(hydroxymethyl)phenyl]-6-tert-butyl-8-fluorophthalazin-1(2H)-one

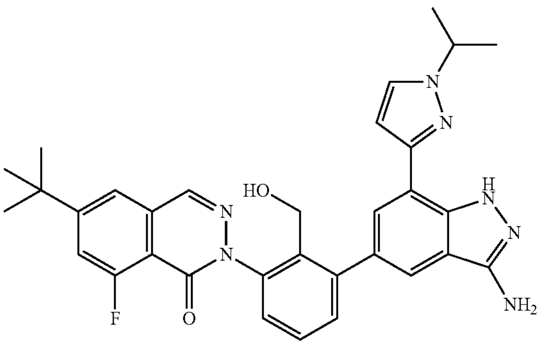 [SMILES: CC(C)n1ccc(-c2cc(-c3cccc(-n4ncc5cc(C(C)(C)C)cc(F)c5c4=O)c3CO)cc3c(N)n[nH]c23)n1]

Starting from 1-isopropyl-3-(4,4,5,5-tetramethyl-1,3,2-dioxaborolan-2-yl)-1H-pyrazole, 2-[3-{3-amino-7-[1-(1-methylethyl)-1H-pyrazol-3-yl]-1H-indazol-5-yl}-2-(hydroxymethyl)phenyl]-6-tert-butyl-8-fluorophthalazin-1(2H)-one was obtained following a similar procedure as described in Example 9. MS-ESI: found 566 $(M+1)^+$. (Method B; Rt:2.734 min). $^1H$ NMR (400 MHz, $CD_3OD$) δ 8.43 (s, 1H), 8.08 (s, 1H), 7.87 (s, 1H), 7.78 (s, 1H), 7.71-7.60 (m, 2H), 7.57-7.46 (m, 2H), 7.41 (d, J=7.0 Hz, 1H), 6.78 (br. s., 1H), 4.63 (td, J=6.7, 13.3 Hz, 1H), 4.39 (br. s., 2H), 1.53 (d, J=6.7 Hz, 6H), 1.38 (s, 9H) ppm.

Example 18

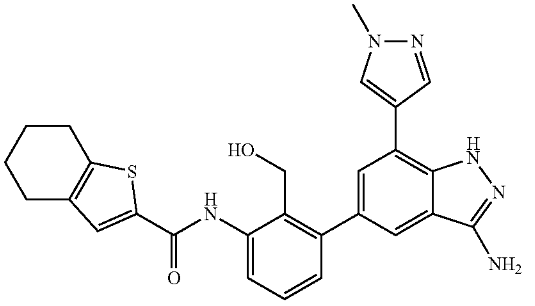 [SMILES: Cn1cc(-c2cc(-c3cccc(NC(=O)c4cc5c(s4)CCCC5)c3CO)cc3c(N)n[nH]c23)cn1]

N-{3-[3-amino-7-(1-methyl-1H-pyrazol-4-yl)-1H-indazol-5-yl]-2-(hydroxymethyl)phenyl}-4,5,6,7-tetrahydro-1-benzothiophene-2-carboxamide Step 1: (2-amino-6-bromophenyl)methanol To a mixture of 2-amino-6-bromobenzoic acid (1.4 g, 6.48 mmol) in THF (20 mL) was added $BH_3$.THF (6.48 mL, 6.48 mmol). The mixture was stirred at 18° C. for 24 hours. The reaction mixture was quenched by the addition of MeOH (2 mL) and 1N HCl (3 mL). The pH was adjusted to around 9 with satd. $NaHCO_3$ aqueous (20 mL) and the mixture extracted with EtOAc (100 mL×2). The mixture was concentrated to afford (2-amino-6-bromophenyl)methanol as a solid. $^1H$ NMR (400 MHz, $CDCl_3$) δ 6.95-6.82 (m, 2H), 6.56 (t, J=4.5 Hz, 1H), 4.84 (s, 2H), 4.39-4.11 (m, 1H) ppm.

Step 2: 3-bromo-2-(((tert-butyldimethylsilyl)oxy)methyl)aniline

To a solution of (2-amino-6-bromophenyl)methanol (1.1 g, 5.44 mmol) in THF (20 mL) were added 1H-imidazole (1.112 g, 16.33 mmol) and TBS-Cl (0.985 g, 6.53 mmol). The mixture was stirred at 17° C. for 12 hours. The reaction mixture was quenched with water (30 mL) and extracted with EtOAc (30 mL×3). The combined organic phases were dried over $Na_2SO_4$ and concentrated in vacuo to give 3-bromo-2-(((tert-butyldimethylsilyl)oxy)methyl)aniline as an oil. $^1H$ NMR (400 MHz, $CDCl_3$) δ 6.87-6.75 (m, 2H), 6.55-6.40 (m, 1H), 4.85 (s, 2H), 4.38 (br. s., 2H), 0.79 (s, 9H), 0.00 (s, 6H) ppm.

Step 3: N-(3-bromo-2-(((tert-butyldimethylsilyl)oxy)methyl)phenyl)-4,5,6,7-tetrahydrobenzo[b]thiophene-2-carboxamide Oxalyl dichloride (418 mg, 3.29 mmol) was added to a stirring suspension of 4,5,6,7-tetrahydrobenzo[b]thiophene-2-carboxylic acid (300 mg, 1.646 mmol) in $CH_2Cl_2$ (5 mL) at 18° C. After stirring for 3 h at 18° C. the reaction mixture was concentrated under reduced pressure. The residue was dissolved in $CH_2Cl_2$ (5 mL), and 3-bromo-2-(((tert-butyldimethylsilyl)oxy)methyl)aniline (573 mg, 1.811 mmol), TEA (0.459 mL, 3.29 mmol) were added. After stirring for 1.5 hours, the reaction mixture was concentrated under reduced pressure. The resulting residue was dissolved in $CH_2Cl_2$ (20 mL); the organic layer was washed with water (20 mL), dried over $Na_2SO_4$, and filtered. The filtrate was concentrated under reduced pressure to afford the title compound N-(3-bromo-2-(((tert-butyldimethylsilyl)oxy)methyl)phenyl)-4,5,6,7-tetrahydrobenzo[b]thiophene-2-carboxamide as a solid. $^1H$ NMR (400 MHz, $CDCl_3$) δ 9.66 (br. s., 1H), 8.18 (d, J=7.8 Hz, 1H), 7.22-7.19 (m, 1H), 7.18-7.14 (m, 1H), 7.11-7.00 (m, 1H), 4.99 (s, 2H), 2.71 (t, J=5.5 Hz, 2H), 2.52 (t, J=5.5 Hz, 2H), 1.74 (td, J=5.4, 11.4 Hz, 4H), 0.82 (s, 9H), 0.07 (s, 6H) ppm.

Step 4: N-(2-(((tert-butyldimethylsilyl)oxy)methyl)-3-(4,4,5,5-tetramethyl-1,3,2-dioxaborolan-2-yl)phenyl)-4,5,6,7-tetrahydrobenzo[b]thiophene-2-carboxamide To a solution of N-(3-bromo-2-(((tert-butyldimethylsilyl)oxy)methyl)phenyl)-4,5,6,7-tetrahydrobenzo[b]thiophene-2-carboxamide (300 mg, 0.624 mmol) and 4,4,4',4',5,5,5',5'-octamethyl-2,2'-bi(1,3,2-dioxaborolane) (190 mg, 0.749 mmol) in 1,4-dioxane (5 mL) were added $PdCl_2$(dppf) (22.84 mg, 0.031 mmol) and potassium acetate (153 mg, 1.561 mmol). Then the reaction mixture was stirred for 1 hour at 100° C. in a microwave reactor. The reaction mixture was cooled and concentrated in vacuo, and the residue was purified by chromatography on silica gel eluted with (PE:EtOAc=10:1) to afford N-(2-(((tert-butyldimethylsilyl)oxy)methyl)-3-(4,4,5,5-tetramethyl-1,3,2-dioxaborolan-2-yl)phenyl)-4,5,6,7-tetrahydrobenzo[b]thiophene-2-carboxamide as a solid. $^1H$ NMR (400 MHz, $CDCl_3$) δ 7.47 (d, J=7.0 Hz, 1H), 7.27-7.18 (m, 2H), 7.15 (s, 1H), 5.14 (s, 2H), 2.72-2.67 (m, 2H), 2.51 (br. s., 2H), 1.73 (td, J=5.2, 11.1 Hz, 4H), 1.24 (s, 12H), 0.80 (s, 9H), 0.03 (s, 6H) ppm.

Step 5: N-(3-(3-amino-7-(1-methyl-1H-pyrazol-4-yl)-1H-indazol-5-yl)-2-(((tert-butyldimethylsilyl)oxy)methyl)phenyl)-4,5,6,7-tetrahydrobenzo[b]thiophene-2-carboxamide To a solution of 5-bromo-7-(1-methyl-1H-pyrazol-4-yl)-1H-indazol-3-amine (38.2 mg, 0.131 mmol) in 1,4-dioxane (3 mL) and $H_2O$ (0.3 mL) was added N-(2-(((tert-butyldimethylsilyl)oxy)methyl)-3-(4,4,5,5-tetramethyl-1,3,2-dioxaborolan-2-yl)phenyl)-4,5,6,7-tetrahydrobenzo[b]thiophene-2-carboxamide (82.8 mg, 0.157 mmol), $K_3PO_4$(83.3 mg, 0.392 mmol), $Pd_2(dba)_3$ (24.0 mg, 0.0262 mmol) and X-Phos (12.4 mg, 0.0262 mmol) under an $N_2$ atmosphere. The mixture was stirred at 125° C. under $N_2$ for 1 hour in a microwave reactor. The mixture was diluted with water (5 mL) and extracted with ethyl acetate (5 mL×2). The combined organic layers were washed with brine (10 mL×2), dried over anhydrous sodium sulfate and concentrated to give N-(3-(3-amino-7-(1-methyl-1H-pyrazol-4-yl)-1H-indazol-5-yl)-2-(((tert-butyldimethylsilyl)oxy)methyl)phenyl)-4,5,6,7-tetrahydrobenzo[b]thiophene-2-carboxamide as a solid. MS-ESI(m/z): 613 $(M+H)^+$(Method B; Rt:1.445 min).

Step 6: N-(3-(3-amino-7-(1-methyl-1H-pyrazol-4-yl)-1H-indazol-5-yl)-2-(hydroxymethyl)phenyl)-4,5,6,7-tetrahydrobenzo[b]thiophene-2-carboxamide To a solution of N-(3-(3-amino-7-(1-methyl-1H-pyrazol-4-yl)-1H-indazol-5-yl)-2-(((tert-butyldimethylsilyl)oxy)methyl)phenyl)-4,5,6,7-tetrahydrobenzo[b]thiophene-2-carboxamide (80.0 mg, 0.131 mmol) in MeOH (2 mL) was added HCl (2 mol/L, 2 mL). The reaction mixture was stirred at 20° C. for 2 hours. The mixture was concentrated. The residue was purified by Prep-HPLC to give N-(3-(3-amino-7-(1-methyl-1H-pyrazol-4-yl)-1H-indazol-5-yl)-2-(hydroxymethyl)phenyl)-4,5,6,7-tetrahydrobenzo[b]thiophene-2-carboxamide as a solid. MS ESI (m/z): 613 $(M+H)^+$ 499. (Method A; Rt:2.775 min). $^1H$ NMR (400 MHz, $CD_3OD$) δ 8.12 (s, 1H), 7.99-7.90 (m, 2H), 7.73 (d, J=6.7 Hz, 2H), 7.44-7.32 (m, 2H), 7.21-7.09 (m, 1H), 4.64 (s, 2H), 3.96 (s, 3H), 2.83-2.74 (m, 2H), 2.67-2.56 (m, 2H), 1.89-1.78 (m, 4H) ppm.

Example 19

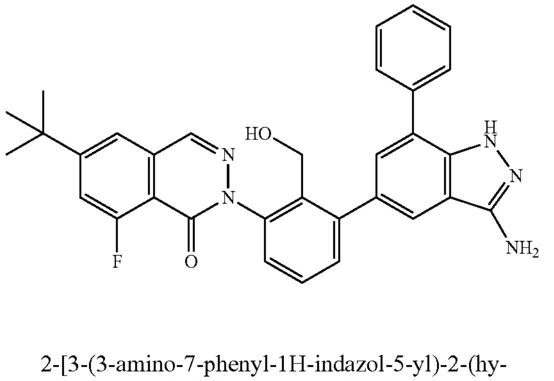

2-[3-(3-amino-7-phenyl-1H-indazol-5-yl)-2-(hydroxymethyl)phenyl]-6-tert-butyl-8-fluorophthalazin-1(2H)-one Starting from the phenylboronic acid, 2-[3-(3-amino-7-phenyl-1H-indazol-5-yl)-2-(hydroxymethyl)phenyl]-6-tert-butyl-8-fluorophthalazin-1(2H)-one was obtained following a similar procedure as described in Example 6. MS-ESI (m/z): 534 (M+H). (Method A, Rt: 2.343 min). $^1H$ NMR (400 MHz, $CD_3OD$) δ 8.47 (d, J=2.3 Hz, 1H), 7.95 (s, 1H), 7.82 (d, J=2.0 Hz, 2H), 7.76-7.65 (m, 3H), 7.61-7.49 (m, 4H), 7.48-7.40 (m, 2H), 4.45 (br. s., 2H), 1.43 (s, 9H) ppm.

Example 20

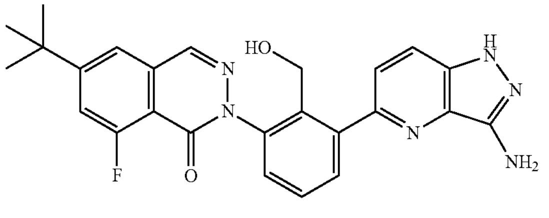 [SMILES: CC(C)(C)c1cc(F)c2c(=O)n(-c3cccc(-c4ccc5[nH]nc(N)c5n4)c3CO)ncc2c1]

2-[3-(3-amino-1H-pyrazolo[4,3-b]pyridin-5-yl)-2-(hydroxymethyl)phenyl]-6-tert-butyl-8-fluorophthalazin-1(2H)-one Step 1: 6-chloro-2-methylpyridin-3-amine To a suspension of 6-chloro-2-methyl-3-nitropyridine (4.5 g, 26.1 mmol) in AcOH (100 mL) was added Iron powder (7.28 g, 130 mmol). The resulting mixture was stirred at 35-45° C. for 2 h. The mixture was basified with aq.1N NaOH to pH=7-8 and then extracted with EtOAc (200 mL×3). The combined organic layers were dried over $Na_2SO_4$ and concentrated to give crude 6-chloro-2-methylpyridin-3-amine as a solid. $^1$HNMR (400 MHz, $CDCl_3$) δ6.97 (d, J=8.0 Hz, 1H), 6.89 (d, J=8.4 Hz, 1H), 3.61 (brs, 2H), 2.37 (s, 3H) ppm.

Step 2: N-(6-chloro-2-methylpyridin-3-yl)acetamide

To a solution of 6-chloro-2-methylpyridin-3-amine (3.68 g, 25.8 mmol) in acetic acid (100 mL) was added acetic anhydride (5.27 g, 51.6 mmol). The mixture was stirred at 10-15° C. for 1 hour. The solvent was removed to give crude N-(6-chloro-2-methylpyridin-3-yl)acetamide, which was used directly in the next step.

Step 3: 1-(5-chloro-1H-pyrazolo[4,3-b]pyridin-1-yl)ethanone

To a solution of N-(6-chloro-2-methylpyridin-3-yl)acetamide (4.76 g, 25.8 mmol) in $CHCl_3$ (200 mL) was added acetic anhydride (1.46 mL, 15.47 mmol) at 0° C. The resulting mixture was stirred for 1 h at 25-30° C. Then isopentyl nitrite (6.64 g, 56.7 mmol) and potassium acetate (0.506 g, 5.16 mmol) were added. The reaction mixture was stirred 70-80° C. for 18 h. The solvent was removed and to the residue was added EtOAc (100 mL), then washed with water (30 mL×2), brine (30 mL×2), dried over $Na_2SO_4$ and concentrated. The residue was purified by flash column chromatography (EtOAc in PE: 0%-10%) to give 1-(5-chloro-1H-pyrazolo[4,3-b]pyridin-1-yl)ethanone. $^1$HNMR (400 MHz, $CDCl_3$) δ 8.64 (d, J=8.4 Hz, 1H), 8.25 (s, 1H), 7.46 (d, J=8.8 Hz, 1H), 2.79 (s, 3H) ppm.

Step 4: 5-chloro-3-nitro-1H-pyrazolo[4,3-b]pyridine

To a solution of 1-(5-chloro-1H-pyrazolo[4,3-b]pyridin-1-yl)ethanone (800 mg, 4.09 mmol) in sulfuric acid (12 mL, 225 mmol) was slowly added nitric acid (3.0 mL, 47.0 mmol) at 0° C. Then the resulting mixture was stirred for 2 hours at 70-80° C. The reaction mixture was cooled to 0° C. and poured into water (200 mL). The resulting mixture was extracted with EtOAc (100 mL×3). The combined organic layers were dried over $Na_2SO_4$ and concentrated to give crude 5-chloro-3-nitro-1H-pyrazolo[4,3-b]pyridine as a solid. $^1H$ NMR (400 MHz, DMSO-$d_6$) δ=8.33 (d, J=9.2 Hz, 1H), 7.65 (d, J=8.8 Hz, 1H) ppm.

Step 5: 2-(6-(tert-butyl)-8-fluoro-1-oxophthalazin-2(1H)-yl)-6-(3-nitro-1H-pyrazolo[4,3-b]pyridin-5-yl) benzyl acetate To a solution of 2-(6-(tert-butyl)-8-fluoro-1-oxophthalazin-2(1H)-yl)-6-(4,4,5,5-tetramethyl-1,3,2-dioxaborolan-2-yl)benzyl acetate (2614 mg, 5.29 mmol) in dioxane (5 mL) and water (0.5 mL) was added 5-chloro-3-nitro-1H-pyrazolo[4,3-b]pyridine (700 mg, 3.53 mmol), $Pd_2(dba)_3$ (646 mg, 0.705 mmol), 2-(dicyclohexylphosphino)-2',4',6'-triisopropylbiphenyl (336 mg, 0.705 mmol) and potassium phosphate (2245 mg, 10.58 mmol). The reaction mixture was stirred for 30 min at 125° C. in a microwave reactor. The reaction mixture was poured into water (20 mL) and extracted with EtOAc (20 mL×2). The combined organic layers were dried and concentrated to give 2-(6-(tert-butyl)-8-fluoro-1-oxophthalazin-2(1H)-yl)-6-(3-nitro-1H-pyrazolo[4,3-b]pyridin-5-yl)benzyl acetate. MS-ESI(m/z): 531 $(M+H)^+$(Method B; Rt: 1.305 min).

Step 6: 6-(tert-butyl)-8-fluoro-2-(2-(hydroxymethyl)-3-(3-nitro-1H-pyrazolo[4,3-b]pyridin-5-yl) phenyl)phthalazin-1(2H)-one To a solution of 2-(6-(tert-butyl)-8-fluoro-1-oxophthalazin-2(1H)-yl)-6-(3-nitro-1H-pyrazolo[4,3-b]pyridin-5-yl)benzyl acetate (2 g, 3.77 mmol) in THF (10 mL) was added aqueous lithium hydroxide (10 mL, 2M, 20 mmol). Then the reaction mixture was stirred for 18 hours at 18° C. The mixture was poured into water (50 mL) and extracted with EtOAc (20 mL×2). The combined organic layers were dried over $Na_2SO_4$, filtered, concentrated and purified by Prep-HPLC to give 6-(tert-butyl)-8-fluoro-2-(2-(hydroxymethyl)-3-(3-nitro-1H-pyrazolo[4,3-b]pyridin-5-yl)phenyl)phthalazin-1(2H)-one. MS-ESI(m/z): 489 $(M+H)^+$(Method B; Rt: 1.239 min).

Step 7: 2-(3-(3-amino-1H-pyrazolo[4,3-b]pyridin-5-yl)-2-(hydroxymethyl)phenyl)-6-(tert-butyl)-8-fluorophthalazin-1(2H)-one A mixture of 6-(tert-butyl)-8-fluoro-2-(2-(hydroxymethyl)-3-(3-nitro-1H-pyrazolo[4,3-b]pyridin-5-yl)phenyl) phthalazin-1(2H)-one (150 mg, 0.307 mmol), sodium hydrogen carbonate (31.0 mg, 0.368 mmol) and palladium on charcoal (10%, 6.54 mg) in EtOH (10 mL) was charged with $H_2$ (15 psi) and the reaction mixture was stirred at 18° C. for 16 h. The reaction mixture was filtered and the filtrate was purified by Prep-HPLC to give 2-(3-(3-amino-1H-pyrazolo[4,3-b]pyridin-5-yl)-2-(hydroxymethyl)phenyl)-6-(tert-butyl)-8-fluorophthalazin-1(2H)-one. MS-ESI (m/z): 459 $(M+H)^+$(Method A, Rt: 2.379 min). $^1H$ NMR (400 MHz, $CD_3OD$) δ 8.47 (d, J=2.3 Hz, 1H), 8.00 (d, J=8.6 Hz, 1H), 7.86-7.77 (m, 2H), 7.73-7.58 (m, 3H), 7.51 (d, J=7.4 Hz, 1H), 4.42 (d, J=5.9 Hz, 2H), 1.43 (s, 9H) ppm.

Example 21

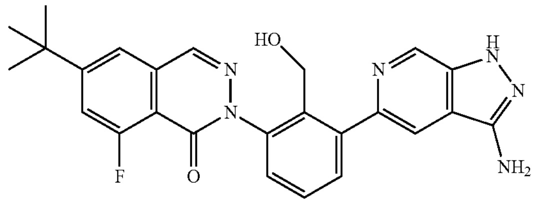 [SMILES: CC(C)(C)c1cc(F)c2c(=O)n(-c3cccc(-c4cc5c(N)n[nH]c5cn4)c3CO)ncc2c1]

2-[3-(3-amino-1H-pyrazolo[3,4-c]pyridin-5-yl)-2-(hydroxymethyl)phenyl]-6-tert-butyl-8-fluorophthalazin-1(2H)-one Step 1: N-(6-chloro-4-methylpyridin-3-yl)acetamide To a solution of 6-chloro-4-methylpyridin-3-amine (300 mg, 2.104 mmol) in acetic acid (10 mL) was added acetic anhydride (430 mg, 4.21 mmol). Then the mixture was stirred at 10-15° C. for 1 hour. The solvent was removed to give crude N-(6-chloro-4-methylpyridin-3-yl)acetamide, which was used directly in the next step.

Step 2: 1-(5-chloro-1H-pyrazolo[3,4-c]pyridin-1-yl) ethanone

To a solution of N-(6-chloro-4-methylpyridin-3-yl)acetamide (1.94 g, 10.51 mmol) in $CHCl_3$ (100 mL) was added acetic anhydride (0.595 mL, 6.30 mmol) at 0° C. The resulting mixture was stirred for 1 hour at 25-30° C. Then isopentyl nitrite (2.71 g, 23.12 mmol) and potassium acetate (0.206 g, 2.102 mmol) were added. The reaction mixture was stirred at 70-80° C. for 18 hours. The solvent was removed and to the residue was added EtOAc (100 mL). The resulting mixture was washed with water (30 mL×2), brine (30 mL×2), dried over $Na_2SO_4$, filtered and concentrated. The residue was purified by flash column chromatography (EtOAc inPE=0%-10%) to give 1-(5-chloro-1H-pyrazolo[3,4-c]pyridin-1-yl)ethanone. $^1$HNMR (400 MHz, $CDCl_3$) δ 9.56 (s, 1H), 8.15 (s, 1H), 7.69 (s, 1H), 2.81 (s, 3H) ppm.

Step 3: 5-chloro-3-nitro-1H-pyrazolo[3,4-c]pyridine

To a solution of 1-(5-chloro-1H-pyrazolo[3,4-c]pyridin-1-yl)ethanone (600 mg, 3.07 mmol) in sulfuric acid (10 mL, 188 mmol) was slowly added nitric acid (1.6 mL, 25.06 mmol) at 0° C. The resulting mixture was stirred at 70-80° C. for 2 hours, then cooled to 0° C. The mixture was then poured into water (200 mL) slowly, extracted with EtOAc (100 mL×2). The combined organic layers were dried over $Na_2SO_4$ and concentrated to give 5-chloro-3-nitro-1H-pyrazolo[3,4-c]pyridine. $^1H$ NMR (400 MHz, DMSO-$d_6$) δ 8.84 (s, 1H), 7.72 (s, 1H) ppm.

Step 4: 2-(6-(tert-butyl)-8-fluoro-1-oxophthalazin-2(1H)-yl)-6-(3-nitro-1H-pyrazolo[3,4-c]pyridin-5-yl) benzyl acetate To a solution of 5-chloro-3-nitro-1H-pyrazolo[3,4-c]pyridine (630 mg, 3.17 mmol) in dioxane (10 mL) and water (1 mL) were added 2-(6-(tert-butyl)-8-fluoro-1-oxophthalazin-2(1H)-yl)-6-(4,4,5,5-tetramethyl-1,3,2-dioxaborolan-2-yl) benzyl acetate (1882 mg, 3.81 mmol), X-phos (302 mg, 0.635 mmol), $Pd_2(dba)_3$ (581 mg, 0.635 mmol) and $K_3PO_4$ (2.02 g, 9.52 mmol) under $N_2$. The reaction mixture was stirred for 30 min at 125° C. under microwave. The reaction mixture was poured into water (50 mL) and extracted with EtOAc (20 mL×2). The combined organic layers were dried over $Na_2SO_4$ and concentrated to give crude 2-(6-(tert-butyl)-8-fluoro-1-oxophthalazin-2(1H)-yl)-6-(3-nitro-1H-pyrazolo[3,4-c]pyridin-5-yl)benzyl acetate, which was used directly in the next step. MS-ESI(m/z): 531.2 $(M+H)^+$ (Method B; Rt: 1.143 min).

Step 5: 6-(tert-butyl)-8-fluoro-2-(2-(hydroxymethyl)-3-(3-nitro-1H-pyrazolo[3,4-c]pyridin-5-yl)phenyl)phthalazin-1(2H)-one To a solution of 2-(6-(tert-butyl)-8-fluoro-1-oxophthalazin-2(1H)-yl)-6-(3-nitro-1H-pyrazolo[3,4-c]pyridin-5-yl)benzyl acetate (400 mg, 0.754 mmol) in THF (10 mL) was added aqueous lithium hydroxide (15 mL, 30.0 mmol)). The reaction mixture was stirred for 18 hours at 18° C., then poured into water (50 mL) and extracted with EtOAc (20 mL×2). The combined organic layers were dried over $Na_2SO_4$, filtered and concentrated. The residue was purified by Prep-HPLC to give 6-(tert-butyl)-8-fluoro-2-(2-(hydroxymethyl)-3-(3-nitro-1H-pyrazolo[3,4-c]pyridin-5-yl)phenyl)phthalazin-1(2H)-one. MS-ESI(m/z): 489 $(M+1)^+$ (Method B; Rt: 1.122 min).

Step 6: 2-(3-(3-amino-1H-pyrazolo[3,4-c]pyridin-5-yl)-2-(hydroxymethyl)phenyl)-6-(tert-butyl)-8-fluorophthalazin-1(2H)-one A mixture of 6-(tert-butyl)-8-fluoro-2-(2-(hydroxymethyl)-3-(3-nitro-1H-pyrazolo [3,4-c]pyridin-5-yl)phenyl) phthalazin-1(2H)-one (12 mg, 0.025 mmol), sodium bicarbonate (2.476 mg, 0.029 mmol) and Pd/C (0.523 mg, 4.91 μmol) in ethanol (5 mL) was stirred under $H_2$ (15 psi) at 14° C. for 16 h. The reaction mixture was filtered, and the filtrate was purified by Prep-HPLC to give 2-(3-(3-amino-1H-pyrazolo[3,4-c]pyridin-5-yl)-2-(hydroxymethyl)phenyl)-6-(tert-butyl)-8-fluorophthalazin-1(2H)-one. MS-ESI(m/z): 459 $(M+1)^+$(Method A; Rt: 2.454 min). $^1$H NMR (400 MHz, $CD_3OD$) δ 9.00 (s, 1H), 8.48 (d, J=1.96 Hz, 1H), 8.26 (s, 1H), 7.84 (s, 1H), 7.63-7.74 (m, 3H), 7.58 (d, J=7.43 Hz, 1H), 4.39 (s, 2H), 1.43 (s, 9H) ppm.

Example 22

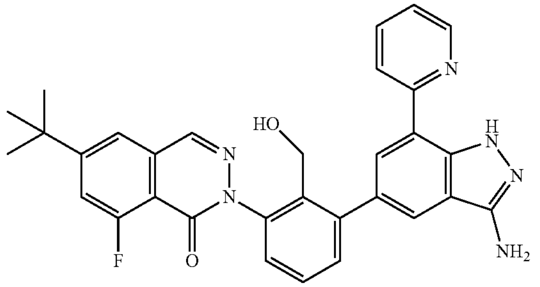 [SMILES: CC(C)(C)c1cc(F)c2c(=O)n(-c3cccc(-c4cc(-c5ccccn5)c5[nH]nc(N)c5c4)c3CO)ncc2c1]

2-(3-(3-amino-7-(pyridin-2-yl)-1H-indazol-5-yl)-2-(hydroxymethyl)phenyl)-6-(tert-butyl)-8-fluorophthalazin-1(2H)-one Step 1: 5-bromo-7-(pyridin-2-yl)-1H-indazol-3-amine To a solution of 5-bromo-7-iodo-1H-indazol-3-amine (200 mg, 0.592 mmol) in dioxane (10 mL) was added 2-(tributylstannyl)pyridine (240 mg, 0.651 mmol) and bis (triphenylphosphine)palladium(II) dichloride (41.5 mg, 0.059 mmol). The mixture was stirred at 120° C. for 1 h under microwave irradiation. The reaction mixture was poured into water (20 mL) and extracted with EtOAc (20 mL×2). The combined organic layers were dried and concentrated. The residue was purified by flash column chromatography (MeOH in DCM: 0-10%) to give 5-bromo-7-(pyridin-2-yl)-1H-indazol-3-amine. MS-ESI(m/z): 290 (M+H)+(Method B; Rt: 0.969 min).

Step 2: 2-(3-amino-7-(pyridin-2-yl)-1H-indazol-5-yl)-6-(6-(tert-butyl)-8-fluoro-1-oxophthalazin-2(1H)-yl)benzyl acetate To a solution of 2-(6-(tert-butyl)-8-fluoro-1-oxophthalazin-2(1H)-yl)-6-(4,4,5,5-tetramethyl-1,3,2-dioxaborolan-2-yl)benzyl acetate (349 mg, 0.706 mmol) in 1,4-dioxane (2 mL) and water (0.5 mL) was added 5-bromo-7-(pyridin-2-yl)-1H-indazol-3-amine (170 mg, 0.588 mmol), $Pd_2(dba)_3$ (108 mg, 0.118 mmol), 2-(dicyclohexylphosphino)-2',4',6'-triisopropylbiphenyl (56.1 mg, 0.118 mmol) and potassium phosphate (374 mg, 1.764 mmol). Then the reaction mixture was stirred for 30 min at 125° C. in microwave. The reaction mixture was poured into water and extracted with EtOAc (20 mL×2). The combined organic layers were dried and concentrated. The residue was purified by flash column chromatography (MeOH in DCM: 0-10%) to give 2-(3-amino-7-(pyridin-2-yl)-1H-indazol-5-yl)-6-(6-(tert-butyl)-8-fluoro-1-oxophthalazin-2(1H)-yl)benzyl acetate. MS-ESI(m/z): 577 (M+H)+(Method B; Rt: 1.105 min).

Step 3: 2-(3-(3-amino-7-phenyl-1H-indazol-5-yl)-2-(hydroxymethyl)phenyl)-6-(tert-butyl)-8-fluorophthalazin-1(2H)-one To a solution of 2-(3-amino-7-(pyridin-2-yl)-1H-indazol-5-yl)-6-(6-(tert-butyl)-8-fluoro-1-oxophthalazin-2(1H)-yl) benzyl acetate (200 mg, 0.347 mmol) in THF (10 mL) was added lithium hydroxide, $H_2O$ (10 mL, 20.00 mmol). The reaction mixture was stirred for 18 h at 21° C., then poured into water (50 mL) and extracted with EtOAc (20 mL×2). The combined organic layers were dried over $Na_2SO_4$, filtered, concentrated and purified by Prep-HPLC to give 2-(3-(3-amino-7-(pyridin-2-yl)-1H-indazol-5-yl)-2-(hydroxymethyl)phenyl)-6-(tert-butyl)-8-fluorophthalazin-1(2H)-one. MS-ESI(m/z): 535 $(M+H)^+$(Acq Method D; Rt: 1.199 min). $^1$H NMR ($CD_3OD$, 400 MHz) δ: 8.77 (d, J=3.9 Hz, 1H), 8.48 (d, J=2.0 Hz, 1H), 8.42 (s, 1H), 8.17 (d, J=8.2 Hz, 1H), 8.06 (s, 1H), 7.94 (t, J=7.0 Hz, 1H), 7.83 (s, 1H), 7.69 (d, J=12.9 Hz, 1H), 7.63-7.55 (m, 2H), 7.47 (dd, J=2.0, 6.7 Hz, 1H), 7.39 (dd, J=5.5, 7.0 Hz, 1H), 4.43 (br. s., 2H), 1.43 (s, 9H) ppm.

Example 23

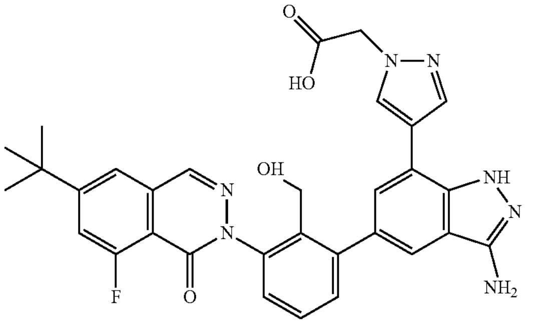 [SMILES: CC(C)(C)c1cc(F)c2c(=O)n(-c3cccc(-c4cc(-c5cnn(CC(=O)O)c5)c5[nH]nc(N)c5c4)c3CO)ncc2c1]

2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)acetic acid Step 1: methyl 2-(4-(3-amino-5-bromo-1H-indazol-7-yl)-1H-pyrazol-1-yl) acetate To a solution of 5-bromo-7-iodo-1H-indazol-3-amine (100 mg, 0.296 mmol), methyl 2-(4-(4,4,5,5-tetramethyl-1,3,2-dioxaborolan-2-yl)-1H-pyrazol-1-yl)acetate (94 mg, 0.355 mmol) and $K_2CO_3$ (123 mg, 0.888 mmol) in water (0.6 mL) and 1,4-dioxane (2.4 mL) was added $Pd(dppf)Cl_2$ (21.65 mg, 0.030 mmol) under $N_2$. The mixture was stirred at 40° C. for 16 hours. TLC (DCM/THF=1:1) showed the reaction was complete, and then the mixture was diluted with $H_2O$ (10 mL), and extracted with EtOAc (10 mL×4). The organic layer was washed with brine (10 mL), dried over $Na_2SO_4$, concentrated to give a crude product, which was then purified by flash chromatography (DCM/

THF=60~50%) to afford the title compound. $^1$H NMR (400 MHz, $CDCl_3$) δ 9.93 (br. s., 1H), 7.93 (d, J=9.8 Hz, 2H), 7.53 (s, 1H), 7.43 (s, 1H), 4.99 (s, 2H), 4.14 (br. s., 2H), 3.71 (s, 3H) ppm.

Step 2: 2-(4-(5-(2-(acetoxymethyl)-3-(6-(tert-butyl)-8-fluoro-1-oxophthalazin-2(1H)-yl)phenyl)-3-amino-1H-indazol-7-yl)-1H-pyrazol-1-yl)acetic acid To a solution of methyl 2-(4-(3-amino-5-bromo-1H-indazol-7-yl)-1H-pyrazol-1-yl)acetate (60 mg, 0.171 mmol), 2-(6-(tert-butyl)-8-fluoro-1-oxophthalazin-2(1H)-yl)-6-(4,4,5,5-tetramethyl-1,3,2-dioxaborolan-2-yl)benzyl acetate (102 mg, 0.206 mmol) and potassium phosphate monohydrate (137 mg, 0.514 mmol) in 1,4-dioxane (2.5 ml) and water (0.5 mL) was added X-Phos (16.34 mg, 0.034 mmol) and $Pd_2(dba)_3$ (15.69 mg, 0.017 mmol) under $N_2$. The reaction vessel was sealed and heated at 125° C. for 30 min. LCMS showed the reaction was complete, and the mixture was diluted with $H_2O$ (5 mL), and extracted with DCM (10 mL×4). The aqueous layer was evaporated to afford the title compound. MS: 624.3 $(M+1)^+$.

Step 3: 2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)acetic acid A mixture of 2-(4-(5-(2-(acetoxymethyl)-3-(6-(tert-butyl)-8-fluoro-1-oxophthalazin-2(1H)-yl)phenyl)-3-amino-1H-indazol-7-yl)-1H-pyrazol-1-yl)acetic acid (100 mg) in THF (5 mL) and lithium hydroxide, $H_2O$ (2.5 mL, 5.00 mmol) was stirred at 25° C. for 4 hours. LCMS showed that most of the starting material was consumed and the desired compound formed. After concentration, the residual aqueous layer was separated by Prep-HPLC to give title compound. MS: 582.2 $(M+1)^+$. $^1$H NMR (400 MHz, $CD_3OD$) δ 8.47 (d, J=2.0 Hz, 1H), 8.20 (s, 1H), 8.03 (s, 1H), 7.88 (s, 1H), 7.84 (d, J=8.2 Hz, 2H), 7.69 (d, J=13.3 Hz, 1H), 7.61-7.51 (m, 2H), 7.45 (d, J=7.0 Hz, 1H), 5.06 (s, 2H), 4.43 (br. s., 2H), 1.43 (s, 9H) ppm.

Example 24

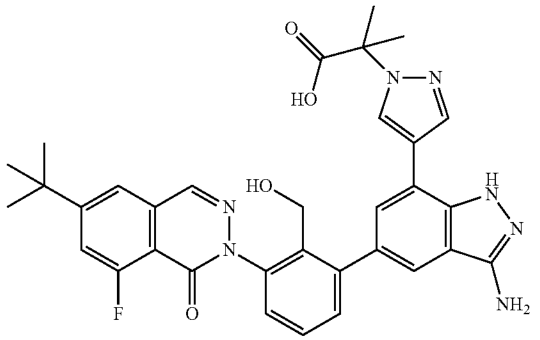 [SMILES: CC(C)(C)c1cc(F)c2c(=O)n(-c3cccc(-c4cc(-c5cnn(C(C)(C)C(=O)O)c5)c5[nH]nc(N)c5c4)c3CO)ncc2c1]

2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)-2-methylpropanoic acid Step 1: methyl 2-(4-(3-amino-5-bromo-1H-indazol-7-yl)-1H-pyrazol-1-yl)-2-methylpropanoate To a solution of methyl 2-methyl-2-(4-(4,4,5,5-tetramethyl-1,3,2-dioxaborolan-2-yl)-1H-pyrazol-1-yl)propanoate (209 mg, 0.710 mmol) and 5-bromo-7-iodo-1H-indazol-3-amine (200 mg, 0.592 mmol) in 1,4-dioxane (6.4 mL) and water (1.6 mL) was added $K_2CO_3$ (327 mg, 2.367 mmol) and $Pd(dppf)Cl_2$ (43.3 mg, 0.059 mmol) under $N_2$. The mixture was stirred at 40° C. for 16 hours, then diluted with $H_2O$ (10 mL) and EtOAc (10 mL), the mixture was filtered and the filtrate was extracted with EtOAc (10 mL×3). The organic layer was washed with brine (10 mL), dried over $Na_2SO_4$, evaporated to give a crude product, which was then purified by flash chromatography (DCM/THF=65~60%) to afford the title compound. $^1$H NMR (400 MHz, $CDCl_3$) δ 10.42 (br. s., 1H), 8.05 (s, 1H), 7.95 (s, 1H), 7.41 (d, J=16.8 Hz, 2H), 3.66 (s, 3H), 1.86 (s, 6H) ppm.

Step 2: methyl 2-(4-(5-(2-(acetoxymethyl)-3-(6-(tert-butyl)-8-fluoro-1-oxophthalazin-2(1H)-yl)phenyl)-3-amino-1H-indazol-7-yl)-1H-pyrazol-1-yl)-2-methylpropanoate To a solution of methyl 2-(4-(3-amino-5-bromo-1H-indazol-7-yl)-1H-pyrazol-1-yl)-2-methyl propanoate (100 mg, 0.264 mmol), 2-(6-(tert-butyl)-8-fluoro-1-oxophthalazin-2(1H)-yl)-6-(4,4,5,5-tetramethyl-1,3,2-dioxaborolan-2-yl)benzyl acetate (144 mg, 0.291 mmol) and potassium phosphate monohydrate (211 mg, 0.793 mmol) in 1,4-dioxane (2.5 mL) and water (0.5 mL) was added X-Phos (25.2 mg, 0.053 mmol) and $Pd_2(dba)_3$ (24.21 mg, 0.026 mmol) under $N_2$ and the reaction vessel was sealed and heated in microwave at 125° C. for 30 min. The mixture was diluted with $H_2O$ (5 mL) and DCM (10 mL), filtered, and the filtrate was extracted with DCM/MeOH (10 mL×4, 10:1). The organic layer was washed with brine (10 mL), dried over $Na_2SO_4$, and evaporated to afford the title compound. MS: 666.4 $(M+1)^+$.

Step 3: 2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)-2-methylpropanoic acid To a solution of methyl 2-(4-(5-(2-(acetoxymethyl)-3-(6-(tert-butyl)-8-fluoro-1-oxophthalazin-2(1H)-yl)phenyl)-3-amino-1H-indazol-7-yl)-1H-pyrazol-1-yl)-2-methylpropanoate (150 mg) in THF (0.8 mL) was added lithium hydroxide, $H_2O$ (0.451 mL, 0.901 mmol) and the mixture was stirred at 20° C. for 12 hours. The mixture was evaporated to give a crude product, which was then purified by Prep-HPLC to afford the title compound. LCMS Method A, Retention time: 2.471 min, (M+H)+m/z: 610.2. $^1$H NMR (400 MHz, $CD_3OD$) δ 8.50-8.44 (m, 1H), 8.35 (s, 1H), 8.04 (s, 1H), 7.94 (br. s., 1H), 7.84 (d, J=10.6 Hz, 2H), 7.69 (d, J=12.9 Hz, 1H), 7.59-7.51 (m, 2H), 7.45 (d, J=7.0 Hz, 1H), 4.43 (br. s., 2H), 1.95-1.87 (m, 6H), 1.43 (s, 9H) ppm.

Example 25

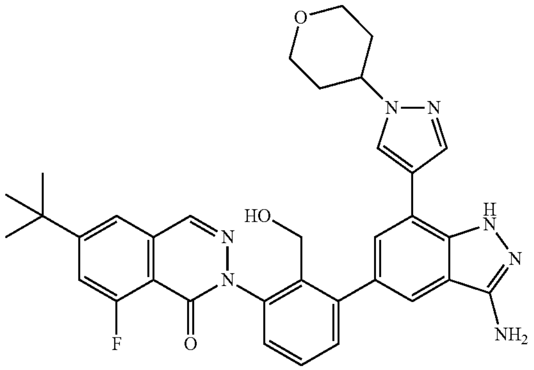 [SMILES: CC(C)(C)c1cc(F)c2c(=O)n(-c3cccc(-c4cc(-c5cnn(C6CCOCC6)c5)c5[nH]nc(N)c5c4)c3CO)ncc2c1]

2-(3-(3-amino-7-(1-(tetrahydro-2H-pyran-4-yl)-1H-pyrazol-4-yl)-1H-indazol-5-yl)-2-(hydroxymethyl)phenyl)-6-(tert-butyl)-8-fluorophthalazin-1(2H)-one Step 1: tetrahydro-2H-pyran-4-yl 4-methylbenzenesulfonate To a solution of tetrahydro-2H-pyran-4-ol (1.20 g, 11.7 mmol) in pyridine (13 mL) was added a solution of 4-methylbenzene-1-sulfonyl chloride (3.36 g, 17.6 mmol) in DCM (10 mL) dropwise at 10° C. After addition, the reaction mixture was warmed to room temperature and stirred for 18 h. The mixture was poured onto a stirred mixture of aqueous HCl/ice. The resulting precipitate was isolated by filtration. The filter cake was then dissolved in DCM (20 mL×2). The organic layer was washed with 1N HCl (15 mL), and satd. aq.$NaHCO_3$ (20 mL). The organic layer was dried over anhydrous sodium sulfate and concentrated. The residue was purified by column chromatography on silica gel (eluting with PE/EtOAc=100:1-10:1) to give tetrahydro-2H-pyran-4-yl 4-methylbenzenesulfonate. $^1H$ NMR (400 MHz, $CDCl_3$) δ 7.81 (d, J=8.2 Hz, 2H), 7.35 (d, J=7.8 Hz, 2H), 4.69 (tt, J=4.1, 8.1 Hz, 1H), 3.93-3.81 (m, 2H), 3.47 (ddd, J=2.9, 8.6, 11.5 Hz, 2H), 2.60-2.32 (m, 3H), 1.95-1.81 (m, 2H), 1.81-1.68 (m, 2H) ppm.

Step 2:4-bromo-1-(tetrahydro-2H-pyran-4-yl)-1H-pyrazole

To a solution of 4-bromo-1H-pyrazole (844 mg, 5.78 mmol) in DMF (15 mL) was added tetrahydro-2H-pyran-4-yl 4-methylbenzenesulfonate (1.48 g, 5.78 mmol) and $Cs_2CO_3$ (2.82 g, 8.67 mmol)). The mixture was stirred at 60° C. for 16 hours, then diluted with water (30 mL) and extracted with ethyl acetate (30 mL×3). The combined organic layers were washed with brine (40 mL×2), dried over anhydrous sodium sulfate and concentrated. The residue was purified by column chromatography on silica gel (eluting withPE/EtOAc=100%-60%) to give 4-bromo-1-(tetrahydro-2H-pyran-4-yl)-1H-pyrazole. MS ESI calc'd. for $C_8H_{12}BrN_2O$ $[M+H]^+$231 and 233, found 231 and 233. (Method B; Rt:1.015 min). $^1H$ NMR (400 MHz, $CDCl_3$) δ 7.47 (d, J=7.4 Hz, 2H), 4.38-4.26 (m, 1H), 4.11 (d, J=11.0 Hz, 2H), 3.54 (dt, J=2.2, 11.6 Hz, 2H), 2.12-2.01 (m, 4H) ppm.

Step 3:1-(tetrahydro-2H-pyran-4-yl)-4-(4,4,5,5-tetramethyl-1,3,2-dioxaborolan-2-yl)-1H-pyrazole To a solution of 4-bromo-1-(tetrahydro-2H-pyran-4-yl)-1H-pyrazole (300 mg, 1.30 mmol) in 1,4-dioxane (15 mL) were added bispinacolatediborone (396 mg, 1.56 mmol), AcOK (382 mg, 3.89 mmol) and $Pd(dppf)Cl_2$ (84.6 mg, 0.130 mmol). The mixture was stirred at 120° C. under $N_2$ for 16 hours. After cooling to room temperature, the mixture was concentrated. The residue was purified by column chromatography on silica gel (eluting with PE/EtOAc=100%-50%) to give 1-(tetrahydro-2H-pyran-4-yl)-4-(4,4,5,5-tetramethyl-1,3,2-dioxaborolan-2-yl)-1H-pyrazole. MS ESI calc'd. for $C_{14}H_{24}B_2N_2O_3$ $[M+H]^+$279, found 279. (Method B; Rt:1.102 min). $^1H$ NMR (400 MHz, $CDCl_3$) δ 7.81 (s, 1H), 7.76 (s, 1H), 4.43-4.29 (m, 1H), 4.11 (d, J=10.2 Hz, 2H), 3.55 (t, J=10.6 Hz, 2H), 2.13-2.04 (m, 4H), 1.33 (s, 12H) ppm.

Step 4:5-bromo-7-(1-(tetrahydro-2H-pyran-4-yl)-1H-pyrazol-4-yl)-1H-indazol-3-amine To a solution of 5-bromo-7-iodo-1H-indazol-3-amine (150 mg, 0.444 mmol) in 1,4-dioxane (3 mL) and $H_2O$ (1 mL) was added 1-(tetrahydro-2H-pyran-4-yl)-4-(4,4,5,5-tetramethyl-1,3,2-dioxaborolan-2-yl)-1H-pyrazole (148 mg, 0.533 mmol), $K_2CO_3$(184 mg, 1.33 mmol) and $Pd(dppf)Cl_2$ (28.9 mg, 0.044 mmol) under an $N_2$ atmosphere. The mixture was stirred at 125° C. under $N_2$ for 30 min under microwave irradiation. The mixture was diluted with water (5 mL) and extracted with ethyl acetate (5 mL×2). The combined organic layers were washed with brine (10 mL×2), dried over anhydrous sodium sulfate and concentrated. The residue was purified by column chromatography on silica gel (eluting with PE/THF=100%-80%) to give 5-bromo-7-(1-(tetrahydro-2H-pyran-4-yl)-1H-pyrazol-4-yl)-1H-indazol-3-amine. MS ESI calc'd. for $C_{15}H_{17}BrN_5O$ $[M+H]^+$362 and 364, found 362 and 364. (Method B; Rt:1.012 min). $^1H$ NMR (400 MHz, $CD_3OD$ δ 8.24 (s, 1H), 7.99 (s, 1H), 7.77 (d, J=1.5 Hz, 1H), 7.58 (d, J=1.5 Hz, 1H), 4.54-4.43 (m, 1H), 4.14-4.05 (m, 2H), 3.61 (dt, J=2.9, 11.5 Hz, 2H), 2.23-2.07 (m, 4H) ppm.

Step 5: 2-(3-amino-7-(1-(tetrahydro-2H-pyran-4-yl)-1H-pyrazol-4-yl)-1H-indazol-5-yl)-6-(6-(tert-butyl)-8-fluoro-1-oxophthalazin-2(1H)-yl)benzyl acetate To a solution of 5-bromo-7-(1-(tetrahydro-2H-pyran-4-yl)-1H-pyrazol-4-yl)-1H-indazol-3-amine (110 mg, 0.304 mmol) in 1,4-dioxane (3 mL) and $H_2O$ (0.3 mL) was added 2-(6-(tert-butyl)-8-fluoro-1-oxophthalazin-2(1H)-yl)-6-(4,4,5,5-tetramethyl-1,3,2-dioxaborolan-2-yl)benzyl acetate (180 mg, 0.364 mmol), $K_3PO_4$(193 mg, 0.911 mmol), $Pd_2(dba)_3$ (55.6 mg, 0.061 mmol) and X-Phos (28.9 mg, 0.061 mmol) under an $N_2$ atmosphere. The mixture was stirred at 120° C. under $N_2$ for 30 min under microwave irradiation. The mixture was diluted with water (10 mL) and extracted with ethyl acetate (15 mL×2). The combined organic layers were washed with brine (20 mL×2), dried over anhydrous sodium sulfate and concentrated. The residue was purified by column chromatography on silica gel (eluting with DCM/MeOH=100%~90%) to give 2-(3-amino-7-(1-(tetrahydro-2H-pyran-4-yl)-1H-pyrazol-4-yl)-1H-indazol-5-yl)-6-(6-(tert-butyl)-8-fluoro-1-oxophthalazin-2(1H)-yl)benzyl acetate. MS ESI calc'd. for $C_{36}H_{37}FN_7O_4$ $[M+H]^+$650, found 650. (Method B; Rt:1.202 min).

Step 6: 2-(3-(3-amino-7-(1-(tetrahydro-2H-pyran-4-yl)-1H-pyrazol-4-yl)-1H-indazol-5-yl)-2-(hydroxymethyl)phenyl)-6-(tert-butyl)-8-fluorophthalazin-1(2H)-one To a solution of 2-(3-amino-7-(1-(tetrahydro-2H-pyran-4-yl)-1H-pyrazol-4-yl)-1H-indazol-5-yl)-6-(6-(tert-butyl)-8-fluoro-1-oxophthalazin-2(1H)-yl)benzyl acetate (110 mg, 0.169 mmol) in THF (10 mL) was added aq.LiOH (2 N, 10 mL). The reaction mixture was stirred at 20° C. for 16 hours. The mixture was cooled to room temperature and concentrated. The residue was purified by Prep-HPLC to give 2-(3-(3-amino-7-(1-(tetrahydro-2H-pyran-4-yl)-1H-pyrazol-4-yl)-1H-indazol-5-yl)-2-(hydroxymethyl)phenyl)-6-(tert-butyl)-8-fluorophthalazin-1(2H)-one. MS ESI calc'd. for $C_{34}H_{35}FN_7O_3$ $[M+H]^+$608, found 608. (Method A; Rt:2.830 min). $^1H$ NMR (400 MHz, $CD_3OD$) δ 8.45 (d, J=2.0 Hz, 1H), 8.23 (s, 1H), 8.00 (s, 1H), 7.88 (s, 1H), 7.81 (d, J=4.3 Hz, 2H), 7.67 (d, J=12.9 Hz, 1H), 7.58-7.48 (m, 2H), 7.42 (d, J=7.4 Hz, 1H), 4.51-4.33 (m, 3H), 4.05 (d, J=11.0 Hz, 2H), 3.56 (dt, J=2.7, 11.3 Hz, 2H), 2.18-2.01 (m, 4H), 1.41 (s, 9H) ppm.

Example 26

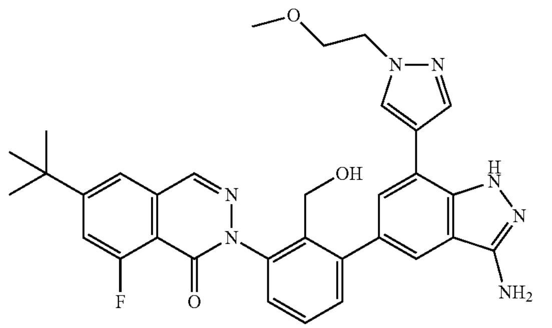 [SMILES: COCCn1cc(-c2cc(-c3cccc(-n4ncc5cc(C(C)(C)C)cc(F)c5c4=O)c3CO)cc3c(N)n[nH]c23)cn1]

2-(3-(3-amino-7-(1-(2-methoxyethyl)-1H-pyrazol-4-yl)-1H-indazol-5-yl)-2-(hydroxymethyl)phenyl)-6-(tert-butyl)-8-fluorophthalazin-1(2H)-one Step 1: 5-bromo-7-(1-(2-methoxyethyl)-1H-pyrazol-4-yl)-1H-indazol-3-amine To a solution of 5-bromo-7-iodo-1H-indazol-3-amine (147 mg, 0.436 mmol) in THF (3 mL) and water (0.5 mL) was added 1-(2-methoxyethyl)-4-(4,4,5,5-tetramethyl-1,3,2-dioxaborolan-2-yl)-1H-pyrazole (100 mg, 0.397 mmol), $PdCl_2$(dppf) (29.0 mg, 0.040 mmol) and $K_2CO_3$ (110 mg, 0.793 mmol). The reaction mixture was stirred for 30 min at 100° C. under microwave irradiation. The reaction mixture was poured into water (20 mL) and extracted with EtOAc (20 mL×2). The combined organic layers were dried and concentrated. The residue was purified by flash column chromatography (MeOH in DCM: 0-10%) to give 5-bromo-7-(1-(2-methoxyethyl)-1H-pyrazol-4-yl)-1H-indazol-3-amine. MS-ESI(m/z): 337 $(M+H)^+$(Method B; Rt: 0.886 min).

Step 2: 2-(3-amino-7-(1-(2-methoxyethyl)-1H-pyrazol-4-yl)-1H-indazol-5-yl)-6-(6-(tert-butyl)-8-fluoro-1-oxophthalazin-2(1H)-yl)benzyl acetate To a solution of 2-(6-(tert-butyl)-8-fluoro-1-oxophthalazin-2(1H)-yl)-6-(4,4,5,5-tetramethyl-1,3,2-dioxaborolan-2-yl)benzyl acetate (176 mg, 0.357 mmol) in 1,4-dioxane (2 mL) and water (0.5 mL) was added 5-bromo-7-(1-(2-methoxyethyl)-1H-pyrazol-4-yl)-1H-indazol-3-amine (100 mg, 0.297 mmol), $Pd_2(dba)_3$ (54.5 mg, 0.059 mmol), 2-(dicyclohexylphosphino)-2',4',6'-triisopropylbiphenyl (28.4 mg, 0.059 mmol) and potassium phosphate (189 mg, 0.892 mmol). Then the reaction mixture was stirred for 30 min at 125° C. under microwave irradiation. The reaction mixture was poured into water (50 mL) and extracted with EtOAc (20 mL×2). The combined organic layers were dried and concentrated. The residue was purified by flash column chromatography (MeOH in DCM: 0-10%) to give 2-(3-amino-7-(1-(2-methoxyethyl)-1H-pyrazol-4-yl)-1H-indazol-5-yl)-6-(6-(tert-butyl)-8-fluoro-1-oxophthalazin-2(1H)-yl)benzyl acetate. MS-ESI (m/z): 624 $(M+H)^+$(Method B; Rt: 1.160 min).

Step 3: 2-(3-(3-amino-7-(1-(2-methoxyethyl)-1H-pyrazol-4-yl)-1H-indazol-5-yl)-2-(hydroxymethyl)phenyl)-6-(tert-butyl)-8-fluorophthalazin-1(2H)-one To a solution of 2-(3-amino-7-(1-(2-methoxyethyl)-1H-pyrazol-4-yl)-1H-indazol-5-yl)-6-(6-(tert-butyl)-8-fluoro-1- oxophthalazin-2(1H)-yl)benzyl acetate (100 mg, 0.160 mmol) in THF (5 mL) was added aq. lithium hydroxide (1 mmol, 1 mL). Then the reaction mixture was stirred for 18 h at 18° C. The mixture was poured into water (50 mL) and extracted with EtOAc (20 mL×2). The combined organic layers were dried over $Na_2SO_4$, filtered, concentrated and purified by Prep-HPLC to give 2-(3-(3-amino-7-(1-(2-methoxyethyl)-1H-pyrazol-4-yl)-1H-indazol-5-yl)-2-(hydroxymethyl)phenyl)-6-(tert-butyl)-8-fluorophthalazin-1(2H)-one. MS-ESI (m/z): 582 $(M+H)^+$(Method B; Rt: 1.158 min). $^1H$ NMR (400 MHz, $CD_3OD$) δ 8.47 (d, J=2.0 Hz, 1H), 8.17 (s, 1H), 8.00 (s, 1H), 7.87 (s, 1H), 7.82 (s, 2H), 7.68 (d, J=13.3 Hz, 1H), 7.59-7.49 (m, 2H), 7.44 (d, J=7.4 Hz, 1H), 4.48-4.33 (m, 4H), 3.78 (t, J=5.1 Hz, 2H), 3.32 (s, 3H), 1.43 (s, 9H).

Example 27

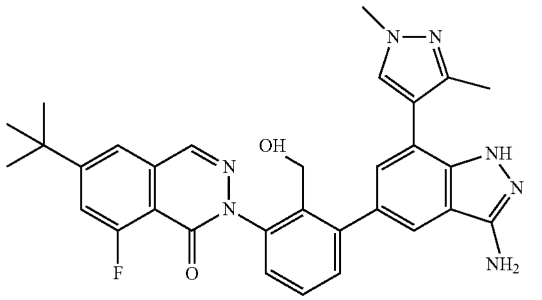 [SMILES: Cc1nn(C)cc1-c1cc(-c2cccc(-n3ncc4cc(C(C)(C)C)cc(F)c4c3=O)c2CO)cc2c(N)n[nH]c12]

2-(3-(3-amino-7-(1,3-dimethyl-1H-pyrazol-4-yl)-1H-indazol-5-yl)-2-(hydroxymethyl)phenyl)-6-(tert-butyl)-8-fluorophthalazin-1(2H)-one Step 1: 4-bromo-1,3-dimethyl-1H-pyrazole To a solution of 1,3-dimethyl-1H-pyrazole-4-carbaldehyde (2 g, 16 mmol) in $H_2O$ (4 mL) was added NaOH (1.92 g, 46 mmol), followed by dropwise addition of $Br_2$(0.8 mL, 16 mmol) at 10-20° C. The mixture was stirred at rt for 12 h, then extracted with $CH_2Cl_2$(3×40 mL), the organic layer was dried over $Na_2SO_4$, the solvent was removed and residue was purified by flash column chromatography (THF/PE=0-30%) to give 4-bromo-1,3-dimethyl-1H-pyrazole. $^1H$ NMR (400 MHz, $CDCl_3$) δ 7.29 (s, 1H), 3.81 (s, 3H), 2.22 (s, 3H) ppm.

Step 2: 1,3-dimethyl-4-(4,4,5,5-tetramethyl-1,3,2-dioxaborolan-2-yl)-1H-pyrazole To a solution of 4-bromo-1,3-dimethyl-1H-pyrazole (2 g, 16 mmol), 4,4,4',4',5,5,5',5'-octamethyl-2,2'-bi(1,3,2-dioxaborolane) (6.5 g, 25.7 mmol), AcOK (1.1 g, 38 mmol) in DMSO (40 mL) was added Pd(dppf)$Cl_2$(879 mg, 1.2 mmol) under $N_2$. The mixture was stirred at 80-90° C. for 12 h, then diluted with water (100 mL), and extracted with $CH_2Cl_2$ (3×50 mL). The organic layer was dried over $Na_2SO_4$, and the solvent was removed, The residue was purified by flash column chromatography (THF/PE=0-30%) to give 1,3-dimethyl-4-(4,4,5,5-tetramethyl-1,3,2-dioxaborolan-2-yl)-1H-pyrazole. $^1H$ NMR (400 MHz, $CDCl_3$) δ 7.54 (s, 1H), 3.81 (s, 3H), 2.37 (s, 3H), 1.29 (s, 12H) ppm.

Step 3: 5-bromo-7-(1,3-dimethyl-1H-pyrazol-4-yl)-1H-indazol-3-amine

To a solution of 1,3-dimethyl-4-(4,4,5,5-tetramethyl-1,3,2-dioxaborolan-2-yl)-1H-pyrazole (250 mg, 1.12 mmol), 5-bromo-7-iodo-1H-indazol-3-amine (316 mg, 0.93 mmol) in a mixed solution of dioxane (10 mL) and $H_2O$ (2 mL) was added $K_2CO_3$(387 mg, 2.8 mmol) and Pd(dppf) (70 mg, 0.093 mmol) under an $N_2$ atmosphere. The mixture was stirred at 40° C. for 16 h, then diluted with $H_2O$ (10 mL) and extracted with EtOAc (3×15 mL). The combined organic layers were washed with brine (20 mL), dried over $Na_2SO_4$, and evaporated to afford the crude product which was purified by flash column chromatography (THF/PE=0-60%) to give 5-bromo-7-(1,3-dimethyl-1H-pyrazol-4-yl)-1H-indazol-3-amine as a solid. $^1H$ NMR (400 MHz, $CDCl_3$) δ 7.33 (s, 1H), 6.98 (s, 2H), 5.02 (s, 1H), 3.92 (s, 3H), 2.31 (s, 2H), 2.27 (s, 3H) ppm.

Step 4: 2-(3-amino-7-(1,3-dimethyl-1H-pyrazol-4-yl)-1H-indazol-5-yl)-6-(6-(tert-butyl)-8-fluoro-1-oxophthalazin-2(1H)-yl)benzyl acetate To a solution of 5-bromo-7-(1,3-dimethyl-1H-pyrazol-4-yl)-1H-indazol-3-amine (100 mg, 0.327 mmol), 2-(6-(tert-butyl)-8-fluoro-1-oxophthalazin-2(1H)-yl)-6-(4,4,5,5-tetramethyl-1,3,2-dioxaborolan-2-yl)benzyl acetate (177 mg, 0.358 mmol) and potassium phosphate trihydrate (260 mg, 0.98 mmol) in 1,4-dioxane (3 mL) and water (0.5 mL) were added X-Phos (31 mg, 0.0651 mmol) and $Pd_2(dba)_3$ (30 mg, 0.0327 mmol) under an $N_2$ atmosphere. The reaction vessel was sealed and heated in microwave at 125° C. for 30 min. The mixture was diluted with $H_2O$ (5 mL) and DCM (10 mL), filtered, and the filtrate was extracted with DCM/MeOH (10 mL×4, 10/1). The organic layer was washed with brine (10 mL), dried over $Na_2SO_4$, evaporated to afford the title compound 2-(3-amino-7-(1,3-dimethyl-1H-pyrazol-4-yl)-1H-indazol-5-yl)-6-(6-(tert-butyl)-8-fluoro-1-oxophthalazin-2(1H)-yl)benzyl acetate, which was used directly in the next step.

Step 5: 2-(3-(3-amino-7-(1,3-dimethyl-1H-pyrazol-4-yl)-1H-indazol-5-yl)-2-(hydroxymethyl)phenyl)-6-(tert-butyl)-8-fluorophthalazin-1(2H)-one To a solution of 2-(3-amino-7-(1,3-dimethyl-1H-pyrazol-4-yl)-1H-indazol-5-yl)-6-(6-(tert-butyl)-8-fluoro-1-oxophthalazin-2(1H)-yl)benzyl acetate (40 mg, 0.067 mmol) in THF (3 mL), $H_2O$ (3 mL) was added LiOH (3.2 mg, 0.135 mmol). The mixture was stirred at 20-25° C. for 12 h. The mixture was diluted with $H_2O$ (5 mL) and DCM (10 mL) and filtered. The filtrate was extracted with DCM (10 mL×3). The organic layer was washed with brine (10 mL), and concentrated to afford a crude product which was purified by Prep-HPLC to give 2-(3-(3-amino-7-(1,3-dimethyl-1H-pyrazol-4-yl)-1H-indazol-5-yl)-2-(hydroxymethyl)phenyl)-6-(tert-butyl)-8-fluorophthalazin-1(2H)-one. $^1H$ NMR (400 MHz, $CD_3OD$) δ 8.47 (d, J=2.3 Hz, 1H), 7.90 (s, 1H), 7.87 (s, 1H), 7.83 (s, 1H), 7.69 (t, J=5.9 Hz, 2H), 7.60-7.55 (m, 1H), 7.55-7.51 (m, 1H), 7.45 (d, J=7.4 Hz, 1H), 4.44 (br. s., 2H), 3.90 (s, 3H), 2.30 (s, 3H), 1.43 (s, 9H) ppm.

Example 28

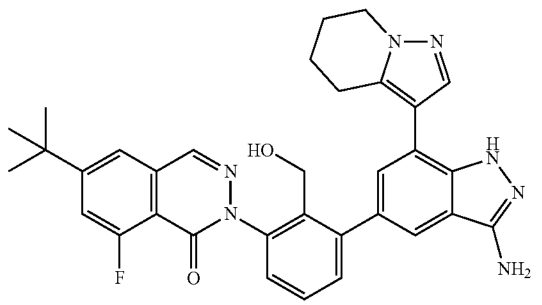 [SMILES: CC(C)(C)c1cc(F)c2c(=O)n(-c3cccc(-c4cc(-c5cnn6c5CCCC6)c5[nH]nc(N)c5c4)c3CO)ncc2c1]

2-(3-(3-amino-7-(4,5,6,7-tetrahydropyrazolo[1,5-a]pyridin-3-yl)-1H-indazol-5-yl)-2-(hydroxymethyl)phenyl)-6-(tert-butyl)-8-fluorophthalazin-1(2H)-one Step 1: 5-bromo-7-(4,5,6,7-tetrahydropyrazolo[1,5-a]pyridin-3-yl)-1H-indazol-3-amine To a mixture of 3-(4,4,5,5-tetramethyl-1,3,2-dioxaborolan-2-yl)-4,5,6,7-tetrahydropyrazolo[1,5-a]pyridine (88 mg, 0.355 mmol) and 5-bromo-7-iodo-1H-indazol-3-amine (100 mg, 0.296 mmol) in THF (3 mL) and water (0.7 mL) was added $K_2CO_3$ (123 mg, 0.888 mmol), $PdCl_2$(dppf) (21.65 mg, 0.030 mmol) under an $N_2$ atmosphere. The mixture was heated at 100° C. for 0.5 h under microwave. LCMS showed the starting material was consumed completely. The mixture was diluted with water (10 mL), and extracted with DCM (20 mL×2). The organic layer was washed with brine (40 mL), dried over $Na_2SO_4$, and concentrated in vacuo. The residue was purified by silica gel column chromatography (PE/EtOAc=3/1) to give 5-bromo-7-(4,5,6,7-tetrahydropyrazolo[1,5-a]pyridin-3-yl)-1H-indazol-3-amine as a solid. $^1H$ NMR (400 MHz, $CDCl_3$) δ 9.35 (br. s., 1H), 7.71 (s, 1H), 7.54 (s, 1H), 7.21 (br. s., 1H), 3.68 (t, J=6.1 Hz, 2H), 2.81 (t, J=6.1 Hz, 2H), 2.05 (d, J=5.1 Hz, 2H), 1.88-1.82 (m, 2H) ppm.

Step 2: 2-(3-amino-7-(4,5,6,7-tetrahydropyrazolo[1,5-a]pyridin-3-yl)-1H-indazol-5-yl)-6-(6-(tert-butyl)-8-fluoro-1-oxophthalazin-2(1H)-yl)benzyl acetate To a mixture of 2-(6-(tert-butyl)-8-fluoro-1-oxophthalazin-2(1H)-yl)-6-(4,4,5,5-tetramethyl-1,3,2-dioxaborolan-2-yl)benzyl acetate (150 mg, 0.303 mmol) and 5-bromo-7-(4,5,6,7-tetrahydropyrazolo[1,5-a]pyridin-3-yl)-1H-indazol-3-amine (101 mg, 0.303 mmol) in dioxane (2.5 mL) and water (0.25 mL) was added potassium phosphate (193 mg, 0.910 mmol), dicyclohexyl(2',4',6'-triisopropyl-[1,1'-biphenyl]-2-yl)phosphine (28.9 mg, 0.061 mmol) and $Pd_2(dba)_3$ (55.6 mg, 0.061 mmol) under an $N_2$ atmosphere. The mixture was heated at 125° C. for 0.5 h under microwave irradiation. The mixture was diluted with water (10 mL), extracted with DCM (20 mL×2). The organic layer was washed with brine (40 mL), dried over $Na_2SO_4$, concentrated in vacuo, and the residue was purified by silica gel column chromatography (PE/EtOAc=3/1) to give 2-(3-amino-7-(4,5,6,7-tetrahydropyrazolo[1,5-a]pyridin-3-yl)-1H-indazol-5-yl)-6-(6-(tert-butyl)-8-fluoro-1-oxophthalazin-2(1H)-yl)benzyl acetate. MS-ESI (m/z): $(M+1)^+$620.2 (Method B; Rt: 1.095 min).

Step 3:2-(3-(3-amino-7-(4,5,6,7-tetrahydropyrazolo [1,5-a]pyridin-3-yl)-1H-indazol-5-yl)-2-(hydroxymethyl)phenyl)-6-(tert-butyl)-8-fluorophthalazin-1 (2H)-one To a mixture of 2-(3-amino-7-(4,5,6,7-tetrahydropyrazolo [1,5-a]pyridin-3-yl)-1H-indazol-5-yl)-6-(6-(tert-butyl)-8-fluoro-1-oxophthalazin-2(1H)-yl)benzyl acetate (100 mg, 0.161 mmol) in THF (8 mL) was added a solution of aq. LiOH (0.807 mL, 1.614 mmol). The mixture was stirred at 50° C. for 15 h. LCMS showed the starting material was consumed completely, and the reaction mixture was purified by Prep-HPLC (ACN/water with 0.1% TFA modifier) to give 2-(3-(3-amino-7-(4,5,6,7-tetrahydropyrazolo[1,5-a]pyridin-3-yl)-1H-indazol-5-yl)-2-(hydroxymethyl)phenyl)-6-(tert-butyl)-8-fluorophthalazin-1(2H)-one. MS ESI calcd. for $C_{33}H_{32}FN_7O_2$ $(M+1)^+$: 578.2, found 578.3 (Method A; Rt:2.552 min). $^1H$ NMR (400 MHz, $CD_3OD$) δ 8.47 (d, J=2.0 Hz, 1H), 7.85-7.79 (m, 2H), 7.69 (d, J=13.3 Hz, 1H), 7.63 (s, 1H), 7.59-7.50 (m, 2H), 7.44 (d, J=7.4 Hz, 1H), 4.44 (br. s., 2H), 4.19 (t, J=5.9 Hz, 2H), 2.90 (t, J=6.1 Hz, 2H), 2.10 (d, J=3.9 Hz, 2H), 1.89 (d, J=5.5 Hz, 2H), 1.43 (s, 9H) ppm.

BIOLOGICAL ACTIVITY

The Btk inhibitor compounds of the invention having Formula (I) inhibit Btk kinase activity.

The term $IC_{50}$ means the concentration of the test compound that is required for 50% inhibition of its maximum effect in vitro.

Btk Enzyme Activity Assay Methods

Preparation of Un-Activated Btk Enzyme (25P Btk)

Un-activated full-length Btk recombinant protein was purified from baculovirus-transfected Sf21 cells. This enzyme when enriched to homogeneity has very low level of phosphorylation at Y223 and Y551, thus exhibited a lag-phase during the initial portion of its catalytic progress curve. This protein represents the un-activated state of the Btk enzyme.

Preparation of Activated Btk Enzyme (100P Btk):

Activated full-length Btk recombinant enzyme was expressed and purified in the same manner as the 25P enzyme, except an auto-phosphorylation step was added to the purification scheme. In doing so, >70% of Y223 and Y551 were phosphorylated and the lag-phase of the initial portion of the progress curve was eliminated. This protein represents the activated state of the Btk enzyme.

100P Btk Enzyme Activity Assay

Btk enzymatic activity was determined with the LANCE (Lanthanide Chelate Excite) TR-FRET (lime-resolved fluorescence resonance energy transfer) assay. In this assay, the potency ($IC_{50}$) of each compound was determined from an eleven point (1:3 serial dilution; final compound concentration range in assay from 1000 nM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM $MgCl_2$, 0.01% Brij-35, 1 mM EGTA, 0.05% BSA & 1 mM DTT) containing 13.3 pg/μL (133.3 pM) of 100P Btk enzyme (recombinant protein from baculovirus-transfected Sf9 cells: full-length Btk; MW=79378 Da). Following a 60 minute compound and enzyme incubation, each reaction was initiated by the addition of 2.5 μL 1× kinase buffer containing 8 μM biotinylated "A5" peptide (Biotin-EQEDEPEGDYFEWLE-$NH_2$) (SEQ-.ID.NO.: 1) and 100 μM ATP. The final reaction in each well of 10 consists of 100 pM 100P Btk, 2 μM biotin-A5-peptide, and 25 μM ATP. Phosphorylation reactions were allowed to proceed for 45 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate: anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

25P Btk Enzyme Activity Assay

Btk enzymatic activity was determined with the LANCE (Lanthanide Chelate Excite) TR-FRET (lime-resolved fluorescence resonance energy transfer) assay. In this assay, the potency ($IC_{50}$) of each compound was determined from an eleven point (1:3 serial dilution; final compound concentration range in assay from 1000 nM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM $MgCl_2$, 0.01% Brij-35, 1 mM EGTA, 0.05% BSA and 1 mM DTT) containing 26.67 pg/μL (266.7 pM) of 25P Btk enzyme (recombinant protein from baculovirus-transfected Sf9 cells: full-length Btk; MW=79378 Da). Following a 60 minute compound and enzyme incubation, each reaction was initiated by the addition of 2.5 μL 1× kinase buffer containing 8 μM biotinylated "A5" peptide (Biotin-EQEDEPEGDYFEWLE-$NH_2$), and 100 μM ATP. The final reaction in each well of 10 consists of 200 pM 25P Btk, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate:anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The following Table 3 provides specific $IC_{50}$ values for all the examples. The $IC_{50}$ values set forth below were determined according to assay method described above.

TABLE 3

| Compounds Btk binding potency | | |
|---|---|---|
| Example number | Btk binding $IC_{50}$ (nM) with 25 P | Btk binding $IC_{50}$ (nM) with 100 P |
| Example 1 | 0.14 | 111.8 |
| Example 2 | 10.9 | 340.7 |
| Example 3 | 0.16 | 16.0 |
| Example 4 | 38.6 | 1000 |
| Example 5 | 47.3 | 1000 |
| Example 6 | 0.15 | 3.8 |
| Example 7 | 64.5 | 1000 |
| Example 8 | 268.3 | 1000 |
| Example 9 | 0.073 | 5.3 |
| Example 10 | 0.80 | 298.8 |
| Example 11 | 0.16 | 29.3 |
| Example 12 | 29.6 | 1000 |
| Example 13 | 16.7 | 1000 |
| Example 14 | 172.8 | 1000 |
| Example 15 | 23.8 | 1000 |
| Example 16 | 0.49 | 144.9 |
| Example 17 | 0.16 | 13.0 |
| Example 18 | 0.13 | 11.6 |
| Example 19 | 0.48 | 429.4 |
| Example 20 | 7.7 | 1000 |
| Example 21 | 9.5 | 801.2 |
| Example 22 | 0.11 | 17.4 |
| Example 23 | 0.18 | 20.0 |
| Example 24 | 0.28 | 31.5 |
| Example 25 | 0.18 | 2.6 |
| Example 26 | 0.096 | 5.3 |
| Example 27 | 0.43 | 69.5 |
| Example 28 | 1.7 | 360.1 |

$R^7$ is:

(a.) a group of the formula —$C(O)N(R^{7a})(R^{7b})$, wherein $R^{7a}$ and $R^{7b}$ are independently H or $C_{1-3}$alkyl; or alternatively, $R^{7a}$ and $R^{7b}$ together with the N to which they are attached form a 5- to 6-membered heterocyclyl optionally containing 1 additional heteroatom selected from N or O;

(b.) Cy, wherein Cy is phenyl or a 5- or 6-membered heteroaryl containing 1 to 3 N ring atoms; wherein Cy is unsubstituted or substituted by 1 to 2 $R^c$ substituents selected from:

(i.) $C_{1-4}$alkyl, (ii.) a group of the formula —$C(R^{7d})_2CO_2H$, wherein $R^{7d}$ is H or $C_{1-3}$alkyl;

(iii.) —$CH_2CH_2OCH_3$; or (iv.) tetrahydropyranyl;

or alternatively, two $R^c$ substituents, together with the atoms to which they are attached form a 5- to 6-membered heterocyclyl containing 1 N ring atom;

(c.) —C(O)OH;

(d.) H;

(e.) $C_{1-3}$alkyl; or (f.) $C_{1-3}$fluoroalkyl;

$R^8$ is H, $C_{1-3}$alkyl or $C_{1-3}$hydroxyalkyl;

The invention claimed is:

1. A compound of Formula (I)

Formula (I)

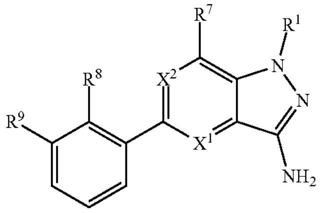

wherein:

$X^1$ is N or C(H);

$X^2$ is N or $C(R^6)$;

$R^1$ is H, $C_{1-3}$akyl, or —$CH_2$—$R^{1a}$, wherein $R^{1a}$ is phenyl or pyridyl;

$R^6$ is H or $C_{1-3}$alkyl;

$R^9$ is:

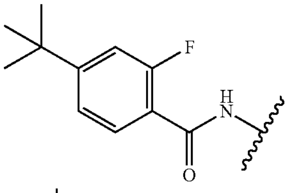

or

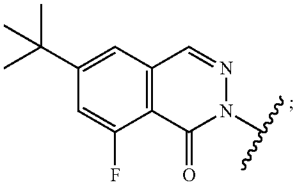

;

or a pharmaceutically acceptable salt thereof.

2. The compound of claim 1 or a pharmaceutically acceptable salt thereof, wherein $X^2$ is $C(R^6)$.

3. The compound of claim 1 or a pharmaceutically acceptable salt thereof, wherein $X^1$ and $X^2$ are both C(H).

4. The compound of claim 1 or a pharmaceutically acceptable salt thereof, wherein $R^1$ is H.

5. The compound of claim 1 or a pharmaceutically acceptable salt thereof, wherein $R^7$ is (a.) a group of the formula $—C(O)N(R^{7a})(R^{7b})$, wherein $R^{7a}$ and $R^{7b}$ are independently H or methyl; or alternatively, $R^{7a}$ and $R^{7b}$ together with the N to which they are attached form a morpholinyl ring;

(b.) Cy,wherein Cy is phenyl, pyrazolyl, or pyridinyl; wherein Cy is unsubstituted or substituted by 1 to 2 $R^c$ substituents selected from:

(i.) $C_{1-4}$alkyl, (ii.) a group of the formula $—C(R^{7d})_2CO_2H$, wherein $R^{7d}$ is H or methyl;

(iii.) $—CH_2CH_2OCH_3$; or (iv.) tetrahydropyranyl;

(c.) —C(O)OH;

(d.) H;

(e.) methyl; or (f.) trifluoromethyl.

6. The compound of claim 1 or a pharmaceutically acceptable salt thereof, wherein $R^8$ is hydroxymethyl or methyl.

7. A compound which is:

3-amino-5-[3-(6-tert-butyl-8-fluoro-1-oxophthalazin-2(1H)-yl)-2-(hydroxymethyl)phenyl]-1H-indazole-7-carboxylic acid, 2-[3-(3-amino-6-methyl-1H-indazol-5-yl)-2-(hydroxymethyl)phenyl]-6-tert-butyl-8-fluorophthalazin-1(2H)-one, 3-amino-5-[3-(6-tert-butyl-8-fluoro-1-oxophthalazin-2(1H)-yl)-2-(hydroxymethyl)phenyl]-1H-indazole-7-carboxamide, 2-{3-[3-amino-7-(trifluoromethyl)-1H-indazol-5-yl]-2-(hydroxymethyl)phenyl}-6-tert-butyl-8-fluorophthalazin-1(2H)-one, 3-amino-5-[3-(6-tert-butyl-8-fluoro-1-oxophthalazin-2(1H)-yl)-2-(hydroxymethyl)phenyl]-1-methyl-1H-indazole-7-carboxamide, 2-[3-{3-amino-7-[1-(1-methylethyl)-1H-pyrazol-4-yl]-1H-indazol-5-yl}-2-(hydroxymethyl)phenyl]-6-tert-butyl-8-fluorophthalazin-1(2H)-one, 3-amino-5-(3-{[(4-tert-butyl-2-fluorophenyl)carbonyl]amino}-2-methylphenyl)-1H-indazole-7-carboxamide, 3-amino-5-[3-({[2-fluoro-4-(2,2,2-trifluoro-1,1-dimethylethyl)phenyl]carbonyl}amino)-2-methylphenyl]-1H-indazole-7-carboxamide, 2-{3-[3-amino-7-(1-methyl-1H-pyrazol-4-yl)-1H-indazol-5-yl]-2-(hydroxymethyl)phenyl}-6-tert-butyl-8-fluorophthalazin-1(2H)-one, 2[3-(3-3-(3-amino-7-pyridin-3-yl-1H-indazol-5-yl)-2-(hydroxymethyl)phenyl]-6-tert-butyl-8-fluorophthalazin-1(2H)-one, 3-amino-5[3-(6-tert-butyl-8-fluoro-1-oxophthalazin-2(1H)-yl)-2-(hydroxymethyl)phenyl]-N-methyl-1H-indazole-7-carboxamide, 2-{3[3-amino-1-(pyridin-4-ylmethyl)-1H-indazol-5-yl]-2-(hydroxymethyl)phenyl}-6-tert-butyl-8-fluorophthalazin-1(2H)-one, N-{3[3-amino-7-(1-methyl-1H-pyrazol-4-yl)-1H-indazol-5-yl]-2-methylphenyl}-4-tert-butylbenzamide, 2-{3-[3-amino-7-(morpholin-4-ylcarbonyl)-1H-indazol-5-yl]-2-(hydroxymethyl)phenyl}-6-tert-butyl-8-fluorophthalazin-1(2H)-one, N-{3-[3-amino-7-(1-methyl-1H-pyrazol-4-yl)-1H-indazol-5-yl]-2-methylphenyl1}-4-tert-butyl-2-fluorobenzamide, 3-amino-5-[3-(6-tert-butyl-8-fluoro-1-oxo-3,4-dihydroisoquinolin-2(1H)-yl)-2-(hydroxymethyl)phenyl]-1H-indazole-7-carboxamide, 2-[3-{3-amino-7-[-1-(1-methylethyl)-1H-pyrazol-3-yl]-1H-indazol-5-yl}-2-(hydroxymethyl)phenyl]-6-tert-butyl-8-fluorophthalazin-1(2H)-one, N-{3-[3-amino-7-(1-methyl-1H-pyrazol-4-yl)-1H-indazol-5-yl]-2-(hydroxymethyl)phenyl}-4,5,6,7-tetrahydro-1-benzothiophene-2-carboxamide, 2-[3-(3-amino-7-phenyl-1H-indazol-5-yl)-2-(hydroxymethyl)phenyl]-6-tert-butyl-8-fluorophthalazin-1(2H)-one, 2-[3-(3-amino-1H-pyrazolo[4,3-b]pyridin-5-yl)-2-(hydroxymethyl)phenyl]-6-tert-butyl-8-fluorophthalazin-1(2H)-one, 2-[3-(3-amino-1H-pyrazolo[3,4-c]pyridin-5-yl)-2-(hydroxymethyl)phenyl]-6-tert-butyl-8-fluorophthalazin-1(2H)-one, 2-(3-(3-amino-7-(pyridin-2-yl)-1H-indazol-5-yl)-2-(hydroxymethyl)phenyl)-6-(tert-butyl)-8-fluorophthalazin-1(2H)-one, 2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)acetic acid, 2-(4-(3-amino-5-(3-(6-(tert-butyl)-8-fluoro-1-oxophthalazin-2(1H)-yl)-2-(hydroxymethyl)phenyl)-1H-indazol-7-yl)-1H-pyrazol-1-yl)-2-methylpropanoic acid, 2-(3-(3-amino-7-(1-(tetrahydro-2H-pyran-4-yl)-1H-pyrazol-4-yl)-1H-indazol-5-yl)-2-(hydroxymethyl)phenyl)-6-(tert-butyl)-8-fluorophthalazin-1(2H)-one, 2-(3-(3-amino-7-(1-(2-methoxyethyl)-1H-pyrazol-4-yl)-1H-indazol-5-yl)-2-(hydroxymethyl)phenyl)-6-(tert-butyl)-8-fluorophthalazin-1(2H)-one, 2-(3-(3-amino-7-(1,3-dimethyl-1H-pyrazol-4-yl)-1H-indazol-5-yl)-2-(hydroxymethyl)phenyl)-6-(tert-butyl)-8-fluorophthalazin-1(2H)-one, 2-(3-(3-amino-7-(4,5,6,7-tetrahydropyrazolo[1,5-a]pyridin-3-yl)-1H-indazol-5-yl)-2-(hydroxymethyl)phenyl)-6-(tert-butyl)-8-fluorophthalazin-1(2H)-one, or a pharmaceutically acceptable salt thereof.

8. A pharmaceutical composition comprising the compound of claim 1 or a pharmaceutically acceptable salt thereof and a pharmaceutically acceptable carrier.

* * * * *